United States Patent
Krolik et al.

(10) Patent No.: US 8,945,160 B2
(45) Date of Patent: Feb. 3, 2015

(54) APPARATUS AND METHODS FOR TREATING OBSTRUCTIONS WITHIN BODY LUMENS

(75) Inventors: Jeffrey A. Krolik, Campbell, CA (US); Gwendolyn Watanabe, Sunnyvale, CA (US); Juan Domingo, Lathrop, CA (US); Ray Betelia, San Jose, CA (US); James H. Dreher, Santa Monica, CA (US); Daryush Mirzaee, Sunnyvale, CA (US); Lucas Fernandez, Sunnyvale, CA (US)

(73) Assignee: Hotspur Technologies, Inc., Mountain View, CA (US)

( * ) Notice: Subject to any disclaimer, the term of this patent is extended or adjusted under 35 U.S.C. 154(b) by 113 days.

(21) Appl. No.: 12/843,004

(22) Filed: Jul. 23, 2010

(65) Prior Publication Data
US 2011/0125132 A1 May 26, 2011

Related U.S. Application Data

(63) Continuation-in-part of application No. 12/497,135, filed on Jul. 2, 2009, now Pat. No. 8,043,313.

(60) Provisional application No. 61/271,627, filed on Jul. 23, 2009, provisional application No. 61/283,035, (Continued)

(51) Int. Cl.
*A61M 25/10* (2013.01)
*A61B 17/22* (2006.01)
(Continued)

(52) U.S. Cl.
CPC .......... *A61B 17/22032* (2013.01); *A61B 17/221* (2013.01); *A61B 17/320725* (2013.01);
(Continued)

(58) Field of Classification Search
CPC ................. A61B 17/22032; A61B 17/32075; A61M 25/0074; A61M 25/0075; A61M 25/0079; A61M 25/10185

USPC ............................. 606/127, 159, 194, 200; 604/96.01–103.14, 509
See application file for complete search history.

(56) References Cited

U.S. PATENT DOCUMENTS

| 396,754 A | 1/1889 | Mayfield |
| 4,029,104 A | 6/1977 | Kerber |

(Continued)

FOREIGN PATENT DOCUMENTS

| CN | 1917802 A | 2/2007 |
| EP | 0 778 042 A2 | 6/1997 |

(Continued)

OTHER PUBLICATIONS

PCT International Search Report and Written Opinion for PCT/US2010/043165, Applicant: HotSpur Technologies, Inc., Forms PCT/ISA/220, PCT/ISA/210, and PCT/ISA/237; dated Apr. 11, 2011, 17 pages.

(Continued)

*Primary Examiner* — Kathleen Holwerda
(74) *Attorney, Agent, or Firm* — Baker & Hostetler LLP

(57) ABSTRACT

An apparatus is provided that is operable in different modes to perform various functions for treating a body lumen. The apparatus includes a shaft including proximal and distal ends, a lumen extending therebetween, and a balloon on the distal end. The apparatus includes a valve on the distal end that selectively opens or closes an outlet communicating with the lumen. With the valve open, fluid introduced into the lumen exits the outlet into a body lumen. With the valve closed, fluid introduced into the lumen expands the balloon. The valve may be biased to be closed, e.g., by a spring element disposed within the balloon. Optionally, the apparatus also includes an actuator for expanding a helical member within the balloon interior, e.g., either before or after expanding the balloon, such that the helical member and balloon may adopt an expanded helical shape for removing material within a body lumen.

13 Claims, 41 Drawing Sheets

Related U.S. Application Data filed on Nov. 25, 2009, provisional application No. 61/342,755, filed on Apr. 19, 2010, provisional application No. 61/397,854, filed on Jun. 17, 2010, provisional application No. 61/078,330, filed on Jul. 3, 2008, provisional application No. 61/153,620, filed on Feb. 18, 2009, provisional application No. 61/214,667, filed on Apr. 27, 2009, provisional application No. 61/215,732, filed on May 8, 2009.

(51) Int. Cl.
*A61B 17/221* (2006.01)
*A61B 17/3207* (2006.01)
*A61F 2/958* (2013.01)
*A61B 17/3205* (2006.01)
*A61M 25/00* (2006.01)

(52) U.S. Cl.
CPC .............. *A61F 2/958* (2013.01); *A61M 25/10* (2013.01); *A61M 25/1002* (2013.01); *A61M 25/1011* (2013.01); *A61M 25/104* (2013.01); *A61B 17/32056* (2013.01); *A61B 2017/22034* (2013.01); *A61B 2017/22061* (2013.01); *A61B 2017/2212* (2013.01); *A61B 2017/2215* (2013.01); *A61M 25/0097* (2013.01); *A61M 2025/0008* (2013.01); *A61M 2025/1068* (2013.01); *A61M 2025/1077* (2013.01); *A61M 2025/1084* (2013.01); *A61M 2025/1086* (2013.01); *A61M 2025/109* (2013.01)
USPC .................... 606/159; 604/99.01; 604/99.04; 604/509

(56) References Cited

U.S. PATENT DOCUMENTS

| | | | |
|---|---|---|---|
| 4,030,503 A * | 6/1977 | Clark, III | 606/159 |
| 4,273,128 A | 6/1981 | Lary | |
| 4,315,512 A | 2/1982 | Fogarty | |
| 4,545,367 A | 10/1985 | Tucci | |
| 4,646,742 A | 3/1987 | Packard | |
| 4,649,922 A | 3/1987 | Wiktor | |
| 4,653,496 A | 3/1987 | Bundy et al. | |
| 4,706,671 A | 11/1987 | Weinrib | |
| 4,762,130 A * | 8/1988 | Fogarty et al. | 606/159 |
| 4,784,636 A | 11/1988 | Rydell | |
| 4,813,934 A * | 3/1989 | Engelson et al. | 604/99.02 |
| 4,821,722 A | 4/1989 | Miller et al. | |
| 4,848,342 A | 7/1989 | Kaltenbach | |
| 4,848,344 A | 7/1989 | Sos et al. | |
| 4,890,611 A | 1/1990 | Monfort et al. | |
| 4,894,051 A | 1/1990 | Shiber | |
| 4,921,478 A | 5/1990 | Solano et al. | |
| 4,926,858 A | 5/1990 | Gifford, III et al. | |
| 4,950,277 A | 8/1990 | Farr | |
| 5,011,488 A | 4/1991 | Ginsburg | |
| 5,032,113 A | 7/1991 | Burns et al. | |
| 5,035,705 A | 7/1991 | Burns | |
| 5,059,176 A | 10/1991 | Winters | |
| 5,085,636 A | 2/1992 | Burns | |
| 5,090,959 A | 2/1992 | Samson et al. | |
| 5,100,388 A | 3/1992 | Behl et al. | |
| 5,100,423 A | 3/1992 | Fearnot | |
| 5,102,402 A | 4/1992 | Dror et al. | |
| 5,135,494 A | 8/1992 | Engelson | |
| 5,135,531 A | 8/1992 | Shiber | |
| 5,141,518 A | 8/1992 | Hess et al. | |
| 5,171,221 A | 12/1992 | Samson | |
| 5,176,698 A | 1/1993 | Burns et al. | |
| 5,192,286 A | 3/1993 | Phan et al. | |
| 5,192,290 A | 3/1993 | Hilal | |
| 5,192,295 A | 3/1993 | Danforth et al. | |
| 5,207,229 A | 5/1993 | Winters | |
| 5,211,651 A | 5/1993 | Reger et al. | |
| 5,217,434 A | 6/1993 | Arney | |
| 5,221,260 A | 6/1993 | Burns et al. | |
| 5,259,839 A | 11/1993 | Burns | |
| 5,295,959 A | 3/1994 | Gurbel et al. | |
| 5,303,714 A | 4/1994 | Abele et al. | |
| 5,304,198 A | 4/1994 | Samson | |
| 5,308,356 A | 5/1994 | Blackshear et al. | |
| 5,312,340 A | 5/1994 | Keith | |
| 5,320,604 A | 6/1994 | Walker et al. | |
| 5,338,295 A | 8/1994 | Cornelius et al. | |
| 5,342,301 A | 8/1994 | Saab | |
| 5,364,354 A | 11/1994 | Walker et al. | |
| 5,368,567 A | 11/1994 | Lee | |
| 5,372,601 A | 12/1994 | Lary | |
| 5,378,238 A | 1/1995 | Peters et al. | |
| 5,380,282 A | 1/1995 | Burns | |
| 5,383,856 A | 1/1995 | Bersin | |
| 5,385,152 A | 1/1995 | Abele et al. | |
| 5,403,276 A | 4/1995 | Schechter et al. | |
| 5,415,634 A | 5/1995 | Glynn et al. | |
| 5,419,774 A | 5/1995 | Willard et al. | |
| 5,423,745 A | 6/1995 | Todd et al. | |
| 5,423,846 A | 6/1995 | Fischell | |
| 5,437,632 A | 8/1995 | Engelson | |
| 5,454,788 A | 10/1995 | Walker et al. | |
| 5,454,789 A | 10/1995 | Burns et al. | |
| 5,464,395 A | 11/1995 | Faxon et al. | |
| 5,476,477 A | 12/1995 | Burns | |
| 5,484,408 A | 1/1996 | Burns | |
| 5,484,409 A | 1/1996 | Atkinson et al. | |
| 5,484,411 A | 1/1996 | Inderbitzen et al. | |
| 5,487,730 A | 1/1996 | Marcadis et al. | |
| 5,527,326 A | 6/1996 | Hermann et al. | |
| 5,569,195 A | 10/1996 | Saab | |
| 5,569,201 A | 10/1996 | Burns | |
| 5,571,122 A | 11/1996 | Kelly et al. | |
| 5,624,396 A | 4/1997 | McNamara et al. | |
| 5,643,298 A | 7/1997 | Nordgren et al. | |
| 5,643,304 A | 7/1997 | Schechter et al. | |
| 5,658,302 A | 8/1997 | Wicherski et al. | |
| 5,662,603 A | 9/1997 | Gelbfish | |
| 5,665,098 A | 9/1997 | Kelly et al. | |
| 5,683,410 A | 11/1997 | Samson | |
| 5,693,015 A | 12/1997 | Walker et al. | |
| 5,728,067 A | 3/1998 | Enger | |
| 5,749,849 A | 5/1998 | Engelson | |
| 5,766,191 A | 6/1998 | Trerotola | |
| 5,776,099 A | 7/1998 | Tremulis | |
| 5,779,698 A | 7/1998 | Clayman et al. | |
| 5,807,328 A * | 9/1998 | Briscoe | 604/102.02 |
| 5,836,961 A | 11/1998 | Kieturaksi et al. | |
| 5,843,103 A | 12/1998 | Wulfman | |
| 5,868,735 A | 2/1999 | Lafontaine | |
| 5,868,768 A | 2/1999 | Wicherski et al. | |
| 5,891,153 A | 4/1999 | Peterson | |
| 5,895,398 A | 4/1999 | Wensel et al. | |
| 5,906,606 A | 5/1999 | Chee et al. | |
| 5,919,162 A | 7/1999 | Burns | |
| 5,947,985 A | 9/1999 | Imran | |
| 5,954,737 A | 9/1999 | Lee | |
| 5,972,019 A | 10/1999 | Engelson et al. | |
| 5,980,486 A | 11/1999 | Enger | |
| 5,997,557 A | 12/1999 | Barbut et al. | |
| 6,004,328 A | 12/1999 | Solar | |
| 6,017,323 A | 1/2000 | Chee | |
| 6,036,717 A | 3/2000 | Mers et al. | |
| 6,050,972 A | 4/2000 | Zadno-Azizi et al. | |
| 6,066,158 A | 5/2000 | Engelson et al. | |
| 6,090,126 A | 7/2000 | Burns | |
| 6,096,055 A | 8/2000 | Samson | |
| 6,113,579 A | 9/2000 | Eidenschink et al. | |
| 6,129,708 A | 10/2000 | Enger | |
| 6,146,396 A | 11/2000 | Konya et al. | |
| 6,210,370 B1 | 4/2001 | Chi-Sing et al. | |
| 6,231,543 B1 | 5/2001 | Hegde et al. | |
| 6,231,588 B1 | 5/2001 | Zadno-Azizi | |
| 6,245,040 B1 | 6/2001 | Inderbitzen et al. | |
| 6,283,950 B1 | 9/2001 | Appling | |

(56) References Cited

U.S. PATENT DOCUMENTS

| | | | |
|---|---|---|---|
| 6,306,124 B1 | 10/2001 | Jones et al. | |
| 6,306,151 B1 | 10/2001 | Lary | |
| 6,325,778 B1 * | 12/2001 | Zadno-Azizi et al. | 604/99.02 |
| 6,350,252 B2 | 2/2002 | Ray et al. | |
| 6,440,097 B1 * | 8/2002 | Kupiecki | 604/509 |
| 6,454,775 B1 | 9/2002 | Demarais et al. | |
| 6,458,096 B1 | 10/2002 | Briscoe et al. | |
| 6,511,492 B1 | 1/2003 | Rosenbluth et al. | |
| 6,514,273 B1 | 2/2003 | Voss et al. | |
| 6,530,935 B2 | 3/2003 | Wensel et al. | |
| 6,542,781 B1 | 4/2003 | Koblish et al. | |
| 6,544,217 B1 | 4/2003 | Gulachenski | |
| 6,547,754 B1 | 4/2003 | Evans et al. | |
| 6,558,401 B1 | 5/2003 | Azizi | |
| 6,575,933 B1 | 6/2003 | Wittenberger et al. | |
| 6,589,206 B1 | 7/2003 | Sharkawy et al. | |
| 6,610,077 B1 | 8/2003 | Hancock et al. | |
| 6,620,179 B2 | 9/2003 | Boock et al. | |
| 6,626,861 B1 | 9/2003 | Hart et al. | |
| 6,638,245 B2 | 10/2003 | Miller et al. | |
| 6,660,014 B2 | 12/2003 | Demarais et al. | |
| 6,666,874 B2 | 12/2003 | Heitzmann et al. | |
| 6,679,860 B2 | 1/2004 | Stiger | |
| 6,685,722 B1 | 2/2004 | Rosenbluth et al. | |
| 6,711,444 B2 | 3/2004 | Koblish | |
| 6,743,208 B1 * | 6/2004 | Coyle | 604/164.13 |
| 6,824,545 B2 | 11/2004 | Sepetka et al. | |
| 6,945,977 B2 | 9/2005 | Demarais et al. | |
| 7,004,954 B1 | 2/2006 | Voss et al. | |
| 7,058,456 B2 | 6/2006 | Pierce | |
| 7,070,576 B2 | 7/2006 | O'Brien et al. | |
| 7,087,039 B1 | 8/2006 | Cox et al. | |
| 7,179,269 B2 | 2/2007 | Welch et al. | |
| 7,182,755 B2 | 2/2007 | Tal | |
| 7,186,237 B2 | 3/2007 | Meyer et al. | |
| 7,244,270 B2 | 7/2007 | Lesh | |
| 7,250,042 B2 | 7/2007 | Kataishi et al. | |
| 7,306,617 B2 | 12/2007 | Majercak | |
| 7,338,501 B2 | 3/2008 | Teague et al. | |
| 7,377,931 B2 | 5/2008 | Bagaoisan | |
| 7,462,183 B2 | 12/2008 | Behl et al. | |
| 7,507,246 B2 | 3/2009 | McGuckin et al. | |
| 7,517,352 B2 | 4/2009 | Evans et al. | |
| 7,758,604 B2 | 7/2010 | Wu et al. | |
| 7,819,887 B2 | 10/2010 | McGuckin et al. | |
| 7,862,576 B2 | 1/2011 | Gurm | |
| 7,873,404 B1 | 1/2011 | Patton | |
| 7,879,066 B2 | 2/2011 | Desai et al. | |
| 7,883,516 B2 | 2/2011 | Huang et al. | |
| 8,043,313 B2 | 10/2011 | Krolik et al. | |
| 2001/0031981 A1 | 10/2001 | Evans et al. | |
| 2002/0010487 A1 | 1/2002 | Evans et al. | |
| 2002/0133117 A1 | 9/2002 | Zadno-Azizi et al. | |
| 2002/0177870 A1 | 11/2002 | Sepetka et al. | |
| 2003/0004542 A1 | 1/2003 | Wensel et al. | |
| 2003/0009190 A1 | 1/2003 | Kletschka et al. | |
| 2003/0163158 A1 | 8/2003 | White | |
| 2004/0006361 A1 | 1/2004 | Boyle et al. | |
| 2004/0133232 A1 | 7/2004 | Rosenbluth et al. | |
| 2004/0181150 A1 | 9/2004 | Evans et al. | |
| 2004/0236363 A1 | 11/2004 | Kieturaksi et al. | |
| 2004/0243156 A1 | 12/2004 | Wu et al. | |
| 2004/0243167 A1 | 12/2004 | Tanaka et al. | |
| 2005/0038383 A1 | 2/2005 | Kelley et al. | |
| 2005/0059993 A1 | 3/2005 | Ramzipoor et al. | |
| 2005/0131453 A1 | 6/2005 | Parodi | |
| 2005/0288632 A1 | 12/2005 | Willard | |
| 2006/0009784 A1 | 1/2006 | Behl et al. | |
| 2006/0036277 A1 | 2/2006 | Kieturakis et al. | |
| 2006/0074442 A1 | 4/2006 | Noriega et al. | |
| 2006/0106407 A1 | 5/2006 | McGuckin et al. | |
| 2006/0200047 A1 | 9/2006 | Galdonik et al. | |
| 2006/0253145 A1 | 11/2006 | Lucas | |
| 2007/0016244 A1 | 1/2007 | Behl et al. | |
| 2007/0038225 A1 | 2/2007 | Osborne | |
| 2007/0083158 A1 | 4/2007 | Hirszowicz et al. | |
| 2007/0129752 A1 | 6/2007 | Webler et al. | |
| 2007/0239182 A1 | 10/2007 | Glines et al. | |
| 2007/0293935 A1 | 12/2007 | Olsen et al. | |
| 2008/0064930 A1 | 3/2008 | Turliue | |
| 2008/0125798 A1 | 5/2008 | Osborne et al. | |
| 2008/0177277 A1 | 7/2008 | Huang et al. | |
| 2008/0200873 A1 | 8/2008 | Espinosa et al. | |
| 2008/0228209 A1 | 9/2008 | DeMello et al. | |
| 2008/0262487 A1 | 10/2008 | Wensel et al. | |
| 2008/0269798 A1 | 10/2008 | Ramzipoor et al. | |
| 2008/0306440 A1 | 12/2008 | Hirszowicz et al. | |
| 2009/0018549 A1 | 1/2009 | Desai et al. | |
| 2009/0018569 A1 | 1/2009 | Desai et al. | |
| 2009/0076539 A1 | 3/2009 | Valaie | |
| 2010/0036312 A1 | 2/2010 | Krolik et al. | |
| 2010/0036410 A1 | 2/2010 | Krolick et al. | |
| 2010/0137892 A1 | 6/2010 | Krolik et al. | |
| 2011/0093000 A1 | 4/2011 | Ogle et al. | |
| 2012/0078096 A1 | 3/2012 | Krolik et al. | |
| 2012/0109057 A1 | 5/2012 | Krolik et al. | |
| 2012/0197193 A1 | 8/2012 | Krolik et al. | |

FOREIGN PATENT DOCUMENTS

| | | |
|---|---|---|
| JP | S62-233168 A | 10/1987 |
| JP | S63-192457 A | 8/1988 |
| JP | H03-080872 A | 4/1991 |
| JP | H08-509397 A | 10/1996 |
| JP | 2004-136103 A | 5/2004 |
| JP | 2008-504067 A | 2/2008 |
| WO | WO-94/18894 A1 | 9/1994 |
| WO | 2008117256 | 10/2008 |
| WO | 2008117257 | 10/2008 |

OTHER PUBLICATIONS

PCT International Search Report and Written Opinion for PCT/US2009/049639, Applicant: HotSpur Technologies, Inc., Forms PCT/ISA/220, PCT/ISA/210, and PCT/ISA/237; dated Feb. 1, 2010, 14 pages.

Extended European Search Report for European Application No. 09774584.8, dated Oct. 17, 2013.

Communication Pursuant to Article 94(3) EPC mailed Jun. 18, 2014, as received in European Patent Application No. 09774584.8.

Examination Report mailed Jun. 23, 2014, as received in Singaporean Patent Application No. 2010090801.

First Office Action mailed Jul. 16, 2013, as received in Chinese Patent Application No. 201080040808.2, and an English language summary thereof.

First Office Action mailed Jul. 23, 2013, as received in Japanese Patent Application No. 2011-512752, and an English language summary thereof.

First Office Action mailed Jun. 3, 2014, as received in Japanese Patent Application No. 2012-521865.

First Office Action mailed Nov. 1, 2012, as receiving in Chinese Patent Application No. 200980129911.1, and an English language translation thereof.

International Search Report and Written Opinion mailed Dec. 6, 2012, as received in International Application No. PCT/US2012/025734.

International Search Report and Written Opinion mailed Jan. 27, 2010, as received in International Application No. PCT/US2009/046659.

International Search Report and Written Opinion mailed Mar. 18, 2013, as received in International Application No. PCT/US2012/061672.

Invitation to Respond to Written Opinion mailed Nov. 8, 2012, as received in Singaporean Patent Application No. 2010090801.

Notice of Rejection mailed Mar. 4, 2014, as received in Japanese Patent Application No. 2011-512752, and an English language summary thereof.

(56) References Cited

OTHER PUBLICATIONS

Notice of Rejection mailed Sep. 3, 2013, as received in Japanese Patent Application No. 2011-516896, and an English language summary thereof.

Office Action mailed Sep. 13, 2012, as received in Chinese Patent Application No. 200980134164.0.

Patent Examination Report No. 1 mailed Mar. 13, 2013, as received in Australian Patent Application No. 2009266808.

Second Office Action mailed Mar. 19, 2013, as received in Chinese Patent Application No. 201080040808.2, and an English language summary thereof.

* cited by examiner

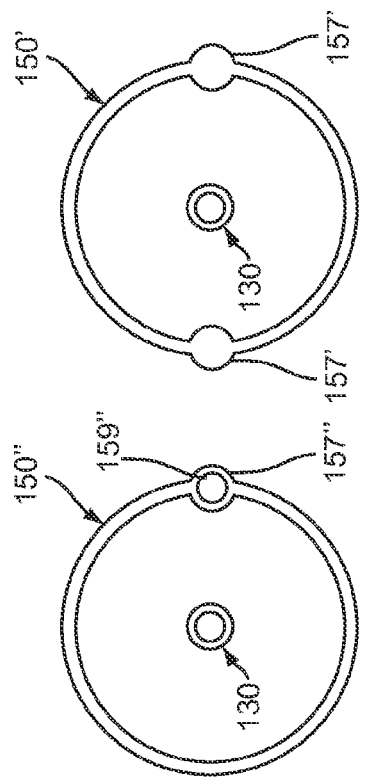
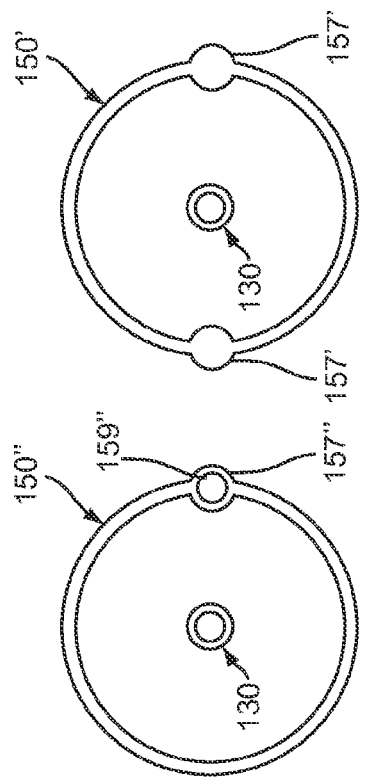
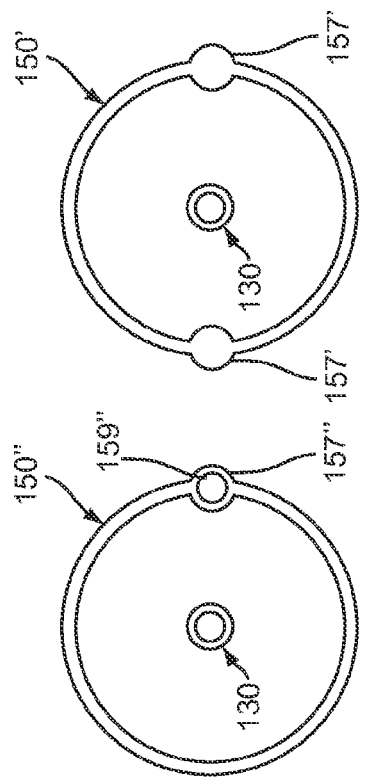
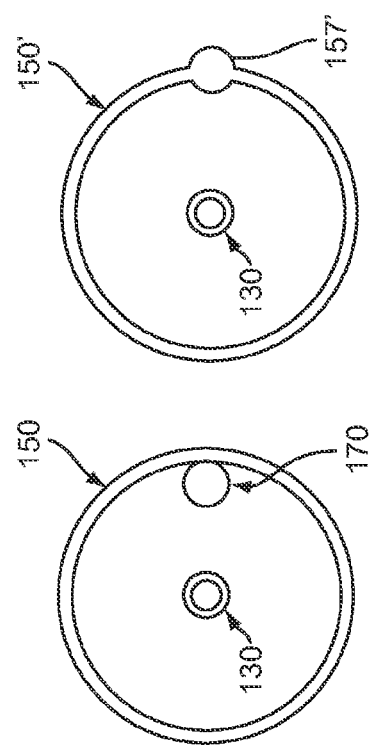
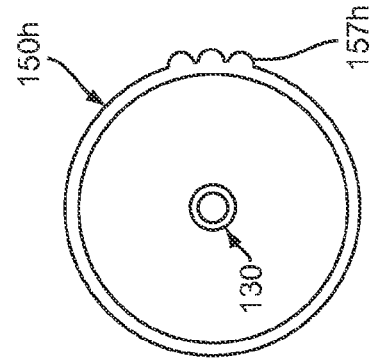
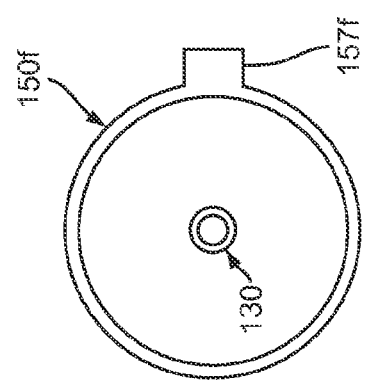
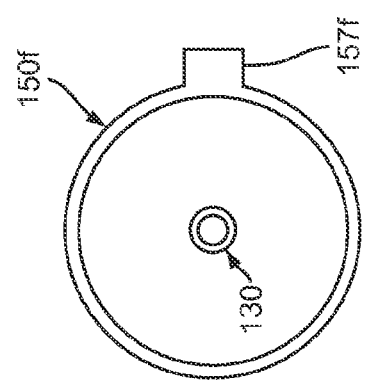
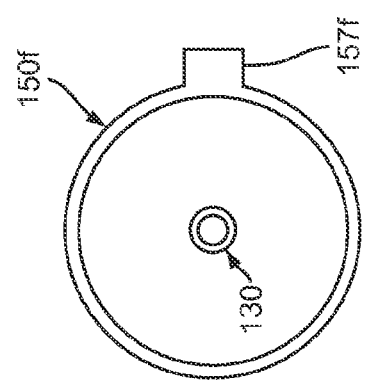
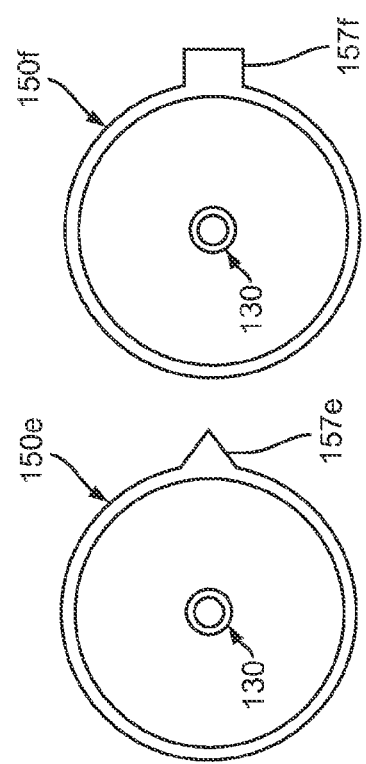
FIG. 7A  FIG. 7B  FIG. 7C  FIG. 7D
FIG. 7E  FIG. 7F  FIG. 7G  FIG. 7H

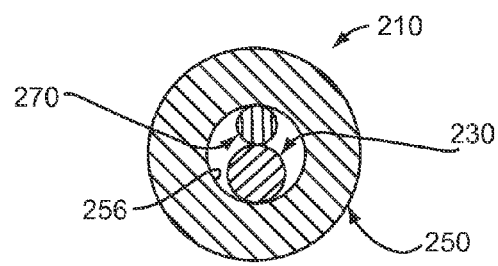
FIG. 10A
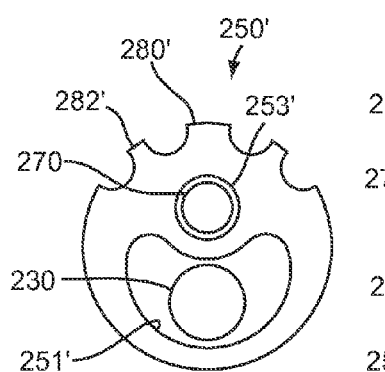 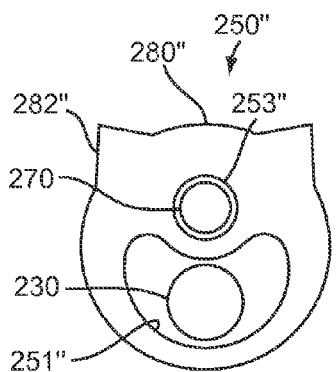 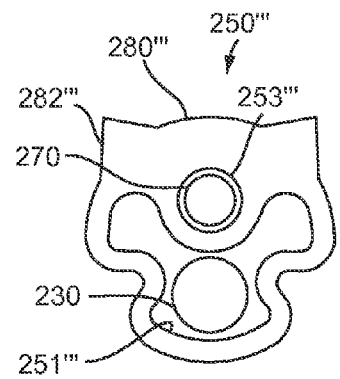
FIG. 10B    FIG. 10C    FIG. 10D

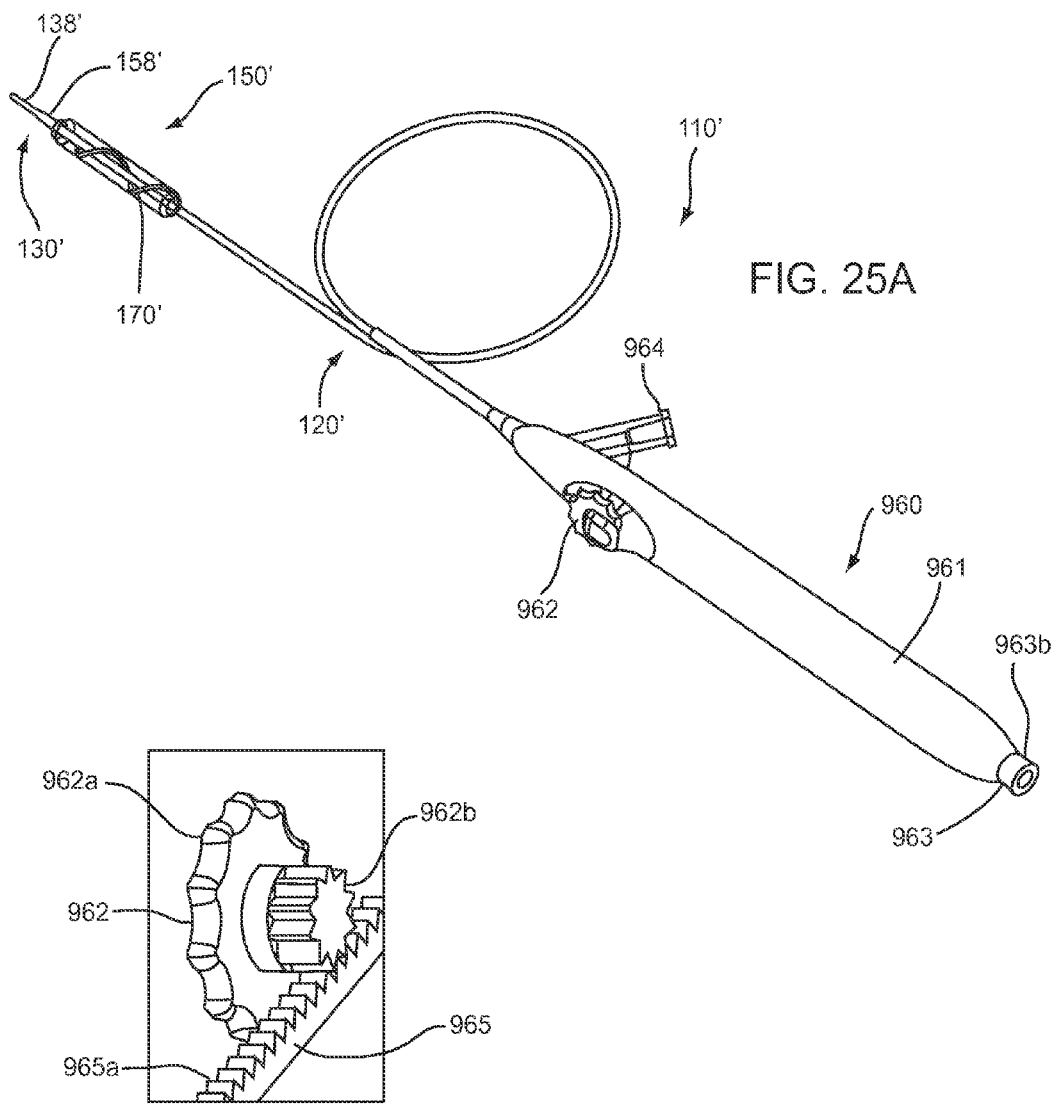

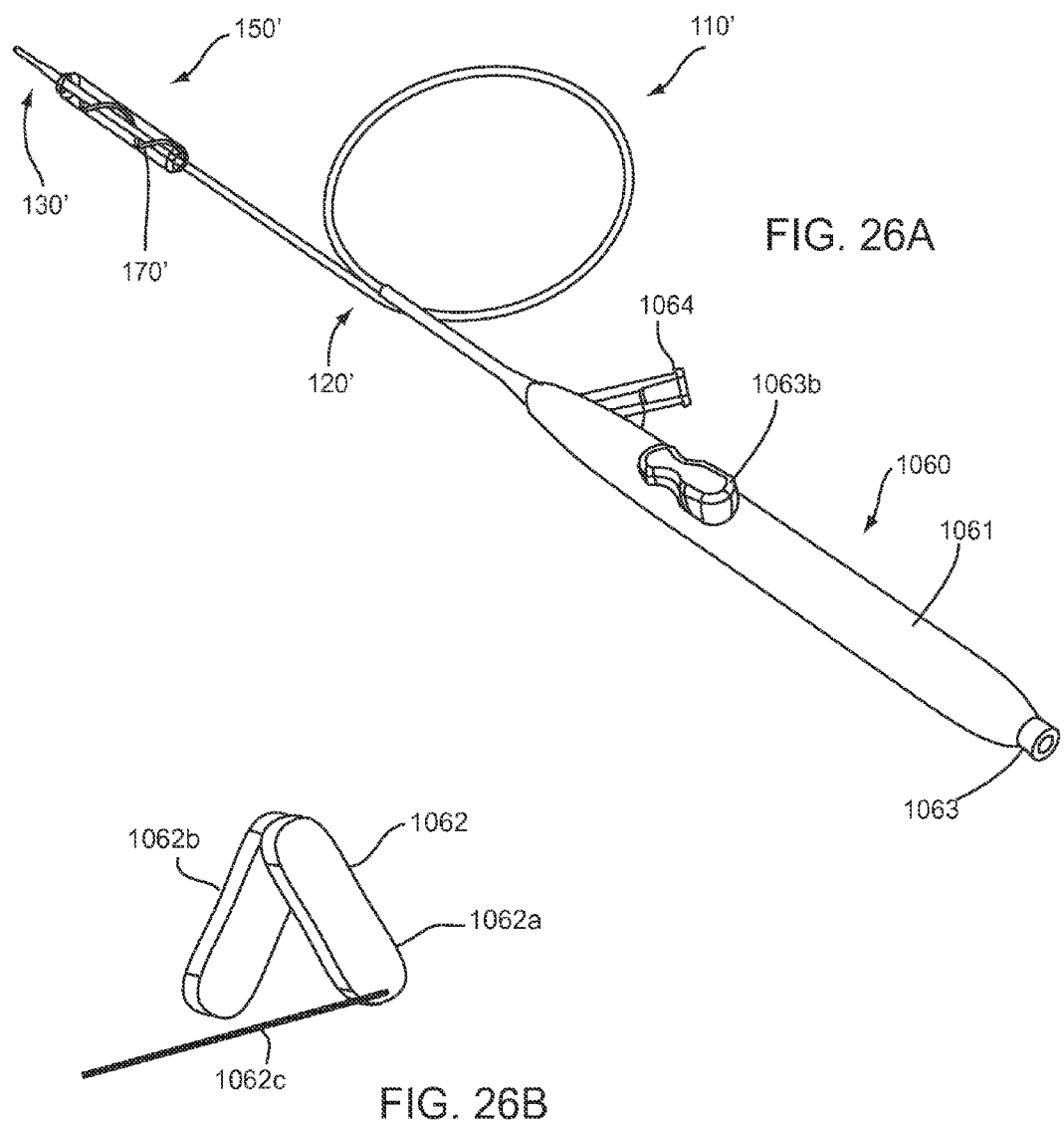

APPARATUS AND METHODS FOR TREATING OBSTRUCTIONS WITHIN BODY LUMENS

RELATED APPLICATIONS

This application claims benefit of provisional application Ser. Nos. 61/271,627, filed Jul. 23, 2009, 61/283,035, filed Nov. 25, 2009, 61/342,755, filed Apr. 19, 2010, and 61/397,854, filed Jun. 17, 2010, and is a continuation-in-part of co-pending application Ser. No. 12/497,135, filed Jul. 2, 2009, which claims benefit of U.S. provisional application Ser. Nos. 61/153,620, filed Feb. 18, 2009, 61/214,667, filed Apr. 27, 2009, and 61/215,732, filed May 8, 2009. The entire disclosures of these applications are expressly incorporated by reference herein.

FIELD OF THE INVENTION

The present invention relates generally to apparatus for treating obstructive material and/or other obstructions within a body lumen of a patient, e.g., within a tubular graft, aorto-venous fistula, blood vessel, and the like. More particularly, the present invention relates to apparatus, e.g., balloon catheters, for infusing fluids into a body lumen, for removing or otherwise capturing thrombus or other obstructive material within a body lumen, and/or for dilating a body lumen, and to methods for making and using such apparatus.

BACKGROUND

Flow within a blood vessel or other body lumen within a patient's vasculature may become constricted or ultimately interrupted for a variety of reasons. For example, a vessel may gradually narrow due to inflammation and/or cell proliferation. In addition, thrombus may form due to such narrowing or other flow problems within a vessel.

For example, an aorto-venous graft may be implanted in an arm of a patient experiencing kidney failure, e.g., to facilitate dialysis treatment. Such grafts may be a fistula formed directly in the patient's body, e.g., through tissue between an adjacent artery and vein or other vessels, may be a xenograft implanted between two vessels, or may be a synthetic graft. Such grafts only have a limited life cycle due to inflammation, thrombus formation, and the like. Once such a graft becomes sufficiently occluded or otherwise deteriorates, a new graft must be implanted at a new location for subsequent treatment.

Accordingly, apparatus and methods for removing material from aorto-venous grafts, blood vessels, or other body lumens and/or otherwise treating body lumens would be useful.

SUMMARY

The present invention is directed to apparatus for treating a body lumen of a patient, e.g., a tubular graft, aorto-venous fistula, blood vessel, and the like. More particularly, the present invention is directed to apparatus for infusing fluids into a body lumen, for removing or otherwise capturing thrombus or other obstructive material within a body lumen, and/or for dilating a body lumen, and to methods for making and using such apparatus.

In accordance with a first embodiment, an apparatus is provided for treating a body lumen that is operable in different modes to perform various functions, e.g., possibly reducing the number of device exchanges during a procedure. For example, the apparatus may include a shaft including a proximal end, a distal end sized for introduction into a body lumen, a lumen extending therebetween, and a balloon on the distal end having an interior communicating with the lumen. The apparatus may also include a valve on the distal end of the shaft that selectively opens or closes an outlet communicating with the lumen. With the valve open, fluid introduced into the lumen may exit the outlet into a body lumen beyond the distal end. With the valve closed, fluid introduced into the lumen may expand the balloon from a contracted condition to an expanded condition, e.g., a cylindrical shape for dilating an obstruction within a body lumen or a bulbous shape for removing material within the body lumen. Optionally, the valve may include a stop that may be extended to push a distal end of the balloon, e.g., to stretch or otherwise reduce a profile of the balloon and/or otherwise facilitate introduction into a patient's body.

In addition or alternatively, the apparatus may include an actuator for axially compressing the balloon, and the balloon may be configured to expand from the contracted condition to an expanded helical shape when axially compressed. For example, the actuator may include an inner member within the shaft that is coupled to a distal end of the balloon, and a helical member may extend around the inner member within the balloon. When the inner member is directed proximally or otherwise actuated, the helical member may be compressed and consequently expand radially outwardly, thereby expanding the balloon to the expanded helical shape. The inner member may be extended distally to extend and return the balloon back towards the contracted condition, e.g., after using the balloon in the expanded helical shape to remove material within a body lumen.

In accordance with another embodiment, an apparatus is provided for treating a body lumen that includes an elongate tubular outer member including a proximal end, a distal end, and a first lumen extending between the proximal and distal ends; an expandable balloon including a proximal end secured to the tubular member distal end, and a distal end including an outlet, the balloon including an interior communicating with the first lumen and the balloon outlet; and an elongate inner member slidably disposed within the first lumen. The elongate member may include a proximal end adjacent the tubular member proximal end, and a distal end extending from the balloon outlet. The balloon and elongate member may include cooperating features providing a valve for selectively opening and closing the balloon outlet. For example, a sealing member may be provided on the distal end of the elongate member sized to be engaged with the balloon distal end to substantially seal the outlet from fluid flow.

The elongate member may be movable between a first position wherein the sealing member is spaced apart from the balloon outlet such that fluid introduced through the first lumen passes through the balloon interior and out the balloon outlet, and a second position wherein the sealing member substantially seals the balloon outlet such that fluid introduced through the first lumen enters the balloon interior to expand the balloon.

Optionally, the elongate member may be biased to one of the first and second positions, but may be selectively directed to the other of the first and second positions. In one embodiment, a spring element may be provided within the balloon interior that is coupled to the elongate member for biasing the elongate member proximally, e.g., to engage the sealing member with the outlet to substantially seal the outlet. For example, the spring element may be coupled between a spring stop on the distal end of the balloon and a collar or other attachment member on the elongate member. When the elongate member is advanced distally to open the outlet, the spring element may be compressed between the spring stop and the collar such that when the elongate member is released, the spring element may automatically direct the elongate member proximally to reseal or enhance resealing the outlet with the sealing member.

If desired, the distal end of the balloon may include a distal tip shaped and/or configured to facilitate sealing and/or opening the outlet. For example, in one embodiment, the sealing member may include a tapered proximal end, and the distal tip may be flared outwardly away from the balloon such that the tapered proximal end of the sealing member may be seated at least partially in the flared distal tip. Such an embodiment may increase surface contact between the sealing member and the distal end, which may enhance sealing the outlet. In addition or alternatively, the flared distal tip may maximize the free area of the outlet when the sealing member is directed away from the outlet.

In another embodiment, a distal tip may be provided that is resiliently expandable, e.g., to increase surface contact between the sealing member and the distal end of the balloon to enhance sealing the outlet. For example, the distal tip may be relatively thin compared to the distal end of the balloon such that, when the sealing member is directed proximally into the distal tip, the distal tip may expand and conform to the shape of the sealing member. When the sealing member is directed distally to open the outlet, the distal tip may resiliently return to its original size and/or shape.

In addition or alternatively, the elongate inner member may include a "J" or otherwise curved distal tip, e.g., extending distally from the sealing member or otherwise distally from the distal end of the inner member. The distal tip may be sufficiently flexible such that, when a guidewire or other instrument is advanced through the elongate member into the distal tip, the distal tip may be substantially straightened, which may facilitate advancing the apparatus over the guidewire. When the guidewire is withdrawn from the distal tip, the distal tip may resiliently return to its curved shape, which may facilitate locating and/or advancing the apparatus into a branch from a main vessel or other body lumen.

Optionally, any of the apparatus herein may include a helical member including a first end coupled to the tubular member distal end and a second end coupled to the elongate member distal end, the helical member extending helically around the elongate member within the balloon interior. The elongate member may be movable to a third position in which the elongate member distal end is directed towards the tubular member distal end to cause the helical member to compress axially and expand radially outwardly, thereby expanding the balloon to an expanded helical shape.

In accordance with still another embodiment, an apparatus is provided for treating a body lumen that includes an outer member including a proximal end, a distal end sized for introduction into a body lumen, and a first lumen extending between the proximal and distal ends; and an expandable balloon including a proximal end secured to the outer member distal end, and a distal end comprising an outlet, the balloon including an interior communicating with the first lumen and the balloon outlet. An inner member is slidably disposed within the first lumen, the inner member including a proximal end adjacent the outer member proximal end, a distal end extending from the balloon outlet, and a sealing member on the inner member distal end. The inner member may be movable between a first position wherein the sealing member is spaced from the balloon outlet such that fluid introduced through the first lumen passes through the balloon interior and out the balloon outlet, and biased to a second position wherein the sealing member substantially seals the balloon outlet such that fluid introduced through the first lumen enters the balloon interior to expand the balloon. For example, a spring element may be provided between a spring stop in the balloon distal end and the inner member distal end for biasing the inner member towards the second position.

In accordance with yet another embodiment, an apparatus is provided for treating a body lumen that includes an outer tubular member including a proximal end, a distal end, and a first lumen extending between the proximal and distal ends; an inner member slidably disposed within the first lumen; and an expandable balloon including a proximal end secured to the outer member distal end, an interior communicating with the first lumen and a balloon outlet. The inner member includes a distal end extending from the balloon outlet, and carrying one or more sealing members. A helical member includes a first end coupled to the outer member distal end and a second end coupled to the inner member distal end, the helical member extending helically around the inner member within the balloon interior.

The inner member may be movable relative to the outer member for deploying the balloon in multiple modes. For example, the inner member may be movable from a first position wherein the sealing member is spaced from the balloon outlet such that fluid introduced through the first lumen passes through the balloon interior and out the balloon outlet, and a second position wherein the sealing member substantially seals the balloon outlet such that fluid introduced through the first lumen enters the balloon interior to expand the balloon. In addition or alternatively, the inner member may be movable from the first or second position to a third position in which the inner member distal end is directed proximally towards the outer member distal end to cause the helical member to expand radially outwardly, thereby expanding the balloon to an expanded helical shape.

In accordance with still another embodiment, an apparatus is provided for treating a body lumen that includes an outer tubular member including a first lumen extending between proximal and distal ends thereof, an inner member slidably disposed within the first lumen, and an expandable balloon comprising a proximal end secured to the outer member distal end, and a distal end coupled to a distal end of the inner member. The balloon includes an interior communicating with the first lumen such that inflation media may be delivered through the first lumen into the balloon interior for expanding the balloon radially outwardly from a contracted condition to an expanded condition, e.g., defining a cylindrical or bulbous shape. The inner member may be movable axially relative to the outer member for causing the balloon to compress axially and expand radially from the contracted condition to an expanded helical shape.

For example, the apparatus may include a helical member extending helically around the inner member within the balloon interior, and including a first end coupled to the outer member distal end and a second end coupled to the inner member. When the inner member is moved axially, the helical member may be compressed axially and expanded radially outwardly, thereby directing the balloon to the expanded helical shape.

Optionally, the inner member may include a second lumen extending between the inner member proximal and distal ends, e.g., for receiving a guidewire or other rail. Thus, the apparatus may be advanced over a guidewire loaded through the second lumen. Once the balloon is disposed within a target body lumen, the inner member may be directed to one or more of the first, second, and/or third positions, as desired, to perform various functions using the apparatus, e.g., without having to remove the apparatus and/or introduce another device into the body lumen.

In accordance with yet another embodiment, an apparatus is provided for treating a body lumen that includes an elongate outer member including a proximal end comprising a handle, a distal end sized for introduction into a body lumen, and a first lumen extending between the proximal and distal ends, and an expandable balloon including a proximal end secured to the outer member distal end, and a distal end comprising an outlet, the balloon including an interior communicating with the first lumen and the balloon outlet. An inner member is slidably disposed within the first lumen, the inner member including a proximal end adjacent the outer member proximal end, a distal end extending from the balloon outlet, and a sealing member on the inner member distal end. A first actuator may be provided on the handle coupled to the inner member for moving the inner member between a first position wherein the sealing member is spaced from the balloon outlet such that fluid introduced through the first lumen passes through the balloon interior and out the balloon outlet, and a second position wherein the sealing member substantially seals the balloon outlet such that fluid introduced through the first lumen enters the balloon interior to expand the balloon.

The apparatus may also include a helical member including a distal end coupled to the inner member distal end and a proximal end disposed proximal to the distal end, the helical member extending helically around the inner member within the balloon interior. A second actuator may be provided on the handle coupled to the proximal end of the helical member for moving the helical member proximal end distally to cause the helical member to compress axially and expand radially outwardly.

The helical member may be expanded and collapsed independent of movement of the inner member between the first and second positions. For example, a source of inflation media may be coupled to the apparatus for expanding the balloon before activating the second actuator to expand the helical member such that the helical member expands substantially unimpeded within the balloon interior. In addition or alternatively, a source of vacuum may communicate with the first lumen for collapsing the balloon after expanding the helical member such that the balloon conforms substantially to the shape of the helical member to adopt an expanded helical shape. In an exemplary embodiment, both the source of inflation media and the source of vacuum may be a single syringe for delivering fluid into and removing fluid from the balloon interior to expand and collapse the balloon.

In accordance with still another embodiment, an apparatus is provided for treating a body lumen that includes an outer member including a proximal end, a distal end sized for introduction into a body lumen, and a first lumen extending between the proximal end and an outlet in the distal end. An inner member may be slidably disposed within the first lumen that includes a proximal end adjacent the outer member proximal end, and a distal end adjacent the outer member distal end. The apparatus may also include an expandable balloon including proximal and distal ends secured to the outer member distal end, and an interior communicating with the first lumen via one or more openings in the outer member distal end.

A sealing member may be provided on the inner member distal end, and the inner member may be movable between a first position wherein the sealing member is spaced from the outlet such that fluid introduced through the first lumen exits the outlet, and a second position wherein the sealing member substantially seals the outlet such that fluid introduced through the first lumen enters the balloon interior to expand the balloon. Optionally, the inner member may be biased towards one of the first and second positions. For example, a spring element may be coupled between a spring stop in the balloon distal end and the inner member distal end for enhancing a seal between the sealing member and the outlet and/or for biasing the inner member towards the second position, e.g., to automatically seal the outlet with the sealing member.

In accordance with yet another embodiment, an apparatus is provided for treating a body lumen that includes an outer member including a proximal end, a distal end sized for introduction into a body lumen, and a first lumen extending between the proximal and distal ends, and an expandable balloon including a proximal end secured to the outer member distal end, and a distal end including an outlet. The balloon may include an interior communicating with the first lumen and the balloon outlet. An inner member is slidably disposed within the first lumen, the inner member including a proximal end adjacent the outer member proximal end, a distal end extending from the balloon outlet, and a sealing member on the inner member distal end. The inner member may be movable between a first position wherein the sealing member is spaced from the balloon outlet such that fluid introduced through the first lumen passes through the balloon interior and out the balloon outlet, and a second position wherein the sealing member substantially seals the balloon outlet such that fluid introduced through the first lumen enters the balloon interior to expand the balloon.

In addition, the balloon may include a distal tip extending distally from the balloon distal end that is configured for facilitating opening and/or closing the outlet, e.g., for maximizing surface contact between the sealing member and the distal tip when the inner member is in the second position for enhancing a seal of the outlet. For example, in one embodiment, the sealing member may include a tapered proximal end, and the balloon may include a distal tip extending distally from the balloon distal end, the distal tip biased to flare outwardly away from the balloon for receiving the tapered proximal end of the sealing member therein.

In another embodiment, the sealing member may include a tapered proximal end, and the balloon may include a distal tip extending distally from the balloon distal end, the distal tip comprising flexible material such that the distal tip resiliently expands for receiving the tapered proximal end of the sealing member therein in the second position. For example, the distal tip may be configured to resiliently return towards its original size when the inner member is directed from the second position to the first position to move the sealing member away from the balloon outlet.

Optionally, in any of these embodiments, a coating may be provided on an inner surface of at least a portion of the balloon distal end and/or distal tip to reduce friction between the balloon distal end and/or distal tip and the sealing member in the second position.

In another option, in any of these embodiments, the distal end of the balloon may be sized to provide a predetermined resistance to fluid flow therethrough. For example, the spring stop or other feature within the distal end may partially constrict the passage through the distal end leading to the outlet. Thus, if desired, with the outlet open, the distal end may provide sufficient resistance to fluid flow therethrough that fluid delivered into the balloon interior may at least partially expand the balloon as well as deliver fluid through the outlet into a body lumen.

In accordance with still another embodiment, an apparatus is provided for treating a body lumen that includes an outer member including a proximal end, a distal end sized for introduction into a body lumen, and a first lumen extending between the proximal end and an outlet in the distal end; and an inner member slidably disposed within the first lumen, the inner member comprising a proximal end adjacent the outer member proximal end, and a distal end extending distally beyond the outer member distal end. A sealing member is provided on the inner member distal end that includes one or more passages therethrough, and an expandable balloon is provided that includes a distal end secured to the inner member distal end distally beyond the sealing member, and a proximal end secured to the sealing member such that an interior of the balloon communicates with the one or more passages. The inner member may be movable between a first position wherein the sealing member is spaced from the outlet of the outer member such that fluid introduced through the first lumen passes through the outlet into a region around the apparatus, and a second position wherein the sealing member substantially seals the outlet such that fluid introduced through the first lumen passes through the one or more passages and enters the balloon interior to expand the balloon.

In accordance with another embodiment, a method is provided for treating a body lumen of a patient using a balloon apparatus that includes an elongate shaft including a first lumen extending between proximal and distal ends thereof, and a balloon carried on the distal end of the shaft that includes an outlet and an interior communicating with the first lumen and the outlet. The distal end of the shaft may be introduced into a body lumen with the balloon in a contracted condition, and positioned relative to obstructive material within the body lumen that is to be removed. Once positioned adjacent the obstructive material, the balloon may be expanded from the contracted condition to an expanded helical shape, and the distal end of the apparatus may be directed along the body lumen with the balloon in the expanded helical shape to remove the material from the body lumen. For example, the helical shape of the balloon may enhance dislodging material adhered to a wall of the body lumen. Optionally, the balloon may include one or more features, e.g., edges, grooves, and the like, to facilitate separating adherent material from the wall of the body lumen. If desired, the balloon may be returned to the contracted condition, moved to a new location within the body lumen, and again expanded to the expanded helical shape to remove additional material within the body lumen. Once sufficient material is removed, the balloon may be returned to the contracted condition.

Before or after removing obstructive material from the body lumen, inflation media may be introduced through the first lumen into the balloon interior to expand the balloon from the contracted condition to an expanded condition, e.g., defining a substantially cylindrical shape. The balloon may be expanded to dilate an obstruction, lesion or otherwise treat a wall of the body lumen. After dilating the body lumen, the inflation media may be withdrawn from the balloon interior through the first lumen to collapse the balloon back towards the contracted condition.

If the apparatus includes a valve adjacent the balloon for opening or closing an outlet communicating with the first lumen and the balloon interior, the valve may be closed before inflating the balloon. Optionally, at any time during the procedure, the valve may be opened, for example, to infuse fluid into the body lumen, e.g., for diagnostic and/or therapeutic purposes. During such infusion, the outlet of the balloon may provide substantially minimal resistance to fluid flow such that substantially all of the fluid delivered into the balloon exits the outlet. Alternatively, the outlet may provide a predetermined resistance to fluid flow therethrough such that some of the fluid delivered into the balloon expands the balloon while the remaining fluid is delivered through the outlet. After expanding the balloon one or more times, e.g., to the cylindrical shape and/or helical shape, the distal end of the apparatus may be removed from the body lumen and/or entirely from the patient's body with the balloon in the contracted condition.

In accordance with yet another embodiment, a method is provided for treating a body lumen of a patient using a balloon apparatus including an outer member including a first lumen extending between proximal and distal ends thereof, an inner member slidable within the first lumen, and a balloon including a proximal end attached to the outer member distal end, a distal end including an outlet and an interior communicating with the first lumen and the outlet. The distal end of the outer member may be introduced into a body lumen with the balloon in a contracted condition and the inner member in a proximal position such that the outlet is substantially sealed by a sealing member on the inner member distal end. An actuator on a proximal end of the apparatus may be activated to move the inner member to a distal position consequently directing the sealing member distally to open the outlet, and fluid may be delivered through the first lumen such that the fluid passes through the balloon interior and exits the open outlet into the body lumen.

Thereafter, the inner member may be retracted proximally towards the proximal position to substantially seal the outlet with the sealing member. Optionally, a spring element may be provided within the balloon interior that provides sufficient bias to ensure that the sealing member substantially engages the balloon distal end to seal the outlet. Alternatively, the spring element may have sufficient bias such that, when the actuator is released such, the spring element automatically retracts the inner member towards the proximal position to substantially seal the outlet with the sealing member. Fluid may be delivered through the first lumen with the outlet substantially sealed, thereby expanding the balloon from the contracted condition to an enlarged condition, e.g., for dilating a lesion or otherwise treating a body lumen.

Optionally, the balloon may be directed to an expanded helical shape within the body lumen, e.g., before or after expanding the balloon to the enlarged condition, and the balloon may be directed along a wall of the body lumen in the expanded helical shape to remove material from the wall of the body lumen. In one embodiment, the balloon may be directed to the expanded helical shape by expanding the balloon at least partially towards the enlarged condition; expanding a helical member within the balloon interior with the balloon at least partially expanded towards the enlarged condition; and collapsing the balloon around the expanded helical member such that the balloon conforms substantially to the shape of the helical member. In another embodiment, the balloon may be directed to the expanded helical shape by expanding a helical member within the balloon interior with the balloon collapsed such that the balloon conforms substantially to the shape of the helical member. In yet another embodiment, the balloon may be directed to the expanded helical shape by directing the inner member proximally relative to the outer member, thereby compressing the balloon axially and expanding a helical member within the balloon interior, the balloon conforming substantially to the shape of the helical member as the helical member is expanded.

In accordance with still another embodiment, a method is provided for treating a body lumen of a patient using a balloon apparatus including an outer member including a first lumen extending between proximal and distal ends thereof, an inner member slidable within the first lumen, and a balloon including a proximal end attached to the outer member distal end, a distal end including an outlet and an interior communicating with the first lumen and the outlet. The distal end of the outer member may be introduced into a body lumen with the balloon in a contracted condition, and fluid may be delivered through the first lumen with the outlet sealed, thereby expanding the balloon from the contracted condition to an expanded condition. A helical member within the balloon interior may then be expanded with the balloon in the enlarged condition, and then the balloon may be collapsed around the expanded helical member such that the balloon conforms substantially to the shape of the helical member to define an expanded helical shape. The balloon may then be directed along a wall of the body lumen in the expanded helical shape to remove material from the wall of the body lumen.

Optionally, in the expanded helical shape, the size of the helical member and balloon may be varied, as desired. For example, the helical member may be expanded to a size corresponding to the size of the particular body lumen being treated, e.g., by sliding the inner member to one of multiple positions that expands the helical member to the desired size. Thus, the helical member and balloon may be able to treat different size body lumens using a single apparatus.

In accordance with yet another embodiment, a method is provided for treating a body lumen of a patient using an apparatus including an outer tubular member including a first lumen extending between proximal and distal ends thereof, and a balloon including a proximal end attached to the outer member distal end, a distal end including an outlet and an interior communicating with the first lumen and the outlet. Initially, a distal end of an elongate member may be introduced into a patient's body, e.g., via a percutaneous entry site, until the distal end is disposed within a body lumen, the elongate member including a sealing member on the distal end.

The distal end of the outer member may be advanced over the elongate member with the balloon in a contracted condition, e.g., until the balloon outlet engages or is otherwise disposed adjacent the sealing member. Optionally, an actuator on the outer member proximal end may be coupled to the inner member, and the actuator directed to a first position wherein the sealing member substantially seals the outlet. Fluid may then be delivered into the first lumen with the outlet substantially sealed, thereby expanding the balloon to an enlarged condition.

Either before or after expanding the balloon, the actuator may be directed to a second position wherein the sealing member is spaced from the outlet, and fluid may be delivered into the first lumen, thereby delivering the fluid from the outlet into the body lumen. Optionally, once sufficient treatment has been completed, e.g., by expanding the balloon and/or by delivering fluid into the body lumen, the actuator may be decoupled from the inner member, and the outer member removed from around the inner member, e.g., out of the patient's body. Alternatively, the outer and inner members may be removed substantially simultaneously.

In an alternative embodiment, the balloon may be expandable to an expanded helical shape within the body lumen. If so, the balloon may be directed along a wall of the body lumen in the expanded helical shape to remove material from the wall of the body lumen.

In accordance with still another embodiment, a method is provided for treating a body lumen of a patient using an apparatus that includes an outer tubular member including a first lumen extending between proximal and distal ends thereof, a balloon including a proximal end attached to the outer member distal end, a distal end including an outlet and an interior communicating with the first lumen and the outlet, and a helical member within the balloon interior. Initially, a distal end of an elongate member may be introduced into a patient's body until the distal end is disposed within a body lumen, the elongate member including an enlarged member on the distal end.

The distal end of the outer member may be advanced over the elongate member with the balloon in a contracted condition, e.g., until the balloon outlet engages or is otherwise disposed adjacent the sealing member. At least one of the outer member and the inner member may be directed axially relative to the other, e.g., to compress the balloon axially and expand a helical member within the balloon interior. The balloon may conform substantially to the shape of the helical member as the helical member is expanded, e.g., to define an expanded helical shape, and the balloon may be directed along a wall of the body lumen in the expanded helical shape to remove material from the wall of the body lumen.

In accordance with yet another embodiment, a method is provided for treating a body lumen of a patient using a balloon apparatus including an outer member that includes a first lumen extending between proximal and distal ends thereof, an inner member slidable within the first lumen, and a balloon attached to a distal end of the inner member beyond the outer member distal end. The distal end of the outer member may be introduced into a body lumen with the balloon in a contracted condition. The inner member may be in a proximal position such that a sealing member on the inner member substantially seals an outlet in the outer member distal end communicating with the first lumen, or the inner member may be in a distal position such that the sealing member is spaced apart from the outlet.

The inner member may be directed to a distal position, e.g., using an actuator on a proximal end of the outer member, consequently directing the sealing member away from and opening the outlet. Fluid may be delivered through the first lumen such that the fluid passes through the outlet into the body lumen. Optionally, the inner member may be directed to an intermediate position wherein some of the fluid is delivered into the body lumen and some of the fluid passes through one or more passages in the sealing member into the balloon interior to at least partially expand the balloon.

If desired, the inner member may be directed towards the proximal position to substantially seal the outlet with the sealing member, and fluid may be delivered through the first lumen with the outlet substantially sealed, thereby delivering the fluid through the one or more passages in the sealing member to expand the balloon from the contracted condition to an enlarged condition. The balloon may be used to dilate or otherwise treat a body lumen. After sufficient treatment, the fluid may be aspirated from the interior of the balloon through the one or more passages and first lumen to return the balloon to the contracted condition.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIGS. 7A-7H are cross-sections of the balloon of the apparatus of FIG. 7, showing alternate constructions for integrally forming a helical member into the balloon.

FIGS. 10A-10D are cross-sectional views of alternative embodiments of balloon structures that may be provided on the apparatus of FIG. 8 to enhance removal of adherent material within a body lumen.

FIG. 25A is a perspective view of yet another apparatus, similar to that shown in FIG. 7, including a third exemplary embodiment of a handle for actuating the apparatus.

FIG. 25B is a cross-sectional detail of components of a rotary wheel control on the handle of FIG. 25A with a housing of the handle removed to show internal components.

FIG. 26A is a perspective view of still another apparatus, similar to that shown in FIG. 7, including a fourth exemplary embodiment of a handle for actuating the apparatus.

FIG. 26B is a cross-sectional detail of components of a squeeze control on the handle of FIG. 26A with a housing of the handle removed to show internal components.

DETAILED DESCRIPTION OF THE EXEMPLARY EMBODIMENTS

Figure 1:
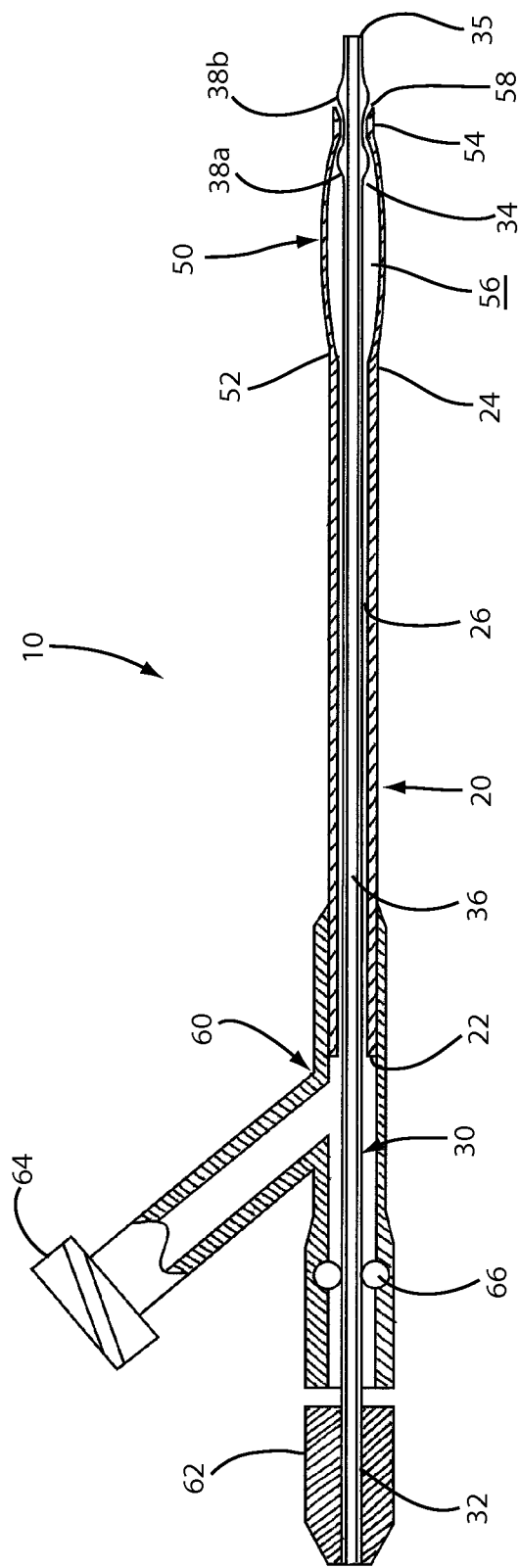
FIG. 1 is a side view of a first exemplary embodiment of an apparatus including a balloon for treating a body lumen, the apparatus operable in a first mode for minimizing a profile of the apparatus for introduction into the body lumen, a second mode for infusing fluid into the body lumen, and a third mode for removing material within the body lumen.
Figure 2A:
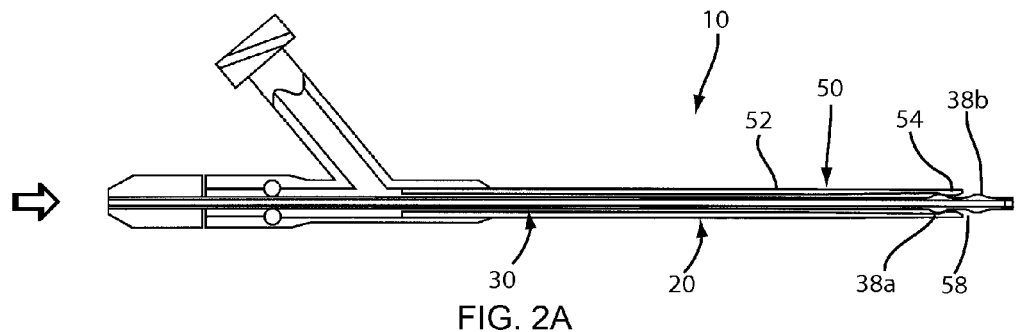
FIG. 2A is a side view of the apparatus of FIG. 1 in the first mode for minimizing a profile of the apparatus for introduction into a body lumen.
Figure 2B:
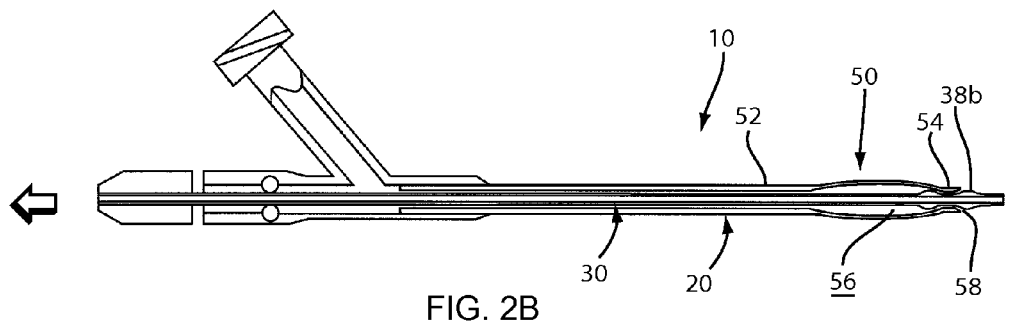
FIG. 2B is a side view of the apparatus of FIG. 1 in the second mode for infusing fluid into a body lumen.
Figure 2C:
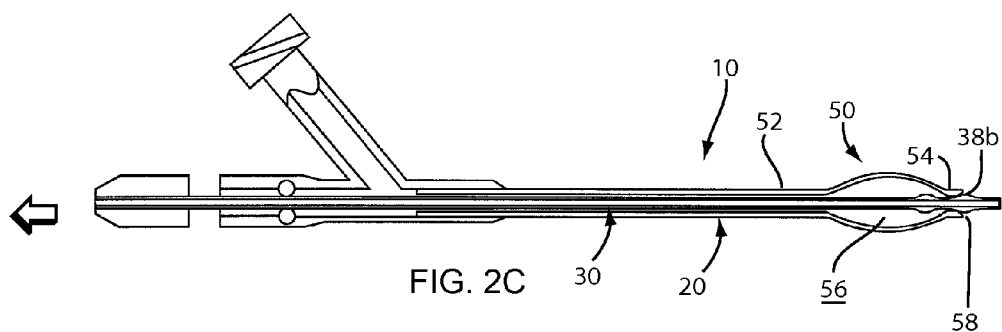
FIG. 2C is a side view of the apparatus of FIG. 1 in the third mode in which the balloon is expanded for removing material within a body lumen.
Figure 2D:
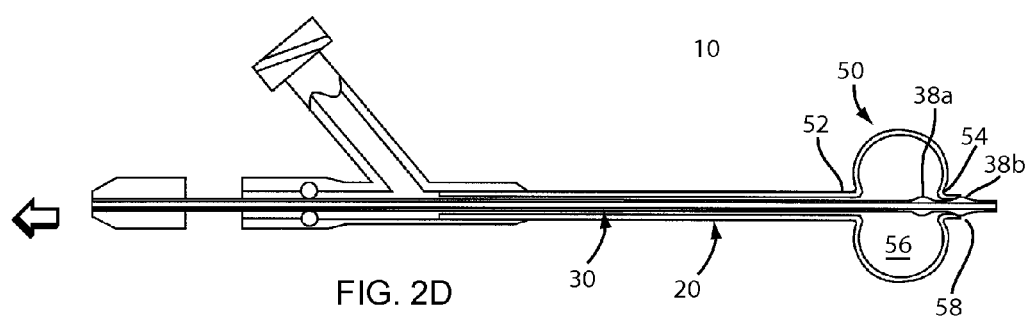
FIG. 2D is a side view of the apparatus of FIGS. 1 and 2C in the third mode, showing a size of the balloon being increased to facilitate removing material within a body lumen.

Turning to the drawings, FIGS. 1-2D show a first exemplary embodiment of an apparatus 10 for treating a body lumen, e.g., for infusing fluid into a body lumen and/or for removing thrombus, objects, and/or obstructive material from within a body lumen, such as a blood vessel, aorto-venous fistula, tubular graft, and the like (not shown). Generally, the apparatus 10 includes a catheter, sheath, or other tubular outer member 20, a core wire, shaft, or other elongate inner member 30, and an expandable balloon 50 carried by the inner and/or outer members 20, 30. The apparatus 10 may be operable in multiple modes, for example, to perform various treatments or other functions within a body lumen, e.g., to reduce or eliminate the need to exchange multiple devices during a procedure within a body lumen. For example, the apparatus 10 may be operable in a first mode for minimizing a profile of the apparatus 10, e.g., to facilitate introduction into a patient's body (FIG. 2A), a second mode for infusing fluid into a body lumen (FIG. 2B), and a third mode for removing material within a body lumen (FIGS. 2C and 2D), as described further below.

As best seen in FIG. 1, the outer member 20 includes a proximal end 22, a distal end 24 sized for introduction into a body lumen, and a first lumen 26 extending therebetween. The outer member 20 may have a substantially uniform construction along its length, or alternatively, the construction may be varied. For example, a proximal portion of the outer member 20 may be substantially rigid or semi-rigid to facilitate advancement of the apparatus 10 from the proximal end 22 and/or a distal portion of the outer member 20 may be flexible, e.g., to facilitate bending and/or advancement through tortuous anatomy without substantial risk of kinking or buckling. In exemplary embodiments, the outer member 20 may be formed from materials such as metal, plastic, e.g., PEEK, Grilamed L25, and the like, or composite materials. The outer member 20 may have a length between about thirty and one hundred thirty centimeters (30-130 cm) and an outer diameter between about 1.2 and 2.0 millimeters, and the first lumen 26 may have a diameter between about 1.0 and 1.8 millimeters.

The inner member 30 also includes a proximal end 32, a distal end 34, and, optionally, may include a second lumen 36 extending between the proximal and distal ends 32, 34, which may be sized to slidably receive a guidewire, or other rail (not shown) therethrough, e.g., having a diameter between about 0.3 and 1.0 millimeter. The inner member 30 is sized to be slidably received within the first lumen 26 of the outer member 20, e.g., such that an annular space is defined between the outer and inner members 20, 30 for passing one or more fluids therethrough, as described further below. The inner member 30 may have a length relative to the outer member 20 such that the inner member proximal end 32 is received within or extends proximally beyond the outer member proximal end 22 and the inner member distal end 34 extends distally beyond the outer member distal end 24, e.g., through the balloon 50, as described further below.

The balloon 50 includes a proximal end 52 coupled to the outer member distal end 24, a distal end 54 defining an outlet 58, and an interior 56 communicating with the first lumen 26 and the outlet 58. The proximal end 52 of the balloon 50 may be attached or otherwise secured to the distal end 24 of the outer member 20 to provide a fluid-tight connection, e.g., by one or more of bonding with adhesive, interference fit, sonic welding, fusing, engagement with a surrounding sleeve or other connector (not shown), and the like.

The distal end 34 of the inner member 30 may extend through the distal end 54 of the balloon 50, e.g., such that the outlet 58 defines an annular passage between the distal end 54 of the balloon 50 and the distal end 34 of the inner member 30. The size of the outlet 58 may be substantially the same as the size of the first lumen 26, or alternatively, the outlet 58 may be larger or smaller than the first lumen 26, as desired, depending on the desired degree of friction or resistance to fluid flow through the outlet 58. For example, with the outlet 58 open to allow fluid flow, the resistance to fluid flowing through the outlet 58 may be substantially less than the resistance of the balloon 50 to expansion, such that the fluid preferentially flows through the outlet 58, rather than expanding the balloon 50, as described further below.

Figure 27A:
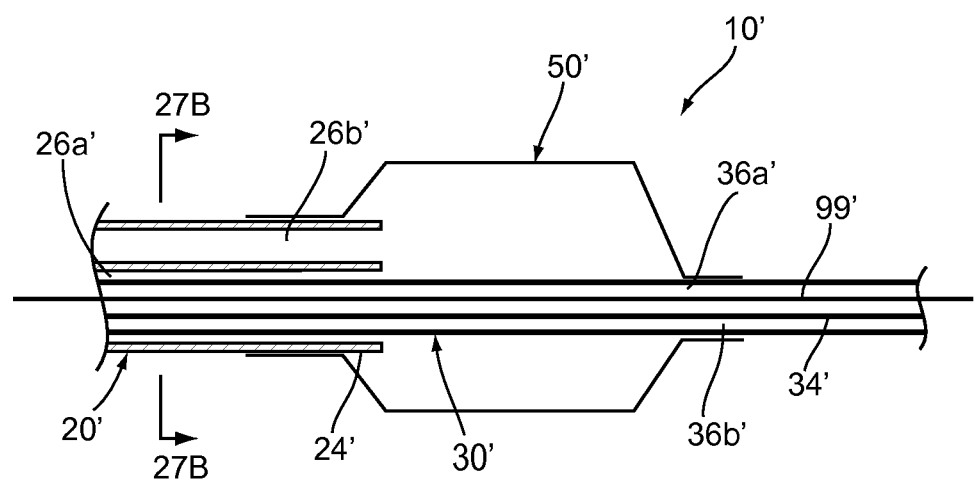
FIG. 27A is a cross-sectional side view of a distal end of another embodiment of an apparatus including a balloon for treating a body lumen.
Figure 27B:
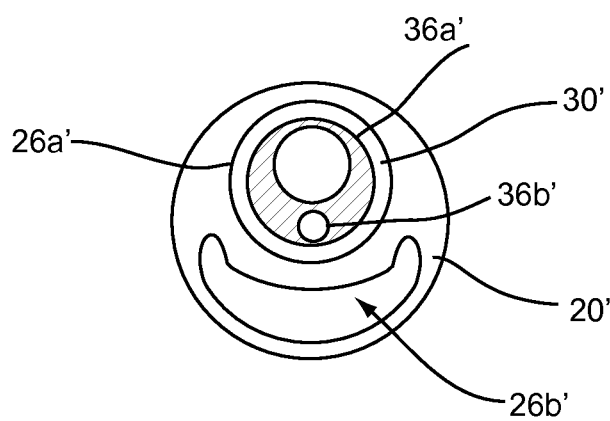
FIG. 27B is a cross-sectional view of the apparatus of FIG. 27A taken along line 27B-27B.

Alternatively, as shown in FIGS. 27A and 27B, an apparatus 10' may be provided that includes an outer member 20' and/or an inner member 30' that include multiple lumens. For example, as best seen in FIG. 27B, the outer member 20' may include a first lumen 26a' for slidably receiving the inner member 30' and a separate inflation lumen 26b' for delivering fluid into the interior 56' of the balloon 50.' This alternative may allow a profile of the outer member 20' to be reduced since less clearance may be needed around the inner member 30' in the first lumen 26a.' In addition or alternatively, the inner member 30' may include a first instrument lumen 36a' for receiving a guidewire 99' or other instrument, and a second fluid lumen 36b' for delivering and/or aspirating fluid beyond the distal end 34' of the inner member 30.'

Returning to FIG. 1, the distal end 54 of the balloon 50 may be integrally formed with the main wall of the balloon 50 (defining the interior 56), and, optionally the proximal end 52 of the balloon 50. For example, the balloon 50 and its proximal and distal ends 52, 54 may be molded, blown, or otherwise formed from a single tubular section of material. Optionally, the main wall of the balloon 50 may be relatively thin compared to the distal end 54, e.g., such that the distal end 54 of the balloon 50 maintains its original size and/or shape as the balloon 50 is expanded.

For example, the distal end 54 of the balloon 50 may be sufficiently thick and/or rigid to provide a sealing ring on the distal end 54. Optionally, the distal end 54 of the balloon 50 may include one or more additional features, e.g., surrounding or otherwise defining the outlet 58 and/or reinforcing the distal end 54. For example, the distal end 54 may include a collar or sleeve (not shown, see, e.g., sleeve 155 shown in FIG. 7), within or around the distal end 54, e.g., attached or otherwise secured to the distal end 54, e.g., by bonding with adhesive, interference fit, sonic welding, fusing, and the like.

The balloon 50 may be formed from elastic material, e.g., to provide a compliant or semi-compliant balloon that may be expanded to a variety of sizes and/or shapes, e.g., based on the amount of fluid and/or pressure within the interior 54 of the balloon 50 and/or the relative position of the inner member 30, as described further below. Alternatively, the balloon 50 may be formed from substantially inelastic material, e.g., to provide a non-compliant balloon that expands to a predetermined size when inflated independent of pressure (once a minimum volume and/or pressure is introduced to achieve the predetermined size). Such a non-compliant balloon 50 may expand to the predetermined size even if inflated to relatively high pressures, e.g., until the balloon 50 bursts or otherwise ruptures, e.g., at pressures of at least ten atmospheres, twenty atmospheres, thirty atmospheres, and the like.

One or more sealing members 38 may be carried on the inner member distal end 34, e.g., such that the sealing member(s) 38 are movable relative to the balloon 50 as the inner member 30 is moved, e.g., for selectively opening and closing the outlet 58 of the balloon 50 to provide a valve, as described further below. The sealing member(s) 38 may be formed from flexible materials, e.g., which may enhance engagement with the balloon distal end 54, such as elastomeric materials, e.g., silicone, or other plastics, e.g., PEBAX.

As best seen in FIG. 1, a first sealing member 38a may be provided on the inner member 30 proximal to or otherwise adjacent a second sealing member 38b. The sealing member(s) 38 may be disposed adjacent a distal tip 35 of the inner member 30 or may extend beyond the distal tip 35. The distal tip 35 (or the sealing member extending beyond the distal tip 35) may be substantially atraumatic, e.g., rounded, softened, provided with a "J" tip, and the like (not shown), to facilitate advancement of the apparatus 10 within a patient's body without substantial risk of the distal tip 35 puncturing or otherwise damaging walls of body lumens through which the distal tip 35 passes.

The sealing member(s) 38 may have a size, e.g., outer diameter, that is larger than the distal end 54 of the balloon 50, e.g., larger than the inner diameter of the outlet 58. As shown in FIG. 1, the sealing members 38 are spaced apart sufficiently from one another such that the distal end 54 of the balloon 50 is free floating between the sealing members 38. When the inner member 30 is directed axially, one of the sealing members 38 may engage or otherwise contact the distal end 54 of the balloon 50. The sealing member(s) 38 may have tapered shapes to facilitate seating or other engagement by the sealing member(s) 38 with the distal end 54.

For example, with additional reference to FIG. 2A, the inner member 30 may be directed distally to a first or distal position wherein the first sealing member 38a pushes or otherwise contacts the distal end 54, and the second sealing member 38b is spaced from the balloon outlet 58. As shown, the inner member 30 may be advanced distally to cause the first sealing member 38a to push the distal end 54. Because the outer diameter of the first sealing member 38a is larger than inner diameter of the distal end 54, the first sealing member 38a pushes the distal end 54 of the balloon 50 away from the proximal end 52 tie, thereby stretching the balloon 50. This configuration may minimize or otherwise reduce the profile of the balloon 50, e.g., to facilitate introduction into a patient's body. In this first position, the first sealing member 38a may substantially seal the outlet 58, although alternatively, the first sealing member 38a may include one or more axial grooves or other features that allow at least some fluid to pass through the outlet 58 even when the first sealing member 38a is seated or pushing against the distal end 54.

Turning to FIG. 2B, the inner member 30 may be directed axially to a second position, e.g., proximal to the first position, such that the distal end 54 of the balloon 50 is disposed between the sealing members 38a, 38b and the outlet 58 is substantially open. Thus, fluid introduced through the first lumen 26 of the outer member 20 may pass through the balloon interior 56 and exit through the outlet 58, e.g., between the balloon distal end 54 and inner member distal end 24 into the body lumen beyond the distal tip 35.

As shown in FIG. 2C, the inner member 30 may also be directed proximally to a third position, e.g., proximal to the second position, in which the second sealing member 38b engages the distal end 54 of the balloon 50, thereby substantially sealing the outlet 58 from fluid flow therethrough. Thus, any fluid introduced through the first lumen 26 enters the balloon interior 56 and expands the balloon 50. Optionally, as shown in FIG. 2D, once the balloon 50 is expanded, the inner member 30 may be directed further proximally, e.g., to an indefinite number of positions wherein the second sealing member 38b continues to seal the outlet 58, and the size and/or shape of the expanded balloon 50 may be changed. For example, as shown in FIG. 2C, with the inner member 30 in the third position, the balloon 50 may be inflated to an elliptical or generally spherical shape, e.g., by delivering a predetermined volume of fluid into the interior 56 of the balloon 50. If the balloon 50 is compliant, one of a range of desired volumes may be delivered into the interior 56 to expand the balloon 50 to a desired diameter.

With further reference to FIG. 2D, thereafter, as the inner member 30 is directed proximally further, the distal end 54 of the balloon 50 (captured between the sealing members 38) is also directed proximally, i.e., towards the proximal end 52 of the balloon 50, thereby compressing the balloon 50 axially and expanding the balloon 50 further.

Figure 6A:
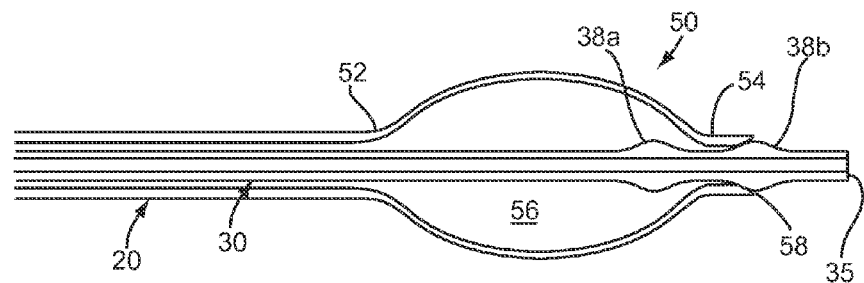
FIGS. 6A-6D are side view details of the apparatus of FIGS. 1 and 3, showing alternative configurations for the balloon.

As shown in FIG. 6A, the balloon 50 wall may have a substantially uniform wall thickness between the proximal and distal ends 52, 54. Thus, when the balloon is compressed, as shown in FIG. 2D, the proximal and/or distal ends 52, 54 of the balloon 50 may at least partially evert into the interior 56 of the balloon 50. Thus, the wall of the balloon 50 may fold over onto the outside of the proximal and/or distal ends 52, 54 as the inner member 30 is directed proximally from the third position.

Figure 6B:
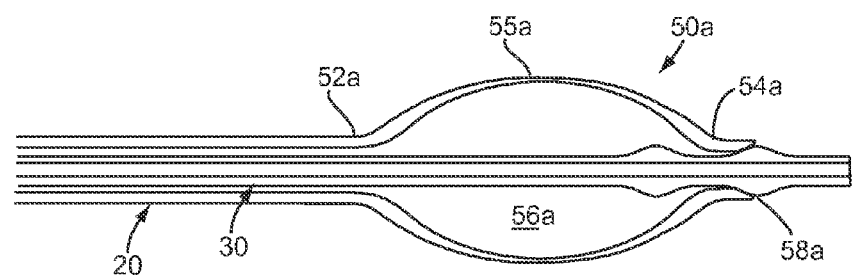

Alternatively, as shown in FIG. 6B, the thickness of the balloon 50a may be reduced along its length, e.g., thinning from the proximal and distal ends 52a, 54a towards a central region 55a of the balloon 50a. Thus, the regions of the balloon 50a immediately adjacent the proximal and distal ends 52a, 54a may be relatively rigid compared to the central region 55a. When the balloon 50a is compressed after expansion, the regions immediately adjacent the proximal and distal ends 52a, 54a may resist the balloon 50a everting and the thinner central region 55a may expand to a greater diameter compared to the balloon 50 of FIG. 6A.

Figure 6C:
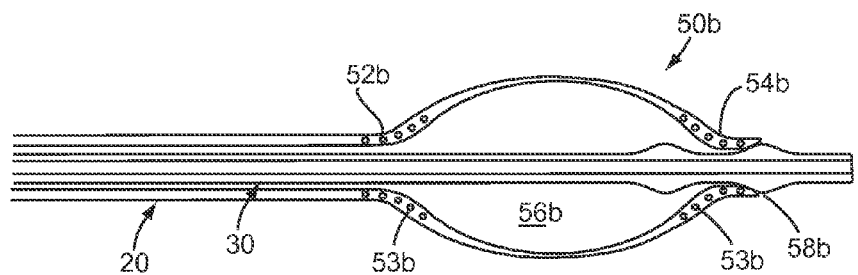
Figure 6D:
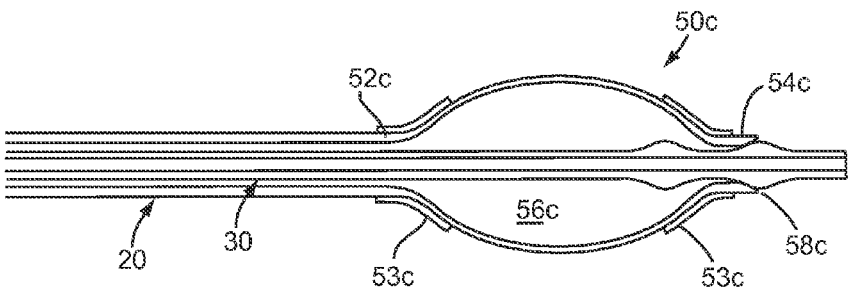

In further alternatives, shown in FIGS. 6C and 6D, the regions of the balloon 50b, 50c immediately adjacent the proximal and/or distal ends 52,b 54b or 52c, 54c may be reinforced further, e.g., including additional materials, to reinforce the base of the balloon 50b, 50c to reduce everting and/or otherwise preferentially control expansion of the balloon 50b, 50c. For example, in FIG. 6C, composite materials 53b have been embedded or otherwise provided in the balloon material adjacent the proximal and distal ends 52b, 54b, while in FIG. 6D, an additional layer of material 53c has been added, which may be the same material or different material than the rest of the balloon 50c. The layer may be attached to the balloon 50c, e.g., similar to the materials and methods described elsewhere herein for attaching the balloon 50c to the outer member 20.

Returning to FIG. 1, a handle or hub 60 may be coupled to or otherwise provided on the proximal end 22 of the outer member 20, e.g., for manipulating the outer member 20 and/or the entire apparatus 10. The handle 60 may have an ergonomic shape, e.g., to facilitate holding and/or manipulating the handle 60, and including one or more controls or actuators for actuating the components of the apparatus 10. For example, as shown, a pull handle 62 may be provided adjacent the main handle 60 that is coupled to the inner member 30. Thus, to move the inner member 30 to the various positions described above, the pull handle 62 may be pushed or pulled, e.g., pushed distally to direct the inner member 30 to the first position shown in FIG. 2A, and pulled proximally to direct the inner member 30 to the second and third (or further proximal) positions, shown in FIGS. 2B-2D. Alternatively, similar to the embodiments shown in FIGS. 11 and 14, a slider actuator (not shown) may be provided on the handle 60 that is coupled to the inner member 30 for directing the inner member 30 axially relative to the handle 60 and outer member 20. In a further alternative, a wheel or other actuator may be provided for directing the inner member 30 axially relative to the outer member 20.

The pull handle 62 and/or inner member 30 may be biased to one of the positions shown in FIGS. 2A-2D, e.g., by one or more springs or other biasing mechanisms (not shown) within the handle 60. For example, the inner member 30 may be biased to the second (infusion) position, but may be directed to the other positions by overcoming the bias. Alternatively, the handle 60 may include one or more features, e.g., pockets, notches, and the like (not shown), providing tactile feedback and/or for releasably securing the inner member 30 in one of the positions. In addition or alternatively, the handle 60 may include one or more visual markers (not shown), e.g., to inform the user when the various positions are achieved. In a further alternative, the first sealing member 38a may be eliminated and the first position eliminated, e.g., if there is less concern with profile of the apparatus 10 during introduction and/or to simplify operation of the apparatus 10.

With continued reference to FIG. 1, the handle 60 may also include one or more ports for coupling one or more fluid sources to the apparatus 10, such as a source of inflation media, a source of vacuum, and/or a source of diagnostic and/or therapeutic agents (not shown). For example, as shown, a side port 64 may communicate with the first lumen 26. The side port 64 may include one or more connectors (not shown) to facilitate coupling one or more sources of fluid to the side port 64, e.g., a Luer lock connector, and/or one or more seals, e.g., a hemostatic seal, to prevent fluid from leaking from the side port 64.

A syringe or other source of fluid (not shown) may be coupled to the side port 64 to allow delivery of the fluid through the first lumen 26 into the interior 56 of the balloon 50 and/or through the outlet 58, depending upon the position of the inner member. For example, if the inner member 30 is in the second (infusion) position, contrast material, e.g., radiopaque, echogenic, or other fluid that facilitates observation using fluoroscopy, ultrasound, or other external imaging, may be delivered through the first lumen 26 and outlet 58 into a body lumen. Such material may facilitate monitoring the apparatus 10 during advancement through a patient's body into a target body lumen and/or to identify the status of treatment of a body lumen, as described further below. With the inner member 30 in the third position, the same fluid may be delivered through the first lumen 26 to expand the balloon 50, or the source of contrast material may be replaced with a source of a different fluid, e.g., a syringe of saline, to facilitate expansion and/or collapse of the balloon 50.

Alternatively, multiple ports may be provided that communicate with the first lumen 26, e.g., such that various fluids may be delivered selectively through the first lumen 26 depending upon the desired function. For example, a source of contrast and a source of saline could be coupled to different ports such that each fluid may be delivered independently depending upon the position of the inner member 30 without having to change out the sources. Alternatively, a source of one or more therapeutic agents may be coupled to the side port 64 (or to a separate port), e.g., when desired, to deliver the agent(s) into the target body lumen.

Optionally, the handle 60 may include one or more seals, bushings, and the like to facilitate relative motion of the outer and inner members 20, 30 and/or to seal the first lumen 26. For example, as shown in FIG. 1, an o-ring 66 may be provided between the outer and inner members 20, 30, which may guide the inner member 30 as it moves axially relative to the outer member 30 and handle 60. The o-ring 66 may also be located proximal to the side port 64, thereby providing a substantially fluid-tight seal between the outer and inner members 20, 30 to prevent leakage of fluid introduced into the side port 64 from the handle 60.

As shown, the pull handle 62 includes a port 63 for receiving a guidewire or other rail (not shown) therethrough. For example, a guidewire may be introduced into the second lumen 36 of the inner member 30, e.g., from the port 63 or by backloading into the inner member distal end 34. The port 63 may include one or more seals, e.g., a hemostatic seal (not shown), to accommodate passage of a guidewire therethrough without risk of substantial risk of leakage of blood or other body fluids from the second lumen 36.

Optionally, the outer member 20 may include one or more additional lumens (not shown) extending between the proximal and distal ends 22, 24, e.g., a guidewire lumen for receiving a guidewire or other rail (not shown), e.g., if the inner member 30 does not include the second lumen 36, an inflation lumen for delivering inflation media to another balloon (not shown) on the distal end 24, and the like.

In addition or alternatively, if desired, the apparatus 10 may include one or more markers to facilitate positioning and/or advancement of the apparatus 10 during use. For example, one or more radiopaque markers may be provided on the outer member distal end 24, on the inner member 30 within or adjacent the balloon 50 or distal tip 35, on the balloon 50, e.g., on the proximal and/or distal ends 52, 54, and/or on the sealing member(s) 38. Alternatively, one or more components of the apparatus 10 may be formed from radiopaque or other materials that may facilitate imaging the apparatus 10 during use. For example, radiopaque markers and/or materials may facilitate positioning or otherwise imaging the apparatus 10 using fluoroscopy or other x-ray imaging, e.g., when positioning the balloon 50 (either before or after expansion) and/or when infusing fluid via the outlet 48. Alternatively, echogenic markers and/or materials may be provided to facilitate imaging using ultrasound or similar imaging techniques.

With continued reference to FIGS. 2A-2D, an exemplary method will now be described for treating a body lumen (not shown), e.g., using an apparatus 10, which may be any of the embodiments described herein, and not necessarily limited to the embodiment shown and described below with reference to FIG. 1. The target body lumen may be a blood vessel, e.g., a vein or artery, a graft, e.g., an aorto-venous fistula, tubular xenograft, or synthetic tubular graft, and the like. For example, the body lumen may be a passage communicating between an adjacent artery and vein (not shown), e.g., in an arm or other region of a dialysis patient. Alternatively, the body lumen may be a blood vessel within a patient's vasculature, e.g., a peripheral vessel in a patient's leg, a cerebral vessel, and the like. In a further alternative, the material may be a stone within a patient's urinary tract or other foreign object to be removed from the patient's body.

Optionally, the body lumen may be accessed using one or more additional instruments (not shown), which may be part of a system or kit including the apparatus 10. For example, an introducer sheath, guide catheter, or other tubular member (not shown) may be introduced adjacent the target site where the material is to be removed, or may be introduced elsewhere in the patient's body to provide access to the patient's vasculature or other passages communicating with the body lumen. If the body lumen is located in a peripheral vessel of the patient, a percutaneous puncture or cut-down may be created using a needle or other instrument (not shown) at a peripheral location, such as a femoral artery, carotid artery, or other entry site (also not shown), and an introducer sheath may be placed through the puncture at the peripheral location to provide access. The apparatus 10 may be advanced through the patient's vasculature from the entry site, e.g., alone or with the aid of a guide catheter, guidewire, and the like (not shown).

For example, to facilitate directing the apparatus 10 from an entry site to the target body lumen, a guide catheter, microcatheter, or other tubular body may be placed from the entry site to the body lumen using conventional methods. In addition or alternatively, a guidewire (not shown) may be placed from the entry site to the body lumen if desired, e.g., if the inner member 30 includes the second lumen 36. The tubular body may also be used for aspiration, e.g., coupled to a source of vacuum for capturing material removed by the apparatus 10.

Initially, with reference to FIG. 2A, the apparatus 10 may be advanced into the body lumen with the inner member 30 in the second or distal position, e.g., such that the balloon 50 is stretched to reduce its profile. Optionally, if the first sealing member 38a does not seal the outlet 58, one or more fluids may be delivered into the body lumen, e.g., to facilitate imaging and/or positioning the apparatus 10. Alternatively, the inner member 30 may be directed to the first position, shown in FIG. 2B, and fluid delivered to facilitate imaging.

For example, radiopaque contrast or other fluid may be delivered into the body lumen via the annular passage defined by the first lumen 26 between the outer and inner members 20, 30 to facilitate locating and/or measuring the size of the material 92 using fluoroscopy. Markers (not shown) on the apparatus 10 may facilitate positioning the balloon 50 relative to material intended to be removed before the balloon 50 is expanded, e.g., to facilitate verifying that the balloon 50 is positioned distal to or otherwise beyond the material. If desired, the inner member 30 may be directed back and forth between the first and second positions, e.g., to allow infusion of contrast and to reduce the profile of the apparatus 10 to facilitate further advancement, e.g., until the balloon 50 is located beyond obstructive material targeted for removal.

Optionally, the apparatus 10 may be introduced through a guide catheter or other tubular member (not shown), that includes a lumen communicating with a source of vacuum. With the balloon 50 disposed beyond the guide catheter but not yet expanded, the source of vacuum may be activated to aspirate material within the body lumen during the subsequent treatment.

Turning to FIG. 2C, the inner member 30 may be directed to the third position, thereby sealing the outlet 58, and the balloon 50 may be inflated within the body lumen, e.g., such that the balloon 50 extends substantially entirely across the body lumen. The entire apparatus 10 may then be retracted to pull the occlusive material from the body lumen, e.g., to be aspirated into the guide catheter, or otherwise removed from the body lumen. As shown in FIG. 2D, if desired, the inner member 30 may be pulled to further expand the balloon 50, e.g., to substantially engage the wall of the body lumen. The additional pressure from the balloon 50 may facilitate separating adherent material from the wall of the body lumen and allow its removal.

Once material is removed, the inner member 30 may be directed back towards the second position, and fluid introduced to observe the amount of material removed and/or remaining within the body lumen. If additional material is to be removed, the inner member may be directed to the first position, e.g., if desired to advance the apparatus 10 through additional material to be removed. Once the balloon 50 is located beyond the material, the process may be repeated as often as desired.

If desired, the obstructive material may be treated, e.g., at least partially dissolved, macerated, and the like before, during, or after withdrawal. For example, a therapeutic agent may be delivered into the body lumen via the first lumen 26 of the outer member 20, e.g., to at least partially dissolve or separate thrombus or other relatively soft material before being removed by the balloon 50 and/or otherwise to treat the wall of the body lumen.

Because a single lumen, i.e., the first lumen 26, is used for both inflation of the balloon 50 and delivering fluid into the body lumen, the profile of the outer member 20 and therefore of the overall apparatus 10 may be smaller than devices that include separate inflation and infusion lumens. Further, although the second lumen 36 of the inner member 30 could be used for infusion of fluids, this would generally require removing the guidewire over which the apparatus 10 is introduced since the guidewire may substantially fill the second lumen 36. Because the first lumen 26 may be used for infusion, the guidewire may remain within the second lumen 36 throughout the procedure, thereby potentially reducing the number of guidewire or other device exchanges. Further, the apparatus 10 may remain over the guidewire, which may facilitate advancing the apparatus 10 to other target body lumens intended for treatment.

Figure 36:
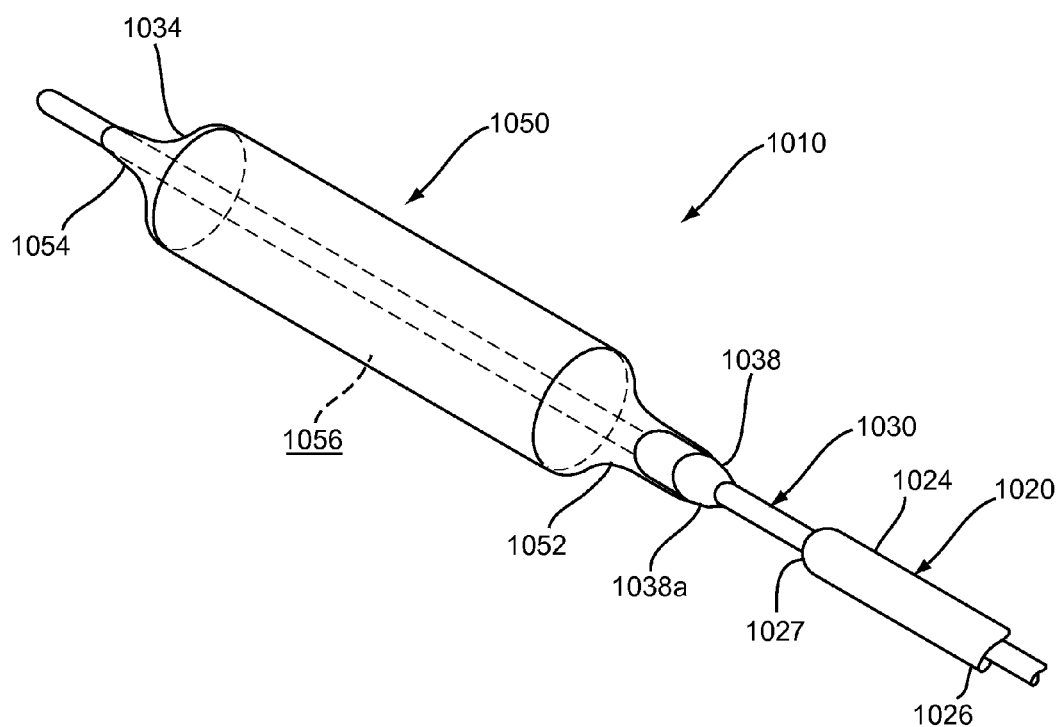
FIG. 36 is a perspective view of a distal end of still another exemplary embodiment of an apparatus for treating a body lumen.

In various alternatives, the valve created by the sealing member(s) 38 and the outlet 58 of the balloon 50 may be provided at other locations on the apparatus 10, if desired. For example, the configuration may be reversed such that the outlet 58 and sealing members 38 may be located proximal to the balloon 50. For example, a sealing member (not shown) may be provided on the distal end 24 of the outer member 20, and the proximal end 52 of the balloon 50 may float adjacent the sealing member(s), with the distal end 54 of the balloon 50 is secured to the distal end 34 of the inner member 30 (also not shown). Thus, movement of the inner member 30 relative to the outer member 20 may cause the balloon proximal end to selectively engage or disengage the sealing member(s), allowing infusion from the first lumen 24 when the balloon proximal end is not engaged with the sealing member(s) and allowing balloon inflation when the balloon proximal end engages the sealing member(s). Alternatively, as shown in FIGS. 36-37C, an outlet 1027 may be provided on the distal end 1024 of the outer member 1020 that may be selectively engaged with a sealing member 1038 on the inner member 1030 proximal to the balloon 1050, as described further below.

In another alternative, a balloon (not shown) may be provided on the distal end 24 of the outer member 20 proximal to the balloon 50 and/or on the distal end 34 of the inner member 30 distal to the balloon 50, if desired, similar to other embodiments described herein. Such a balloon may be a non-compliant, high pressure balloon, e.g., for dilating the body lumen, or an elastic, compliant balloon for substantially sealing the body lumen to isolate one or more regions of the body lumen before infusion of fluid therein.

Figure 3:
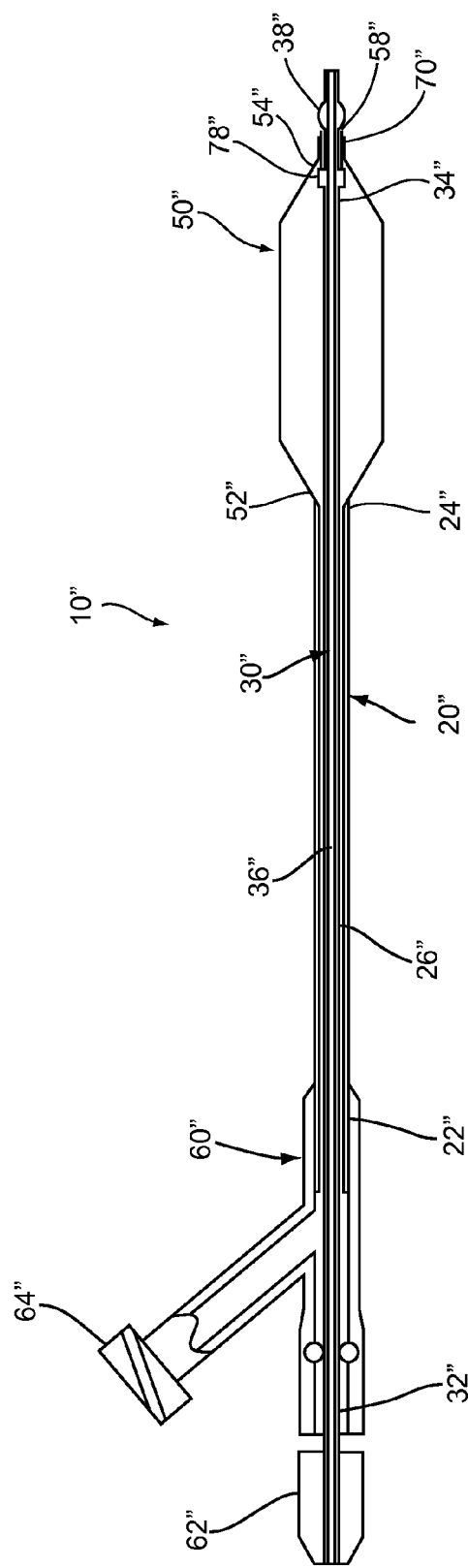
FIG. 3 is a side view of another embodiment of an apparatus including a balloon for treating a body lumen and a valve for selectively delivering fluid from the apparatus.
Figure 4A:
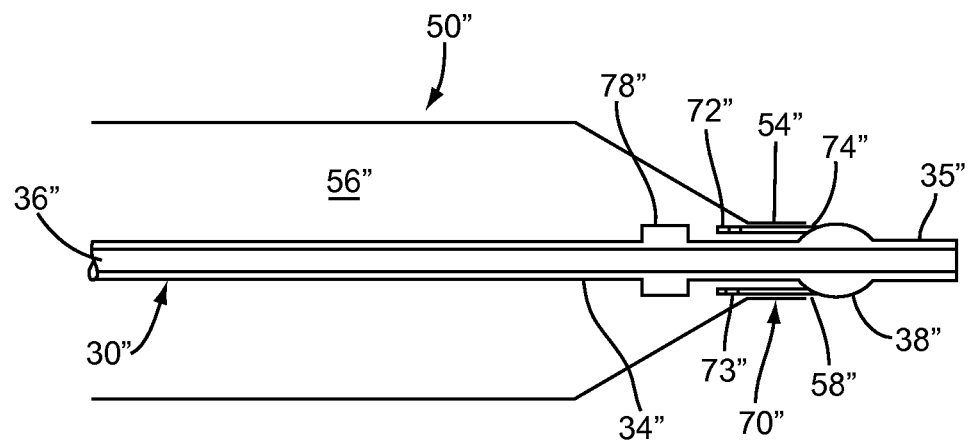
FIGS. 4A and 4B are details of a distal end of the apparatus of FIG. 3 showing the valve in closed and open positions, respectively.
Figure 4B:
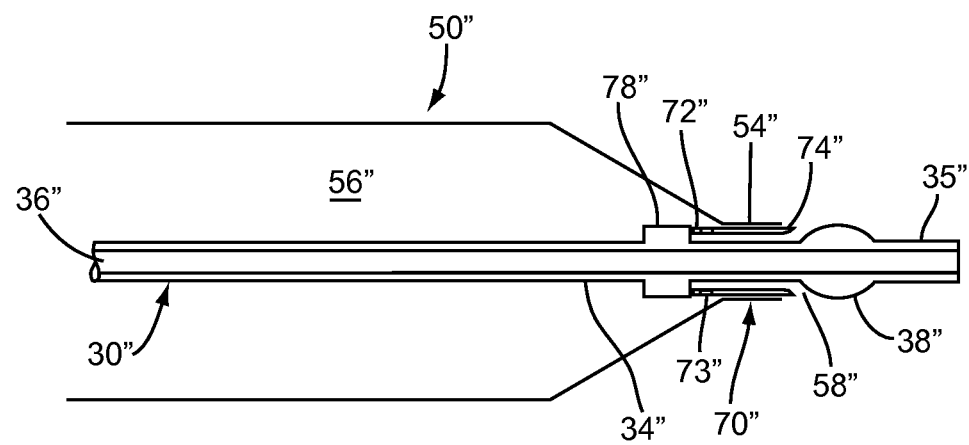

Turning to FIGS. 3-4B, another embodiment of an apparatus 10" is shown for treating a body lumen that includes an outer tubular member 20," an inner member 30," and an expandable balloon 50" carried by the inner and/or outer members 20," 30," which may be constructed similar to the apparatus 10 of FIG. 1. Also similar to the previous embodiments, the apparatus 10" may be operable in multiple modes, for example, a first mode for expanding the balloon 50" (FIG. 4A), e.g., to remove material, dilate, or otherwise treat a body lumen, and a second mode for delivering fluid into a body lumen (FIG. 4B), as described further below.

As best seen in FIG. 3, the outer member 20" includes a proximal end 22," a distal end 24" sized for introduction into a body lumen, and a first lumen 26" extending therebetween. The inner member 30" also includes a proximal end 32," a distal end 34," and, optionally, may include a second lumen 36" extending between the proximal and distal ends 32," 34," which may be sized to slidably receive a guide wire or other instrument (not shown) therethrough. The balloon 50" includes a proximal end 52" coupled to the outer member distal end 24," a distal end 54" including an outlet 58," and an interior 56" communicating with the first lumen 26" and the outlet 58." The distal end 54" of the balloon 50" may be integrally formed with the main wall of the balloon 50" (defining the interior 56"), and, optionally the proximal end 52" of the balloon 50." The balloon 50" may be formed from elastic material, e.g., to provide a compliant or semi-compliant balloon, or from substantially inelastic material, e.g., to provide a non-compliant balloon, similar to other embodiments herein.

As best seen in FIGS. 4A and 4B, a sleeve 70" may be attached to or otherwise provided on the distal end 54" of the balloon 50," e.g., for surrounding or otherwise defining the outlet 58" and/or reinforcing the distal end 54." For example, the sleeve 70" may be a length of substantially rigid tubing or other tubular body attached to the inner surface of the distal end 54". The distal end 34" of the inner member 30" may extend through the sleeve 70," e.g., such that the outlet 58" defines an annular passage between the sleeve 70" and the distal end 34" of the inner member 30."

As shown, the sleeve 70" is longer than the distal end 54" such that a first end 72" of the sleeve 70" extends proximally from the distal end 54" into the interior 56" of the balloon 50" and a second end 74" of the sleeve 70" extends distally from the distal end 54" to define the outlet 58." The first end 72" of the sleeve 70" includes one or more holes or other apertures 73" (two shown) in a side wall thereof, e.g., to provide a fluid passage into the sleeve 70" as described further below.

A sealing member 38" may be carried on the inner member distal end 34," e.g., such that the sealing member 38" is movable relative to the balloon 50" as the inner member 30" is moved, e.g., for selectively opening and closing the outlet 58" to provide a valve, as described further below. For example, the sealing member 38" may have a size, e.g., outer diameter, that is larger than the inner diameter of the sleeve 70" and/or the outlet 58." Optionally, the sealing member 38" may have a tapered shape, e.g., to facilitate seating or other engagement by the sealing member 38" with the outlet 58." In addition or alternatively, the second end 74" of the sleeve 70" may have a tapered shape, e.g., to facilitate and/or enhance seating and/or sealing the outlet 58" with the sealing member 38."

The sealing member 38" may be formed from flexible material, e.g., which may enhance engagement with the second end 74" of the sleeve 70," similar to other embodiments herein. Optionally, the sealing member 38" (or the inner member 30") may include a substantially atraumatic distal tip 35," e.g., a rounded, softened, beveled, or "J" or other curved tip, (not shown), similar to other embodiments herein.

In addition, a stop 78" may be provided on the inner member distal end 34" for limiting distal movement of the inner member 30" relative to the distal end 54" of the balloon 50." As best seen in FIGS. 4A and 4B, the stop 78" may be attached to the inner member distal end 34" at a location spaced apart from the sealing member 38" such that a distance between the stop 78" and the sealing member 38" is longer than the length of the sleeve 70." Thus, the distal end 54" of the balloon 50" may be free floating between the sealing member 38" and the stop 78" to provide a valve for selectively opening and closing the outlet 58," similar to other embodiments herein.

For example, as shown in FIG. 4A, the inner member 30" may be directed proximally to direct the sealing member 38" into engagement with the second end 74" of the sleeve 70" to substantially seal the outlet 58." The sealing member 38" and/or sleeve 74" may be sufficiently flexible to contact one another with a relatively high contact pressure, e.g., by deformation of one or both of the sealing member 38" and/or sleeve 74," to provide a substantially fluid-tight seal. Thus, in this position, fluid delivered into the first lumen 26" of the outer member 20" may remain within the balloon interior 56" to expand the balloon 50."

Turning to FIG. 4B, the inner member 30" may be directed distally, e.g., until the stop 78" contacts the sleeve 70," thereby opening the outlet 58." Thus, fluid delivered into the first lumen 26" passes through the balloon interior 56" and through the sleeve 70" and outlet 58" into the body lumen beyond the apparatus 10." As shown, the stop 78" and sleeve 70" may have substantially flat and/or blunt end surfaces that contact one another, e.g., to provide a relatively low contact pressure between the stop 78" and sleeve 70." The hole(s) 73" ensure that fluid delivered through the balloon interior 56" enters the sleeve 70" and exits the outlet 58," e.g., if a restriction or seal results between the contacting end surfaces of the stop 78" and sleeve 70."

In one embodiment, fluid may be delivered from the outlet 58" with minimal or no expansion of the balloon 50." Alternatively, the size of the holes 73" may be selected such that some friction results when fluid is delivered therethrough such that the balloon 50" expands at least partially while still delivering fluid through the outlet 58" into the body lumen.

Optionally, the inner member 30" may be advanced to press the stop 78" against the sleeve 70" and push the distal end 54" of the balloon 50" away from the proximal end (not shown), thereby stretching the balloon 50." This configuration may minimize or otherwise reduce the profile of the balloon 50," e.g., to facilitate introduction into a patient's body. Alternatively, distal advancement of the inner member 30" may be limited, e.g., by an actuator on the proximal end (not shown) of the apparatus 10," such that the outlet 58" is opened without excessive stretching of the balloon 50." For example, the apparatus 10" may include a handle or hub (not shown) on the proximal end of the outer member 20," and an actuator (also not shown) on the handle may be movable for directing the apparatus 10" between the open and closed positions. Optionally, the actuator may be biased to one of the positions, similar to the other embodiments herein.

Figure 5A:
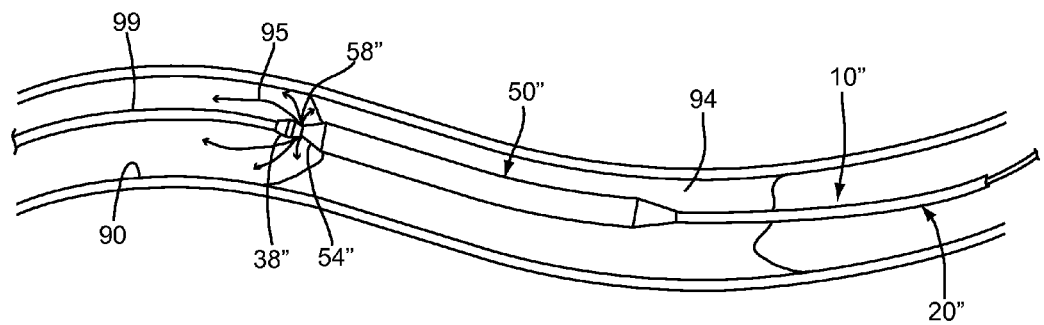
FIGS. 5A-5C are cross-sectional views of a body lumen within a patient's body showing different methods for treating a body lumen using the apparatus of FIG. 3.
Figure 5B:
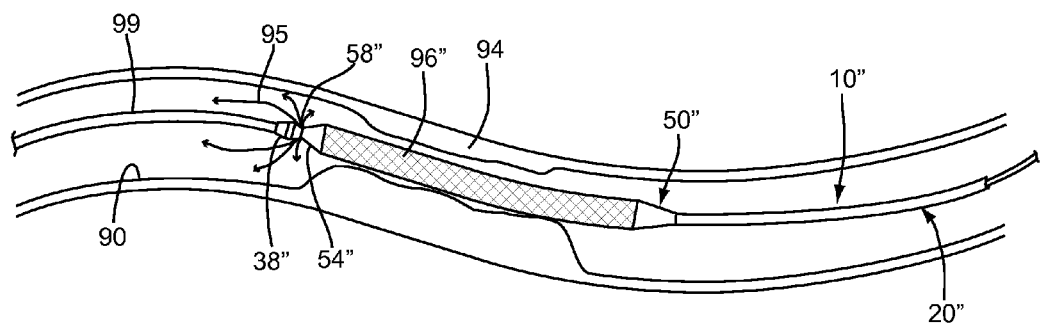
Figure 5C:
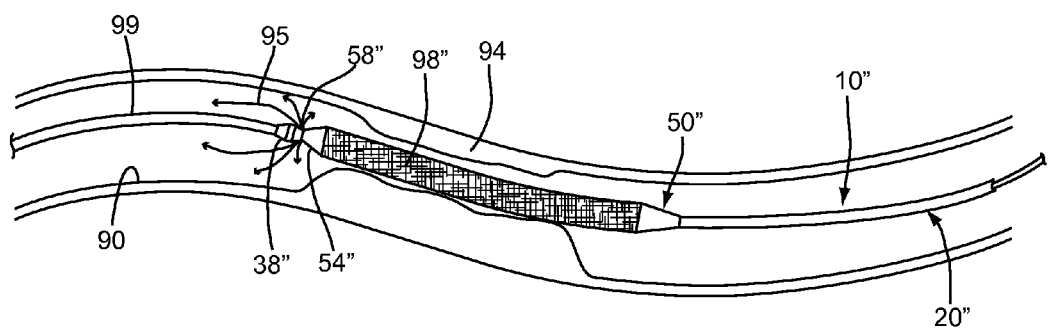

Turning to FIGS. 5A-5C, exemplary methods are shown for treating a body lumen 90, e.g., using the apparatus 10" (or any of the other apparatus herein). The target body lumen 90 may be a blood vessel, e.g., a vein or artery, a graft, e.g., an aorto-venous fistula, tubular xenograft, or synthetic tubular graft, and the like. For example, the body lumen 90 may be a passage communicating between an adjacent artery and vein (not shown), e.g., in an arm or other region of a dialysis patient. Alternatively, the body lumen 90 may be a blood vessel within a patient's vasculature, e.g., a peripheral vessel in a patient's leg, a cerebral vessel, and the like.

Optionally, the body lumen 90 may be accessed using one or more additional instruments (not shown), which may be part of a system or kit including the apparatus 10." For example, an introducer sheath, guide catheter, or other tubular member (not shown) may be introduced adjacent the target site, or may be introduced elsewhere in the patient's body to provide access to the patient's vasculature or other passages communicating with the body lumen. If the body lumen 90 is located in a peripheral vessel of the patient, a percutaneous puncture or cut-down may be created using a needle or other instrument (not shown) at a peripheral location, such as a femoral artery, carotid artery, or other entry site (also not shown), and an introducer sheath may be placed through the puncture at the peripheral location to provide access. The apparatus 10" may be advanced through the patient's vasculature from the entry site, e.g., alone or with the aid of a guide catheter, guidewire, and the like (not shown).

For example, to facilitate directing the apparatus 10" from an entry site to the target body lumen 90, a guide catheter, micro-catheter, or other tubular body (not shown) may be placed from the entry site to the body lumen 90 using conventional methods. In addition or alternatively, a guidewire 99" may be placed from the entry site to the body lumen 90, as shown, e.g., if the inner member 30" includes the second lumen 36" (not shown, see FIGS. 3-4B).

Turning to FIG. 5A, in a first exemplary method, the body lumen 90 may include an occlusion 94, e.g., a chronic total occlusion within a blood vessel, and the guidewire 99" may be tracked from the entry site into the body lumen 90 and through the occlusion 94, e.g., using known methods. Such lesions may be particularly difficult to treat because there is little opportunity to perform conventional dye injections to facilitate imaging since there is no flow through the body lumen 90. Further, it may be difficult to track and/or position the guidewire 99" and/or apparatus 10" within the body lumen 90 without using dye injections.

Initially, the apparatus 10" may be advanced into the body lumen 90 with the balloon 50" in its collapsed condition. For example, the apparatus 10" may be advanced over the guidewire 99" previously placed through the occlusion 94, e.g., until the distal end 54" of the balloon 50" enters the region of the body lumen 90 beyond the occlusion 94, as shown.

With the distal end 54" of the balloon 50" beyond the occlusion 94 and the valve open, radiopaque contrast, dye, or other fluid, represented by 95, may be delivered into the body lumen 90 via the annular passage defined by the first lumen between the outer and inner members 20," 30" to facilitate locating and/or measuring the size of the material of the occlusion 94 and/or body lumen 90, e.g., using fluoroscopy. Markers (not shown) on the apparatus 10" may facilitate positioning the balloon 50" relative to the occlusion 94 before the balloon 50 is expanded, e.g., to facilitate verifying that the balloon 50" is positioned through and/or across the occlusion 94. If desired, the inner member 30" may be directed back and forth between the first and second positions, e.g., to allow infusion of contrast and to reduce the profile of the apparatus 10" to facilitate further advancement, e.g., until the balloon 50" is located beyond the occlusion 94.

Thus, the apparatus 10" may facilitate dye injection beyond the occlusion 94 while maintaining the guidewire 99" in position. Unlike the apparatus 10," conventional devices may require removing a guidewire or other device advanced through the occlusion 94 to allow dye injections and imaging beyond the occlusion 94. In such procedures, it may be difficult to reintroduce the guidewire or other device back through the small passage created through the occlusion 94.

With continued reference to FIG. 5A, once the apparatus 10" is positioned with the balloon 50" across the occlusion 94, the valve may be closed and the balloon 50" may be inflated within the body lumen 90, e.g., to dilate or otherwise treat the occlusion 94. Optionally, as shown in FIG. 5B, a stent 96" may be carried by the balloon 50" and may be expanded by inflating the balloon 50." For example, with the valve of the apparatus 10" open, dye 95 may be injected into the body lumen 90 to facilitate imaging and positioning the apparatus 10." Once the stent 96" is positioned across the occlusion 94, the valve may be closed, and the balloon 50" inflated to expand the stent 96" and dilate the occlusion 94 (not shown). Once the stent 96" is expanded, the balloon 50" may be collapsed and the apparatus 10" removed from the body lumen 90 and patient's body.

If desired, the obstructive material may be treated, e.g., at least partially dissolved, macerated, and the like before, during, or after withdrawal. For example, a therapeutic agent may be delivered into the body lumen 90 via the first lumen of the outer member 20," e.g., to at least partially dissolve or separate thrombus or other relatively soft material before being dilated by the balloon 50" and/or stent 96."

Turning to FIG. 5C, in another method, the apparatus 10" may be used as a drug delivery platform for treating the occlusion 94. For example, in some applications, it may be desirable to deliver an anti-restenosis drug without a stent. As shown, the apparatus 10" includes a carrier 98" provided over the balloon 50" that may be delivered into the body lumen 90 and/or through the occlusion 94." For example, as described above, the apparatus 10" may be advanced into the body lumen 90 with the balloon 50" and the carrier 98" thereon in a collapsed condition, e.g., over the guidewire 99."

With the distal end 54" of the balloon 50" beyond the occlusion 94 and the valve open, contrast, dye, or other fluid 95 may be delivered into the body lumen 90 to facilitate locating and/or measuring the size of the occlusion 94 and/or body lumen 90, e.g., using fluoroscopy. Once the apparatus 10" is positioned with the balloon 50" across the occlusion 94, the valve may be closed and the balloon 50" inflated within the body lumen 90 to dilate the occlusion 94 and deliver the carrier 98." Once the carrier 98" is delivered, the balloon 50" may be collapsed and the apparatus 10" removed from the body lumen 90 and patient's body. One or more therapeutic agents may be positioned within or otherwise carried by the carrier 98" and, therefore, may remain within the dilated occlusion 94 to treat the body lumen 90.

Alternatively, the agent(s) may be delivered directly from the wall of the balloon 50." For example, the agent(s) may be infused through the wall of the balloon 50," e.g., by providing a porous layer on the balloon 50" into which the agent(s) may be embedded or otherwise placed.

In another alternative, the agent delivered into the body lumen 90 may be provided from multiple components that may react or interact in situ once delivered together within the body lumen 90. For example, a first component (or one or more additional components less than all components of the agent) may be carried on the wall of the balloon 50," e.g., in a porous layer or on a carrier 98" disposed around the balloon 50," as described above. The second component (or multiple remaining components needed for the agent) may be delivered via the outlet 58" on the apparatus 10." For example, after one or more components are delivered by closing the valve and inflating the balloon 50" within the occlusion 94, the valve may be opened and a fluid carrying the one or more remaining components may be delivered into the body lumen 90. The components may then combine to form an active drug or agent that may treat the material of the occlusion 94 and/or otherwise treat the body lumen 90.

Figure 7:
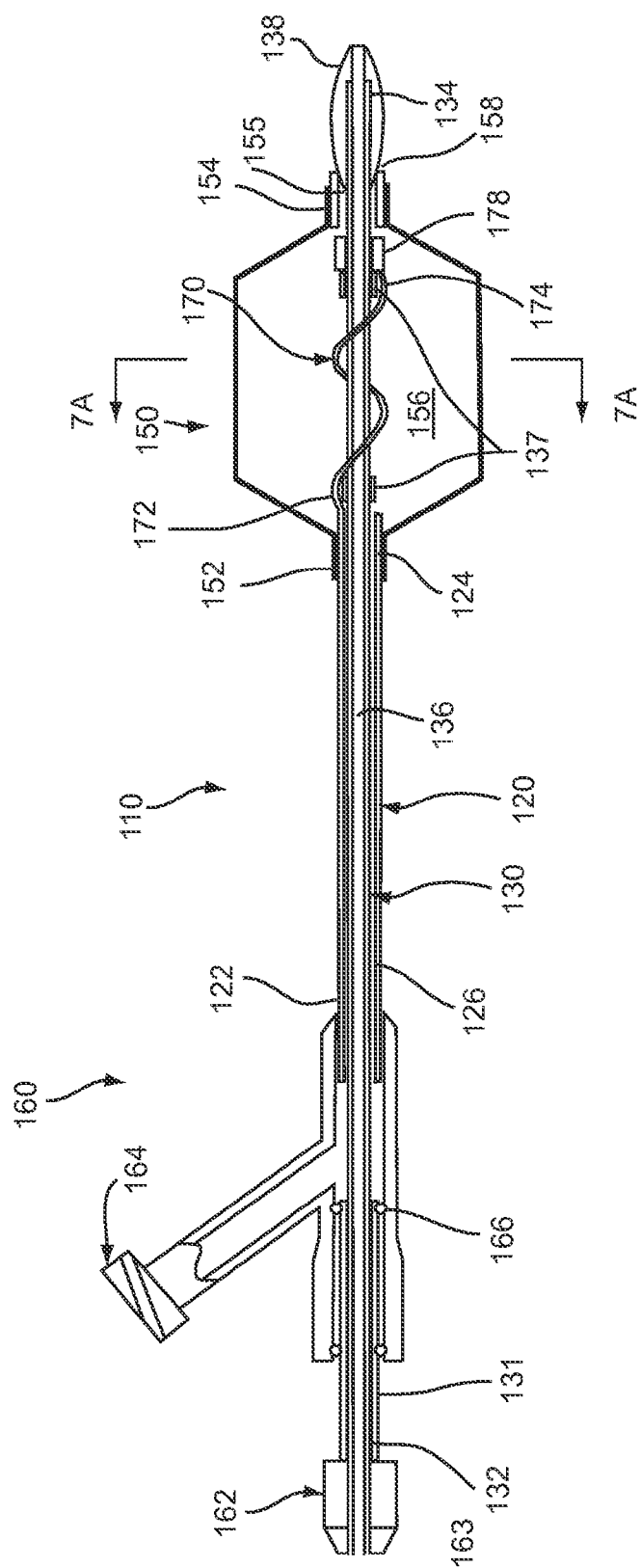
FIG. 7 is a side view of yet another exemplary embodiment of an apparatus including a balloon for treating a body lumen, the apparatus operable in a first mode for infusing fluid into the body lumen, a second mode for dilating an obstruction within the body lumen, and a third mode for removing material within the body lumen.

Turning to FIG. 7, another embodiment of an apparatus 110 is shown for treating a body lumen that generally includes an outer tubular member 120, an inner member 130, and an expandable balloon 150 carried by the inner and/or outer members 120, 130, similar to other embodiments herein. The apparatus 110 may be operable in a first mode for infusing fluid into a body lumen, a second mode for dilating an obstruction within a body lumen, and/or a third mode for removing obstructive material within a body lumen, as described further below.

As shown, the outer member 120 includes a proximal end 122, a distal end 124 sized for introduction into a body lumen, and a first lumen 126 extending between the proximal and distal ends 122, 124, which may be constructed similar to other embodiments herein. The inner member 130 also includes a proximal end 132, a distal end 134, and, optionally, a second lumen 136 extending between the proximal and distal ends 132, 134, e.g., sized to slidably receive a guide wire, or other rail (not shown) therethrough. The inner member 130 is sized to be slidably received within the first lumen 126 of the outer member 120, e.g., such that an annular space is defined between the outer and inner members 120, 130 for passing one or more fluids therethrough, also similar to other embodiments herein.

The balloon 150 includes a proximal end 152 coupled to the outer member distal end 124, a distal end 154 defining an outlet 158, and an interior 156 communicating with the first lumen 126 and the outlet 158. The distal end 134 of the inner member 130 may extend through the distal end 154 of the balloon 150, e.g., such that the outlet 158 defines an annular passage between the distal end 154 of the balloon 150 and the distal end 134 of the inner member 130. As shown, the distal end 154 of the balloon 150 may include a collar or sleeve 155 attached or otherwise secured to the distal end 154, e.g., by bonding with adhesive, interference fit, sonic welding, fusing, and the like. Optionally, the collar 155 may extend proximally into the interior 156 of the balloon 150 (not shown) and the interior section of the collar 155 may include one or more side ports or other openings (also not shown), e.g., to facilitate fluid passing from the balloon interior 156 through the outlet 158. Alternatively, the distal end 154 of the balloon 150 may be integrally formed with the balloon 150 from similar or dissimilar materials as the main portion of the balloon 150 and/or may include other features (not shown), e.g., similar to other embodiments herein.

The balloon 150 may be formed from substantially inelastic material, e.g., to provide a non-compliant balloon that expands to a predetermined size when inflated independent of pressure (once a minimum volume is introduced to achieve the predetermined size). Such a non-compliant balloon 150 may expand to the predetermined size even if inflated to relatively high pressures, e.g., until the balloon 150 bursts or otherwise ruptures, e.g., at pressures of at least ten atmospheres, twenty atmospheres, thirty atmospheres, and the like. Alternatively, the balloon 150 may be formed from elastic material, similar to other embodiments described elsewhere herein.

One or more sealing members 138 may be carried on the inner member distal end 134, e.g., such that the sealing member(s) 138 are movable relative to the balloon 150 as the inner member 130 is moved, e.g., to provide a valve for selectively opening and closing the outlet 158 of the balloon 150. As shown, a first sealing member 138 is provided on the inner member 130 distal to the balloon distal end 154 and collar 155. The sealing member 138 may have a size, e.g., outer diameter, that is larger than the collar 155 and/or the distal end 154 of the balloon 150 such that the sealing member 138 may substantially engage the collar 155 and/or distal end 154 of the balloon 150 to substantially seal the outlet 158.

Figure 32:
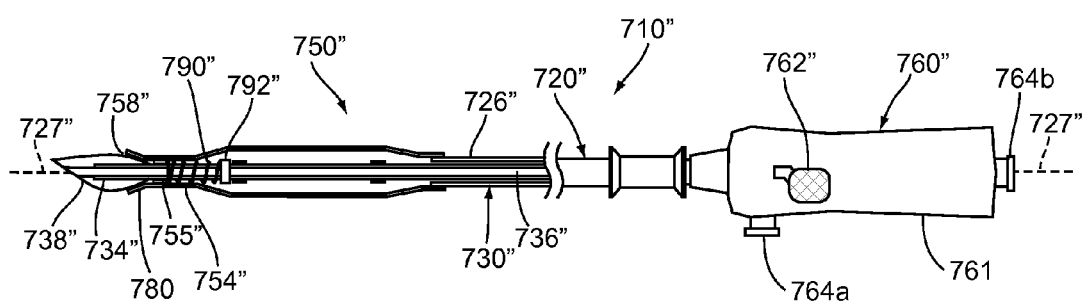
FIG. 32 is a partially cross-sectional side view of yet another exemplary embodiment of an apparatus for treating a body lumen.
Figure 33A:
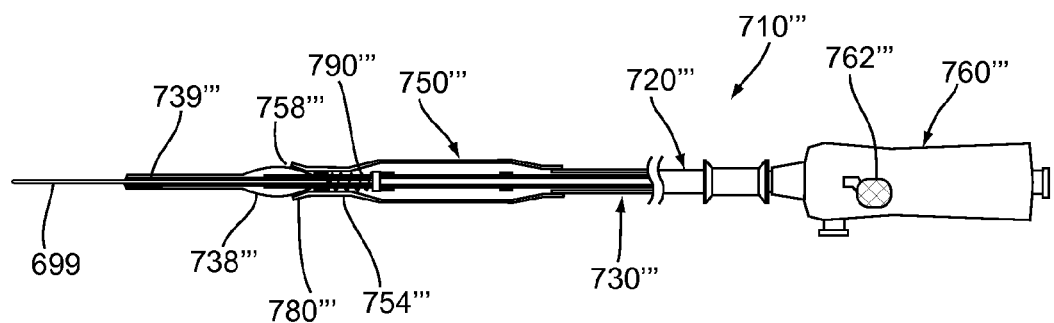
FIGS. 33A and 33B are partially cross-sectional side views of still another exemplary embodiment of an apparatus for treating a body lumen, including a guidewire inserted into and removed from the apparatus, respectively.
Figure 33B:
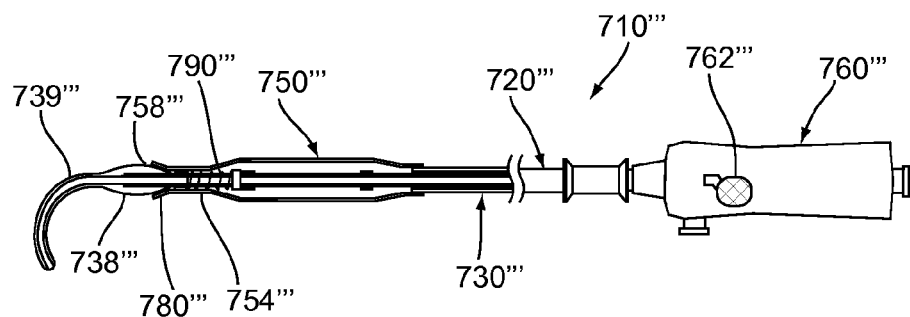

In the exemplary embodiment shown, the sealing member 138 may include a tapered shape, e.g., on one or both of its proximal and distal ends to provide a nosecone on the inner member 130. For example, a tapered shape on the proximal end of the sealing member 138 may automatically guide the sealing member 138 into being seated in the outlet 158 of the balloon 150, e.g., to enhance a fluid-tight seal therebetween. A tapered shape on the distal end of the sealing member 138 may provide a rounded or otherwise substantially atraumatic tip for the apparatus 110. In addition or alternatively, other substantially atraumatic distal tips (not shown) may be provided on the inner member 130 beyond the first sealing member 138, similar to other embodiments herein, e.g., a "J" shaped tip, as shown in FIGS. 33A and 33B, a beveled tip, as shown in FIG. 32, a threaded tip, and the like (not shown).

With continued reference to FIG. 7, a handle or hub 160 may be coupled to or otherwise provided on the proximal end 122 of the outer member 120, e.g., for manipulating the outer member 120 and/or the entire apparatus 110, generally similar to the other embodiments herein. The handle 160 may include a pull handle 162 or other actuator coupled to the inner member 130 for moving the inner member 130 to the various positions described below. The handle 160 may also include one or more ports, such as side port 164 for coupling one or more fluid sources to the apparatus 110, e.g., a syringe or other source of fluid for delivering fluid through the first lumen 126 into the interior 156 of the balloon 150 and/or through the outlet 158, depending upon the position of the inner member 130.

Optionally, the handle 160 may include one or more seals, bushings, and the like, such as o-ring 166, between the outer and inner members 120, 130, which may guide the inner member 130 as it moves axially relative to the outer member 130 and handle 160. In this embodiment, the inner member 130 includes a section of hypotube or other substantially rigid tubing 131 attached or otherwise coupled to the proximal end 132 of the inner member 130. The tubing 131 may provide axial support for the inner member 130, e.g., to prevent buckling or kinking when the inner member 130 is directed axially. The tubing 131 may also allow the inner member 130 to move axially more easily, e.g., if the tubing 131 has a substantially smooth or lubricated outer surface that slides easily through the o-ring 166 while maintaining a fluid-tight seal therebetween.

In addition or alternatively, if desired, the apparatus 110 may include one or more markers to facilitate positioning and/or advancement of the apparatus 110 during use. For example, as shown in FIG. 7, radiopaque marker bands 137 may be attached around the distal end 134 of the inner member 130, e.g., within the balloon interior 56. As shown, a marker 137 is attached adjacent both the proximal end 152 and the distal end 154 of the balloon 150, which may facilitate monitoring the location of the balloon 150 before dilating an obstruction within a body lumen. In addition or alternatively, a core wire of the helical member 170 may be formed from radiopaque material, and/or radiopaque filler material, BAS04, may be dispersed into plastic material used to form the helical member 170, if desired.

Unlike the previous embodiments, the apparatus 110 includes a helical member 170 coupled between the outer and inner members 120, 130 within the balloon interior 156. The helical member 170 may be movable from a relatively low profile, such as that shown in FIG. 7, to an expanded helical shape, as described further below. As shown, the helical member 170 is a wire, tube, or other filament including a first end 172 coupled to the distal end 124 of the outer member 120 and a second end 174 coupled to the distal end 134 of the inner member 130. For example, the helical member 170 may be from a core wire having a tube or sleeve formed or attached around the wire (not shown). Alternatively, the helical member 170 may be formed from multiple filaments (not shown) wound around one another or otherwise coupled together to act as a unitary structure. In exemplary embodiments, the helical member 170 may be made from thermoplastic, thermoset, and/or other plastics, glass, metal, or composite materials.

Between the first and second ends 172, 174, the helical member 170 may wrap helically around the inner member 130 one or more times. As shown, the helical member 170 extends around the inner member 130 about one and a half turns, although it will be appreciated that the helical member 170 may include more or fewer turns.

As shown, the first end 172 of the helical member 170 may be attached or otherwise secured directly to the distal end 124 of the outer member 120, e.g., by one or more of bonding with adhesive, sonic welding, soldering, interference fit (e.g., by wrapping the first end 172 one or more times around the distal end 124), inserting the first end 172 into an annular groove, hole, or pocket (not shown) in the distal end 124, fusing, by an overlying band or collar (also not shown), and the like. The second end 174 of the helical member 170 may be similarly attached or otherwise secured to a sleeve 178 fixed to the distal end 134 of the inner member 130 or directly to the distal end 134.

The sleeve 178 may be a relatively short tube attached to the inner member distal end 134 adjacent the balloon distal end 154, e.g., by bonding with adhesive, sonic welding, interference fit, fusing, and the like. The sleeve 178 may have an outer diameter larger than the inner diameter of the collar 155 and/or distal end 154 of the balloon 150, thereby providing a stop that limits movement of the collar 155 and distal end 154 relative to the inner member 130. When the sleeve 178 contacts the collar 155 and/or distal end 154, the sleeve 178 may not substantially obstruct the annular passage communicating with the outlet 158, e.g., such that fluid may still flow through the outlet 158 when introduced into the balloon interior 156. Alternatively, the sleeve 178 may be shaped to substantially seal the outlet 158 when the sleeve 178 engages the collar 155 and/or distal end 154 of the balloon 150, similar to the other sealing members described elsewhere herein. Optionally, during manufacturing or assembly, the collar 155 may be positioned between the sealing member 138 and the sleeve 178 when the collar and sleeve 178 are attached to the inner member distal end 134, i.e., before attaching the collar 155 to the balloon distal end 154. The balloon distal end 154 may then be attached over the collar 155 when the balloon 154 is attached to the outer member distal end 124. If desired, the balloon distal end 154 may be attached to the collar 155 such that a proximal section of the collar 155 is disposed within the interior 156 of the balloon 150. If so, the proximal section of the collar 155 may include one or more openings (not shown) to facilitate fluid passing from the balloon interior 156 through the collar 155 and out the outlet 158, i.e., when the outlet 158 is not sealed by the sealing member 138, as described further below.

The inner member 130 may be movable axially relative to the outer member 120, e.g., between a first or distal position, a second or intermediate position (shown in FIG. 7), and/or a third or proximal position (not shown), thereby allowing the apparatus 110 to provide different functions for treating a body lumen. For example, in the first position, the inner member 130 may direct the sealing member 138 distally such that the sealing member 138 is spaced apart from the balloon outlet 158. Thus, fluid introduced through the first lumen 126 of the outer member 120 may pass through the balloon interior 156 and out the outlet 158, e.g., into the body lumen beyond the distal tip 35, similar to the previous embodiments.

If desired, the inner member 130 may be directed proximally to a second position, such as that shown in FIG. 7, in which the sealing member 138 engages the collar 155 and/or distal end 154 of the balloon 150, thereby substantially sealing the outlet 158 from fluid flow therethrough. Thus, any fluid introduced through the first lumen 126 enters the balloon interior 156 and may expand the balloon 150. In this mode, the balloon 150 may be expanded to an elongate substantially cylindrical shape, e.g., having a substantially uniform diameter main portion between tapered end portions. In the expanded condition, the main portion of the balloon 150 may have a length between about twenty and eighty millimeters (20-80 mm) and a diameter between about three and twelve millimeters (3-12 mm). The balloon 150 may be used to dilate or otherwise apply substantial pressure to a wall of a body lumen, e.g., for dilating a stenosis, lesion, or other obstruction, similar to the method shown in FIGS. 9E-9G and described further below.

In addition or alternatively, after inflating the balloon 150 to dilate the body lumen, a source of vacuum may be coupled to the side port 164 and the balloon 150 collapsed to a contracted condition around the helical member 170. Alternatively, if the balloon 150 has not been previously inflated, it may not be necessary to collapse the balloon 150 using vacuum since the balloon 150 may already be sufficiently collapsed or otherwise remain in the contracted condition.

The inner member 130 may then be directed proximally to the third position, thereby directing the ends of the helical member 170 towards one another. This causes the helical member 170 to expand radially outwardly as it is compressed axially, thereby causing the balloon 150 also to compress axially and expand radially into an expanded helical shape around the helical member 170, e.g., as shown in FIGS. 9C and 9D. Optionally, the inner member 130 and/or handle 150 may include one or more stops (not shown) that limit proximal movement of the inner member 130 when compressing and expanding the balloon 150 and helical member 170. For example, the stop(s) may allow the inner member 130 to be pulled until the balloon length is reduced to between about six and thirty millimeters (6-30 mm), thereby preventing overcompression of the balloon 150 and/or helical member 170.

In one embodiment, the helical member 170 may have sufficient rigidity that the helical member 170 may simply buckle elastically from the low profile towards the helical shape as it is compressed axially. Thus, the helical member 170 may expand without substantial plastic deformation such that the helical member 170 may be returned to its original low profile shape (and expanded and collapsed repeatedly, if desired). Alternatively, the helical member 170 may be biased to a predetermined expanded helical shape but may be constrained in the low profile, e.g., by providing axial tension on the ends 172, 174 of the helical member 170 when the inner member 130 is in the first or second positions. As the inner member 130 is directed towards the third position, the tension may be released, whereupon the helical member 170 may resiliently expand towards the expanded helical shape.

In another alternative, the helical member may be integrally formed or otherwise coupled directly to the balloon 150, e.g., attached to, embedded within, or otherwise secured to the balloon wall (not shown) between the proximal and distal ends 152, 154. For example, as shown in FIGS. 7B and 7D, one or more helically shaped wires or fibers 157' (e.g., one shown in FIG. 7B, two shown in FIG. 7D) may be molded, embedded, or integrally formed in the wall of the balloon 150.' As the balloon 150' is compressed axially when the inner member 130 is moved towards the third position, the fiber(s) 157' may automatically bias the balloon 150' towards the expanded helical shape. Alternatively, as shown in FIG. 7C, a fiber 157" may be molded, embedded, or integrally formed in the wall of the balloon 150" that includes a core wire or member 159," e.g., a radiopaque material, a biased core wire, and the like. In further alternatives, FIGS. 7E-7H show alternate shapes and/or configurations for a fiber $157_e$ to $157_h$ or other stiffening features that may be molded, embedded, or otherwise integrally formed in the wall of the balloon $150_e$ to $150_h$ and extend helically between proximal and distal ends of the balloon $150_e$ to $150_h$. The fiber(s) and/or stiffening features may include one or more turns between the proximal and distal ends of the balloon 150', 150", or $150_e$ to $150_h$, e.g., one and a half, two, three, four, or more turns. In addition, any of the fibers and/or stiffening features included on a balloon may provide cutting edges or elements, e.g., that may be at least partially embedded into a wall of a body lumen when the balloon 150', 150", or $150_e$ to $150_h$ is inflated to dilate an obstruction in a body lumen.

Returning to FIG. 7, with the balloon 150 in the expanded helical shape, the entire apparatus 110 may be directed along a body lumen, e.g., to remove obstructive material including scraping, scrubbing, or otherwise separating adherent material from a wall of the body lumen, if desired, similar to the method shown in FIGS. 9A-9D and described further below. Thus, in this embodiment, a single balloon 150 may be used for both dilation, e.g., using relatively high pressures, and for scraping, scrubbing, or otherwise removing obstructive material within a body lumen.

Figure 23A:
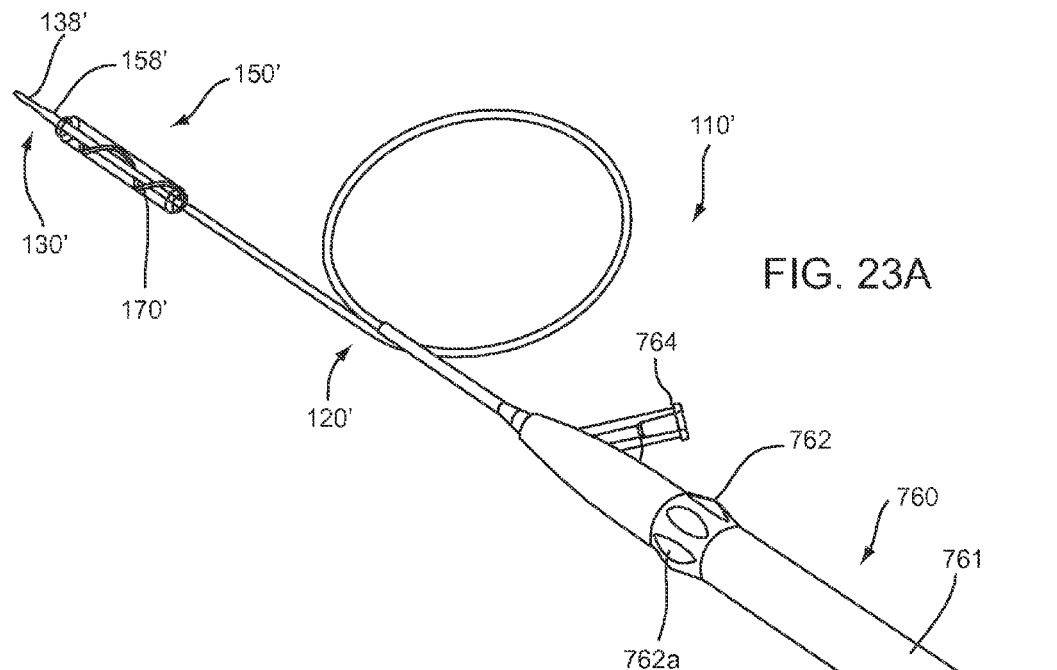
FIG. 23A is a perspective view of an apparatus, similar to that shown in FIG. 7, including a first exemplary embodiment of a handle for actuating the apparatus.
Figure 23B:
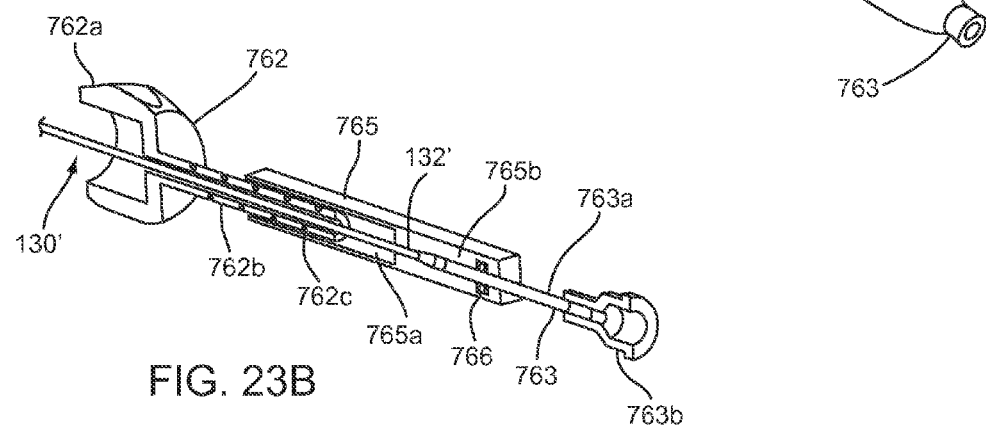
FIG. 23B is a cross-sectional detail of components of a rotary knob control on the handle of FIG. 23A with a housing of the handle removed to show internal components.

Turning to FIGS. 23A and 23B, an apparatus 110' is shown that is generally similar to the apparatus 110 of FIG. 7, except that the apparatus 110' includes an alternative embodiment of a handle 760 on the proximal end 122' of the outer member 120.' Generally, the handle 760 includes an outer housing 761 (shown in FIG. 23A), an inner carriage 765 (shown in FIG. 23B) slidable axially within the housing 761, a rotary knob 762 carried by the housing 761 and coupled to the carriage 765, and a hub 763 extending from the housing 761. It will be appreciated that the handle 760 (and the other handles described below and elsewhere herein) may be provided on any of the apparatus described herein, e.g., that include actuators for opening and closing a valve on the apparatus and/or otherwise expanding and/or collapsing a helical member on the apparatus.

The housing 761 may include one or more pieces, e.g., one or more sets of mating halves or clamshells (not shown) that may be connected together, e.g., along a longitudinal seam (also not shown) to provide the housing 761, e.g., secured together by mating connectors, bonding with adhesive, sonic welding, fusing, and the like. The housing 761 may include a slot, track, or other features (not shown) that allow the carriage 765 to slide axially within the housing 761 without substantial lateral movement. The housing 761 and/or carriage 765 may include one or more cooperating features, e.g., stops (not shown) within the housing 761 that limit axial movement of the carriage 765 relative to the housing 761, for example, to limit movement of the inner member 130' between the first position (for infusion from the outlet 158') and the third position (where the balloon 150' is directed to an expanded helical shape, not shown).

The housing 761 may include a side port 764, e.g., including a Luer lock or other connector, for connecting a source of fluid to the apparatus 110.' The side port 764 may communicate with a lumen extending through the outer member 120' for delivering fluid into the interior of the balloon 150,' similar to the previous embodiments.

The knob 762 may include an outer portion 762a surrounding or otherwise extending radially from the housing 761, e.g., including ridges or other features to facilitate rotation or other manipulation of the knob 762 during use, and an inner stem 762b that extends axially along a first passage 765a within the carriage 765. The inner stem 762b and the carriage 765 may include cooperating features, e.g., helical threads 762c, that translate rotation of the knob 762 into axial movement of the carriage 765. Thus, the knob 762 may be substantially fixed axially relative to the housing 761 and freely rotatable about a longitudinal axis of the apparatus 110.'

The proximal end 132' of the inner member 130' may pass freely through the inner stem 762b and be fixed relative to the carriage 765. For example, the inner member proximal end 132' may be secured to the carriage 765 by fixing the proximal end 132' in a second passage 765b adjacent to and/or communicating with the first passage 765a, e.g., by bonding with adhesive, sonic welding, fusing, interference fit, mating connectors (not shown), and the like. Thus, axial movement of the inner member 130' may be coupled to movement of the carriage 765.

The hub 763 may include a hypotube or other tubular member 763a and a Luer lock or other connector 763b secured to one another and/or to the outer housing 761. For example, a proximal end of the tubular member 763a and/or the connector 763b may be attached to a proximal end of the housing 761, e.g., by bonding with adhesive, sonic welding, fusing, interference fit, mating connectors (not shown), and the like.

The tubular member 763a may be slidably received in the second passage 765b such that the tubular member 763a and connector 763b remain substantially stationary relative to the housing 761 as the carriage 765 is directed axially. One or more seals, e.g., o-ring 766, may be provided within or around the second passage 765b that allow the tubular member 763a to slide therethrough while providing a fluid-tight seal that prevents fluid from leaking through the passages 765a, 765b and out of the housing 761.

During use, the knob 762 may be rotated in a first direction, thereby translating the inner member 130' distally to the first position to open the outlet 158.' Thus, fluid delivered through the outer member 120' may pass through the balloon 150' and exit the outlet 158,' as described above. The knob 762 may be rotated in a second opposite direction, thereby translating the inner member 130' proximally to the second position, e.g., until the sealing member 138' seals the outlet 158' to allow balloon expansion, and/or further to the third position, e.g., to expand the balloon 150' to the expanded helical shape, also as described above. Optionally, the knob 762 and/or housing 761 may include visual, audible, or other indicators (not shown) that identify the direction to rotate the knob 762 to achieve the desired position(s) and/or that indicate when a particular position is achieved, e.g., by aligning an arrow (not shown) on the knob 762 with respective indicators (also not shown) that identify the first, second, and/or third positions. Otherwise, the apparatus 110' may operate similar to the previous embodiments.

Figure 24A:
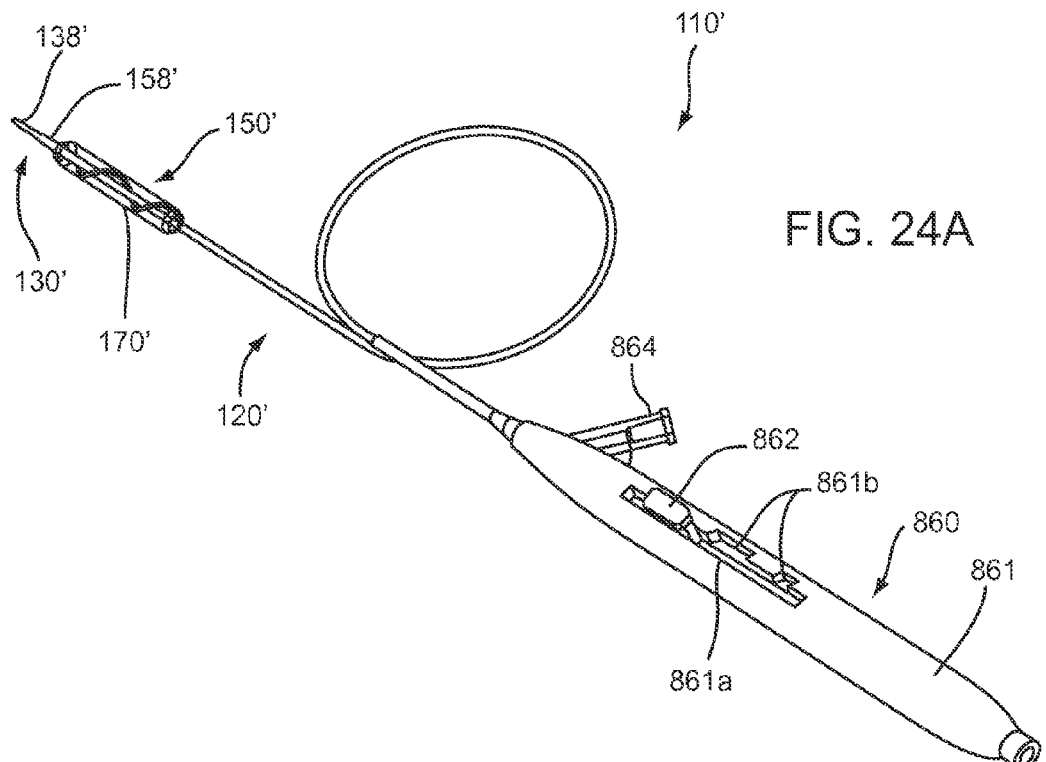
FIG. 24A is a perspective view of another apparatus, similar to that shown in FIG. 7, including a second exemplary embodiment of a handle for actuating the apparatus.
Figure 24B:
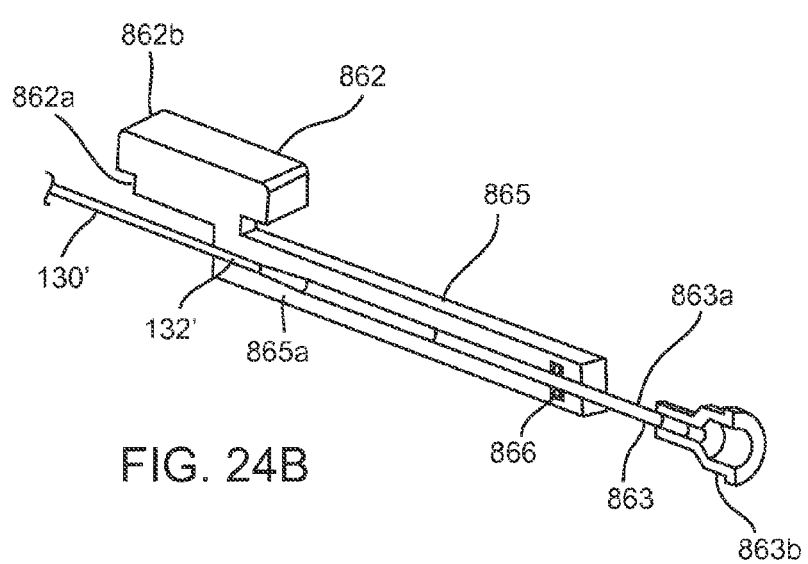
FIG. 24B is a cross-sectional detail of components of a slider control on the handle of FIG. 24A with a housing of the handle removed to show internal components.
Figure 24C:
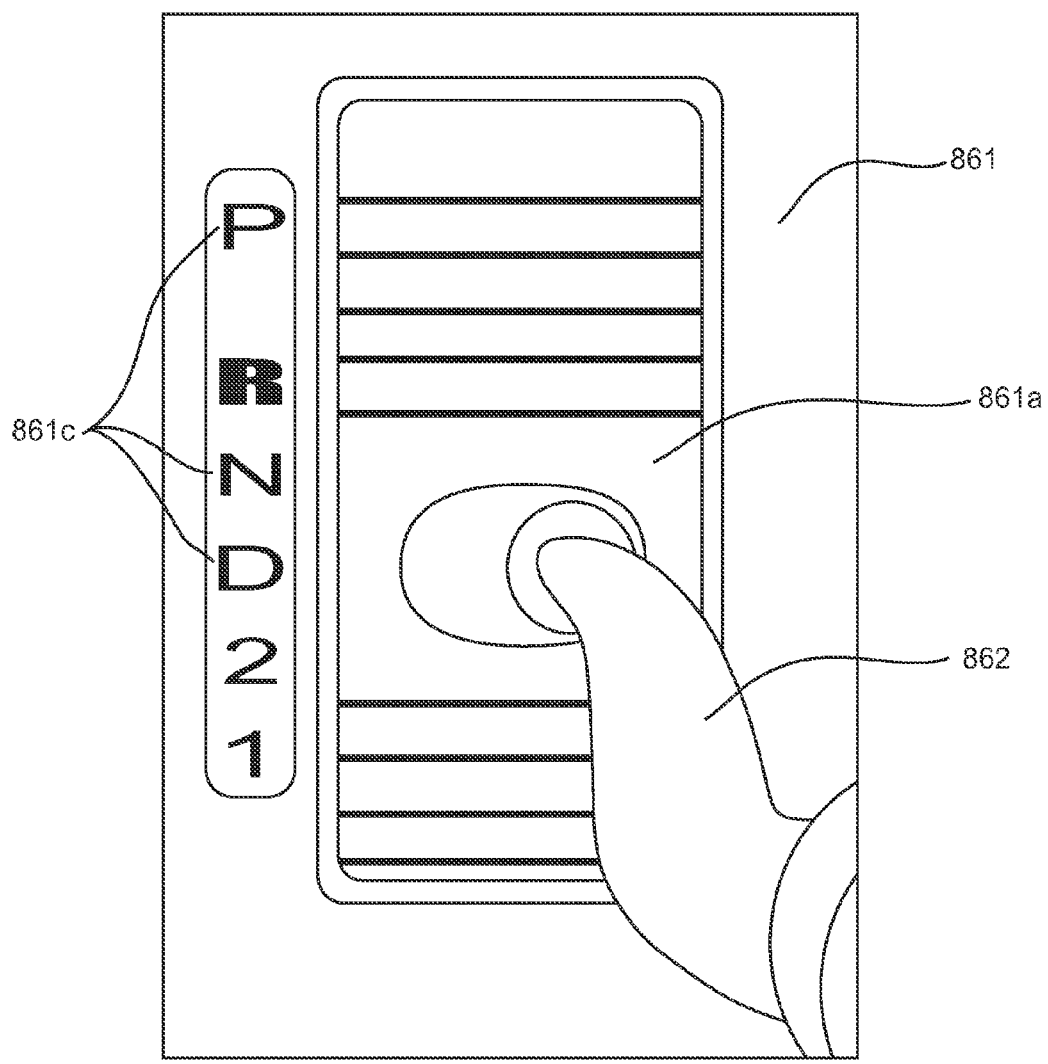
FIG. 24C is a detail of an alternate slider control, similar to that shown in FIGS. 24A and 24B, including visual indicators identifying actuatable positions of the apparatus.

Turning to FIGS. 24A-24C, another embodiment of a handle 860 is shown that includes an outer housing 861 with a side port 864 (shown in FIG. 24A), an inner carriage 865 (shown in FIG. 24B) slidable axially within the housing 861, and a hub 863 extending from the housing 861, generally similar to the handle 760. For example, the housing 861 may include one or more pieces, e.g., one or more sets of mating halves or clamshells (not shown) that may be connected together and may include a slot, track, or other features (not shown) that allows the carriage 865 to slide axially within the housing 861, e.g., without substantial lateral movement. The housing 861 and/or carriage 865 may include one or more features that limit axial movement of the carriage 865 relative to the housing 861, e.g., to limit movement of the inner member 130' between the first position (for infusion from the outlet 158'), second position (for balloon inflation), and the third position (where the balloon 150' is directed to an expanded helical shape, not shown).

The proximal end 132' of the inner member 130' is substantially fixed relative to the carriage 865, e.g., by fixing the proximal end 132' in a passage 865a adjacent to a distal end of the carriage 865, for example, by bonding with adhesive, sonic welding, fusing, interference fit, mating connectors (not shown), and the like. Thus, axial movement of the inner member 130' may be coupled to movement of the carriage 865.

The hub 863 may include a hypotube or other tubular member 863a and a Luer lock or other connector 863b secured to one another and/or to the outer housing 861. For example, a proximal end of the tubular member 863a and/or the connector 863b may be attached to a proximal end of the housing 861, e.g., by bonding with adhesive, sonic welding, fusing, interference fit, mating connectors (not shown), and the like.

The tubular member 863a may be slidably received in the passage 865a, e.g., adjacent a proximal end of the carriage 865, such that the tubular member 863a and connector 863b remain stationary relative to the housing 861 (and inner member proximal end 132') as the carriage 865 is directed axially. With both the tubular member 863a and inner member proximal end 1323' received in the passage 865a, a guidewire or other instrument, backloaded through the inner member 130,' may pass freely through the passage 865a, tubular member 863a, and out the connector 863b (or inserted through the connector 863b into the inner member 130'). One or more seals, e.g., o-ring 866, may be provided within or around the passage 865a that allow the tubular member 863 to slide therethrough while providing a fluid-tight seal that prevents fluid from leaking through the passage 865a out of the housing 861.

Instead of a rotary knob 762, the handle 860 includes a push button 862 carried by the housing 861 and coupled to the carriage 865. For example, the housing 861 may include an elongate slot 861a and the push button 862 may be slidable axially within the slot 861a. Optionally, as shown, the slot 861a may include one or more pockets or detents 861b that may capture the push button 862, e.g., to releasably secure the push button 862, and consequently the carriage 865 and inner member 130,' in one or more positions.

Optionally, the housing 861 may include one or more visual indicators, e.g., for identifying the position of the inner member 132' when the push button 862 is received in a particular pocket 861b. For example, as shown in FIG. 24C, the housing 861 may include numbers or other symbols 861c aligned with respective pockets (not shown) such that when the push button, in this embodiment, lever 862 is aligned with a particular symbol 861c, the user can confirm that the inner member 130' is in a respective particular position.

As best seen in FIG. 24B, the push button 862 may include a base 862a substantially fixed relative to the carriage 865 and a cap 862b slidable laterally relative to the base 862a. For example, the base 862a may be integrally molded or otherwise formed with the carriage 865 and the cap 862b may be attached to the base 862a such that the cap 862b may be slid laterally, e.g., substantially perpendicular to the longitudinal axis of the handle 860. For example, the cap 862b may be biased such that the cap 862b may automatically slide into a pocket 861b with which the cap 862b is aligned, yet the bias may be overcome to move the cap 862b out of the respective pocket 861b into the slot 861a so that the cap 862b may be slid axially into another pocket 861b. For example, a spring or other biasing mechanism (not shown) may be provided within the cap 862b or housing 861 that may push the cap 862b laterally from the base 862a.

Alternatively, the entire push button 862 may be fixed relative to the carriage 865, e.g., integrally molded or formed together, and the push button 862 and carriage 865 may be pivoted about the longitudinal axis to allow the cap 862b to be directed out of a particular pocket 861b, directed axially along the slot 861a, and released or otherwise placed in another pocket 861b. In this alternative, a spring or other biasing mechanism (not shown) may bias the push button 862 and carriage 865 to direct the cap 862b into any pocket 861b with which the cap 862b is aligned when the cap 862b is released.

In an exemplary embodiment, the handle 860 may include three pockets 861b, e.g., one corresponding to the first position of the inner member 130,' one corresponding to the second position, and one corresponding to the third position. Thus, to place the inner member 130' in any of the first, second, or third positions, the cap 862b may be directed out of a pocket within which the cap 862b is received, the push button 862 may be slid axially along the slot 861a, and released or otherwise directed into the desired pocket 861b. Alternatively, the handle 860 may include only one or two pockets 861b, e.g., if the push button 862 is biased axially to one of the positions.

During use, the push button 862 may be directed axially in a first direction, e.g., distally to the indicator "R" in FIG. 24C, and released or captured in a corresponding pocket, thereby translating the inner member 130' distally to the first position to open the outlet 158.' Thus, fluid delivered through the outer member 120' may pass through the balloon 150' and exit the outlet 158,' as described above. The push button 862 may be directed out of the pocket and directed axially, e.g., proximally, to the indicator "N", thereby translating the inner member 130' proximally to the second position, e.g., until the sealing member 138' seals the outlet 158' to allow balloon expansion. In addition, if desired, the push member 872 may be directed out of the "N" pocket, axially within the slot 861*a*, and released in the third pocket, corresponding to indicator "D," thereby translating the inner member 130' to the third position, e.g., to expand the balloon 150' to the expanded helical shape, also as described above.

Turning to FIGS. 25A and 25B, still another embodiment of a handle 960 is shown that includes an outer housing 961 including a side port 964 (shown in FIG. 25A), a carriage (not shown) within the housing 961, and a hub 963 extending from the housing 961, generally similar to the previous embodiments. The carriage may include a rack 965 (shown in FIG. 25B) including a plurality of teeth 965*a* spaced apart axially along the rack 965.

The proximal end (not shown) of the inner member 130' may be substantially fixed relative to the carriage (not shown) such that axial movement of the inner member 130' is coupled to movement of the carriage and consequently to the rack 965, similar to the previous embodiments.

The hub 963 may include a hypotube or other tubular member (not shown) and a Luer lock or other connector 963*b* secured to one another and/or to the outer housing 961, similar to the previous embodiments. The tubular member may be slidably received in a passage in the carriage, e.g., such that the connector 963*b* remains substantially stationary relative to the housing 961 (and inner member 130') as the carriage is directed axially.

In this embodiment, the actuator is a rotary wheel 962 rotatably mounted to the housing 961, as shown in FIG. 25A. The rotary wheel 962 includes an outer wheel 962*a* including ridges or other features to facilitate engaging and/or rotating the rotary wheel 962, and a pinion 962*b* that extends into the housing 961. As best seen in FIG. 25B, teeth on the pinion 962*b* may interlock with the teeth 965*a* on the rack 965 such that rotation of the outer wheel 962*a* causes the rack 965, and consequently, the inner member 130,' to move axially relative to the housing 961 and outer member 120.' Optionally, the housing 961 may include one or more visual indicators, e.g., for identifying the position of the inner member 132' when the wheel 962*a* is rotated to one or more orientations, similar to the previous embodiments.

During use, the rotary wheel 962 may be rotated in a first direction, e.g., to translate the inner member 130' distally to the first position to open the outlet 158.' When desired, the rotary wheel 962 may be rotated in a second opposite direction to translate the inner member 130'proximally to the second position and/or third position, e.g., to allow inflation of the balloon 150' and/or expanding the balloon 150' to the expanded helical shape, similar to the previous embodiments. One advantage of the rotary wheel 962 is that the ratio of the outer wheel 962*a*, pinion 962*b*, and teeth 965 on the rack 965 may be designed to provide a desired mechanical advantage and/or precision of movement of the inner member 130.'

Another embodiment of a handle 1060 is shown in FIGS. 26A and 26B that may be included in any of the apparatus shown herein. Similar to the previous embodiments, the handle 1060 includes a housing 1061 including a hub 1063 and a side port 1064. In this embodiment, the actuator is a squeeze button 1062 that may be depressed to direct the inner member 130' axially. e.g., from a first position to a second position, similar to the embodiments described elsewhere herein. Generally, when the squeeze button 1062 is pressed inwardly, links 1062*a*, 1062*b* defining the button 1062 are flattened out, thereby directing the proximal link 1062*a* proximally if the distal link 1062*b* is fixed axially relative to the housing 1061.

For example, a first end of the distal link 1062*b* may be pivotally coupled to the housing 1061 and a second end pivotally coupled to a first end of the proximal link 1062. A second end of the proximal link 1062*a* may be slidable axially along the housing 861, e.g., within a slot or track (not shown). With the second end of the proximal link 1062*a* coupled to the inner member 130,' e.g., by a cable or other linkage 1062*c*, as the squeeze button 1062 is pressed inwardly, the proximal link 1062 pulls the inner member 130,' e.g., from a first position (with the outlet 158' open) to a second position (allowing the balloon 158' to be inflated and/or expanded to the expanded helical shape).

Optionally a cover (not shown) may be placed over the squeeze button 1062 to protect the user from catching anything between the links 1062*a*, 1062*b*. In addition or alternatively, the squeeze button 1062 may be provided on the top of the housing 1061 (as shown), e.g., to allow a user to actuate the squeeze button 1062 with their thumb, or on the bottom of the housing 1061 (not shown), e.g., to allow a user to actuate the squeeze button 1062 with their index finger. Optionally, the handle 1060 may include one or more features (not shown) to allow the squeeze button 1062 to be releasably secured at one or more positions before the links 1062*a*, 1062*b* are completely flattened, e.g., to allow the inner member 130' to be translated and fixed in different positions, e.g., successively in the second and third positions, similar to the previous embodiments.

Figure 8:
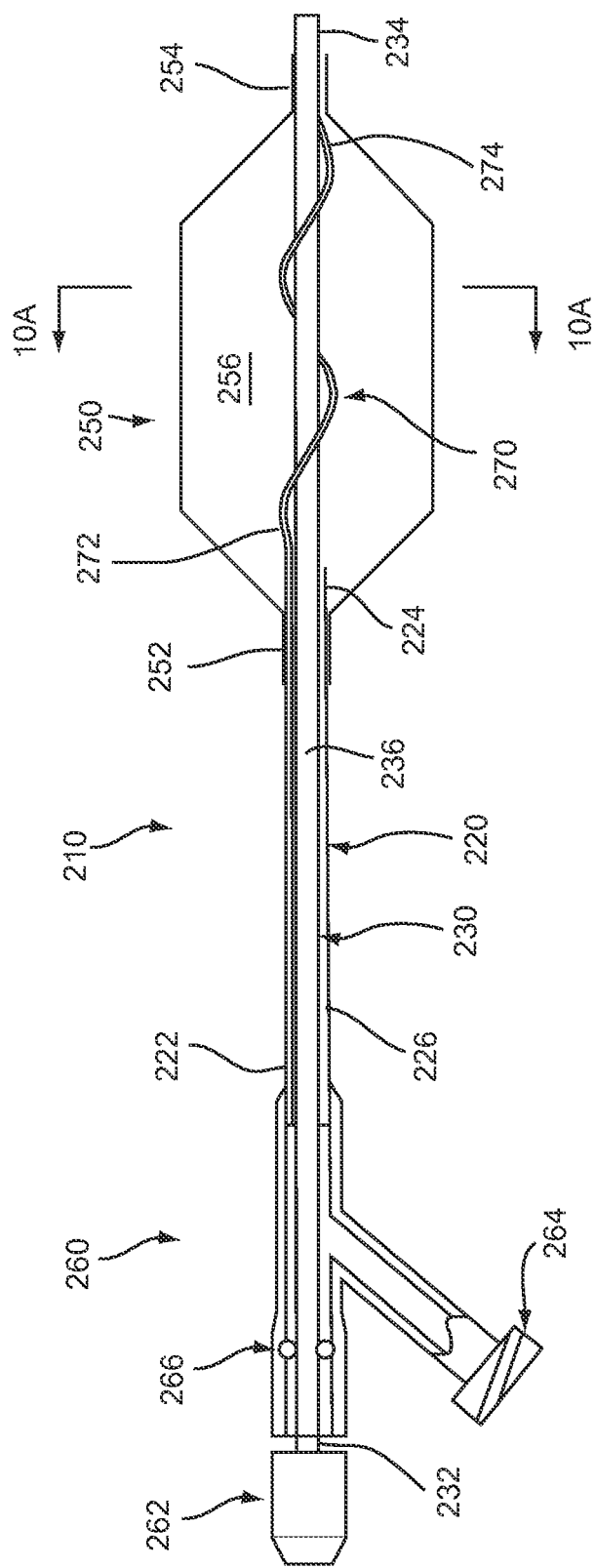
FIG. 8 is a side view of still another exemplary embodiment of an apparatus including a balloon for treating a body lumen, the apparatus operable in a first mode for dilating an obstruction within the body lumen, and a second mode for removing material within the body lumen.

Turning to FIG. 8, still another embodiment of an apparatus 210 is shown for treating a body lumen that generally includes an outer tubular member 220, an inner member 230, an expandable balloon 250, and helical member 270 carried by the inner and/or outer members 220, 230, similar to the previous embodiments, but does not include a valve for opening or closing an outlet in the balloon, unlike the embodiment of FIG. 7. The apparatus 110 may be operable in a first mode for dilating an obstruction within a body lumen, and/or a second mode for removing obstructive material within a body lumen, as described further below.

As shown, the outer member 220 includes proximal and distal ends 222, 224, and a first lumen 226 extending therebetween, and the inner member 230 also includes proximal and distal ends 232, 234, and a second lumen 236 extending therebetween. The inner member 230 is sized to be slidably received within the first lumen 226 of the outer member 220, e.g., such that an annular space is defined between the outer and inner members 220, 230 for passing one or more fluids therethrough, also similar to the previous embodiments.

A handle or hub 260 may be coupled to or otherwise provided on the proximal end 222 of the outer member 220, e.g., including a pull handle or other actuator 262 for moving the inner member 230 relative to the outer member 220, a side port 264 for coupling one or more fluid sources to the apparatus 210, and an o-ring or other seal 166 between the outer and inner members 220, 230, which may also be similar to the previous embodiments.

The balloon 250 includes a proximal end 252 coupled to the outer member distal end 224, a distal end 254 coupled to the inner member distal end 234, e.g., attached by bonding with adhesive, interference fit, sonic welding, fusing, and the like, similar to the previous embodiments. The balloon 250 may be formed from substantially inelastic material, e.g., to provide a non-compliant balloon that expands to a predetermined size when inflated independent of pressure, or alternatively, the balloon 250 may be formed from elastic material, similar to the other embodiments described elsewhere herein.

Also similar to the embodiment of FIG. 7, the helical member 270 may be coupled between the outer and inner members 220, 230. Thus, the helical member 270 may be movable from a relatively low profile, such as that shown in FIG. 8, to an expanded helical shape, as described further below with reference to FIGS. 9A-9D. As shown in FIG. 8, a first end 272 of the helical member 270 may be attached or otherwise secured directly to the distal end 224 of the outer member 220 and a second end 274 of the helical member 270 may be attached or otherwise secured to the distal end 234 of the inner member 230 adjacent the balloon distal end 252.

Figure 9A:
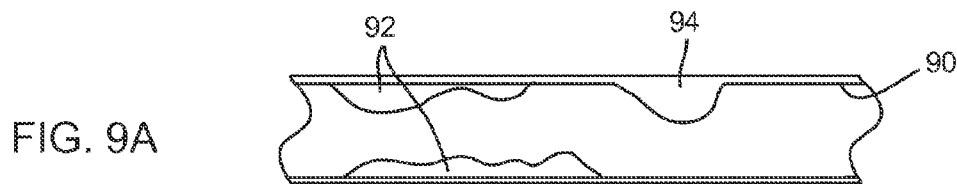
FIGS. 9A-9G are cross-sections of a body lumen showing exemplary methods for removing thrombus or other obstructive material from the body lumen and/or for dilating an obstruction within the body lumen using the apparatus of FIG. 7 or 8.
Figure 9B:
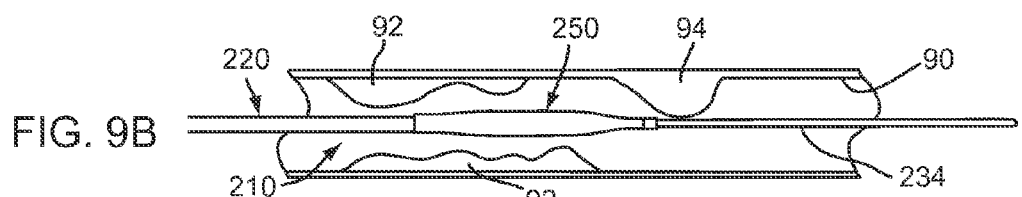
Figure 9C:
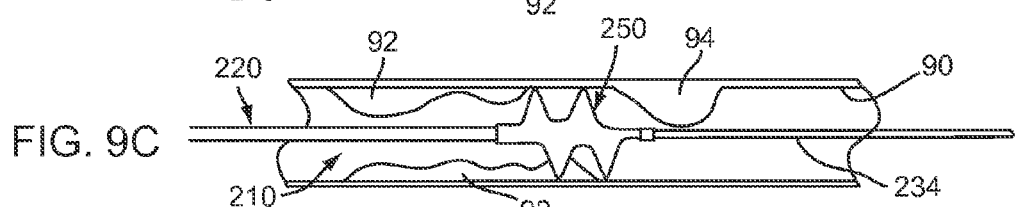
Figure 9D:
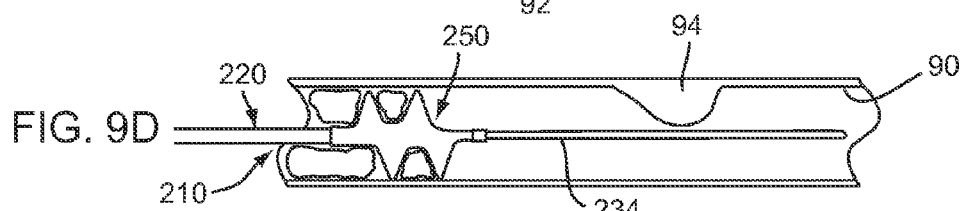

During use, in the exemplary methods shown in FIGS. 9A-9G, the apparatus 210 may be used for treating a body lumen 90, e.g., for removing obstructive material 92 and/or dilating an obstruction 94 within a body lumen 90, e.g., as shown in FIG. 9A. Similar to the previous embodiments, the target body lumen 90 may be a blood vessel, e.g., a vein or artery, a graft, e.g., an aorto-venous fistula, tubular xenograft, or synthetic tubular graft, and the like.

Optionally, the body lumen may be accessed using one or more additional instruments (not shown), which may be part of a system or kit including the apparatus 210, e.g., including one or more introducer sheaths, guide catheters, and/or guidewires (not shown). For example, to facilitate directing the apparatus 210 from an entry site to the target body lumen, a guide catheter, micro-catheter, introducer sheath, or other tubular body (not shown) may be placed from the entry site to the body lumen 90 using conventional methods. In addition or alternatively, a guidewire (not shown) may be placed from the entry site to the body lumen 90 if desired.

Initially, with reference to FIG. 9B, the apparatus 210 may be advanced into the body lumen 90 with the inner member 230 in the first or distal position, e.g., such that the balloon 250 is substantially collapsed. Optionally, contrast or other fluid may be delivered into the body lumen 90, e.g., via the second lumen 236 in the inner member 230 (not shown, see FIG. 8) or via a separate lumen (not shown) in the outer member 220. Markers (not shown) on the apparatus 10 may facilitate positioning the balloon 250 relative to the material 92 intended to be removed, e.g., to position the balloon 250 beyond or otherwise adjacent the material 92.

Optionally, the apparatus 210 may be introduced through a guide catheter or other tubular member (not shown) that includes a lumen communicating with a source of vacuum. With the balloon 250 disposed beyond the guide catheter, the source of vacuum may be activated to aspirate material within the body lumen 90, e.g., as the material 92 is dislodged or otherwise removed by the balloon 250, as described below.

Turning to FIG. 9C, the inner member 230 may be directed proximally relative to the outer member 220, thereby causing the helical member 270 and consequently the balloon 250 to expand towards the expanded helical shape, as described above. As shown in FIG. 9D, the entire apparatus 210 may then be retracted to remove the material 92, e.g., scraping, scrubbing, or otherwise separating material that may be adhered to a wall of the body lumen 90. For example, the apparatus 210 may be pulled to remove the material 92 from the body lumen and into the lumen of the guide catheter, where the material 92 may be aspirated from the patient's body. Alternatively, the material 92 may be released in a manner such that the material 92 may be metabolized naturally by the patient's body.

If desired, the inner member 230 may be returned to the first position to collapse the balloon 250, and the apparatus 210 moved to another location within the body lumen 90. The inner member 230 may be directed between the first and second positions as often as desired to expand the balloon 250 and separate or otherwise remove sufficient material 92.

Figure 9E:
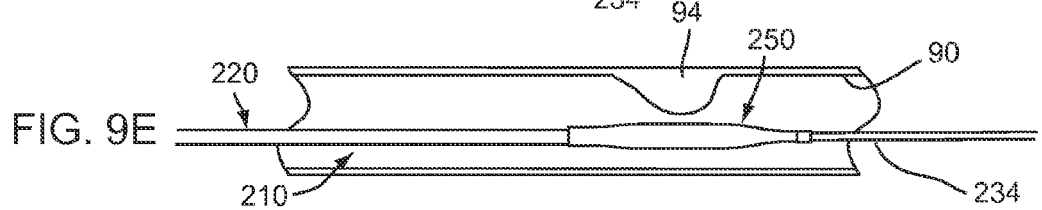
Figure 9F:
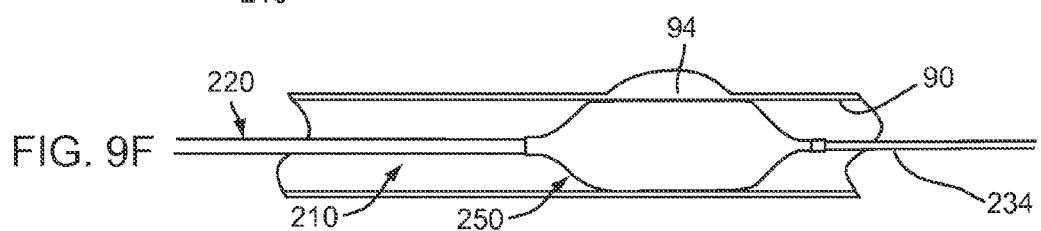
Figure 9G:

Turning to FIG. 9E, with sufficient material 92 removed, a stenosis, lesion, or other obstruction 94 is identified within the body lumen 90. The apparatus 210 may be reintroduced or repositioned in the body lumen 90 with the balloon 250 collapsed until the balloon 250 is positioned adjacent the obstruction 94, e.g., using fluoroscopy or other additional imaging. Once properly positioned, as shown in FIG. 9F, the balloon 250 may be inflated to dilate and/or otherwise treat the obstruction 94. Optionally, the balloon 250 may carry one or more diagnostic and/or therapeutic agents, which may be delivered against and/or into the obstruction 94 using the balloon 2500. After sufficient treatment, the balloon may be deflated, and the apparatus 10 removed from the body lumen 90, as shown in FIG. 9G.

Optionally, with any of the embodiments described herein, various balloon configurations may be provided. For example, turning to FIG. 10A, with additional reference to the apparatus 250 of FIG. 8, an exemplary cross-section of the apparatus 210, taken through the balloon 250, is shown. FIG. 10A shows the helical member 270 wound around the inner member 230 and surrounded by the expanded balloon 250. Thus, both the helical member 270 and the inner member 230 are disposed within the interior 256 of the balloon 250. One of the disadvantages of such a balloon 250 is that the wall must be relatively thick since it is difficult to predict which areas of the balloon wall are going to contact and scrape along a wall of a target body lumen.

FIGS. 10B-10D show alternative embodiments of balloon or tubular constructions that may be provided for any of the embodiments described herein. These constructions may be provided for a balloon capable of inflation or for a tubular member capable of expansion to an expanded helical shape without being inflated. Exemplary embodiments of such devices are disclosed in U.S. Pat. No. 4,762,130, the entire disclosure of which is expressly incorporated by reference herein.

For example, as shown in FIG. 10B, a balloon or tubular member 250' is shown that includes a first lumen 251' that receives the inner member 230 and a second lumen 253' that receives the helical member 270 therein. When the tubular member 250' and helical member 270 are compressed axially, the helical member 270 may expand radially outwardly away from the inner member 230, thereby directing surface region 280' radially outwardly away from the inner member 230 since the surface region 280' is furthest from the first lumen 251.' Thus, because the surface region 280' is likely to contact the wall of the body lumen when the tubular member 250' is expanded, the construction of the tubular wall may be varied to enhance scraping and/or other removal of obstructive material. For example, features may be integrally molded or otherwise formed in the wall of the tubular member 250,' e.g., that extend helically around the tubular member 250' adjacent the second lumen 253.'

As shown in FIG. 10B, the surface region 280' may include a plurality of grooves that provide edges 282' that may facilitate scraping adherent material from the wall of the target body lumen, e.g., by concentrating contact forces with the wall of the body lumen. In addition, the tubular wall opposite the surface region 280' may be relatively thin since this area of the wall is unlikely to contact the wall of the body lumen, which may allow an overall cross-section or profile of the tubular member 250' to be reduced. Alternatively, or in addition, if desired, different property materials may be used, e.g., harder elastomeric materials with relatively thinner wall thickness for the surface region 280' or elsewhere on the tubular member 250.'

Turning to FIG. 10C, another embodiment of a tubular member 250" is shown that includes ridges or protrusions 282" along surface region 280" that will contact the wall of the body lumen when the tubular member 250" is expanded. In a further alternative, shown in FIG. 10D, a tubular member 250''' may be provided that includes a first lumen 251''' having convolutions molded or otherwise formed into the tubular wall. The convolutions may increase the circumferential length of the tubular wall, and therefore allow the wall to stretch to a greater radial dimension, yet still direct the surface region 280''' towards the wall of a body lumen being treated.

Figure 11:
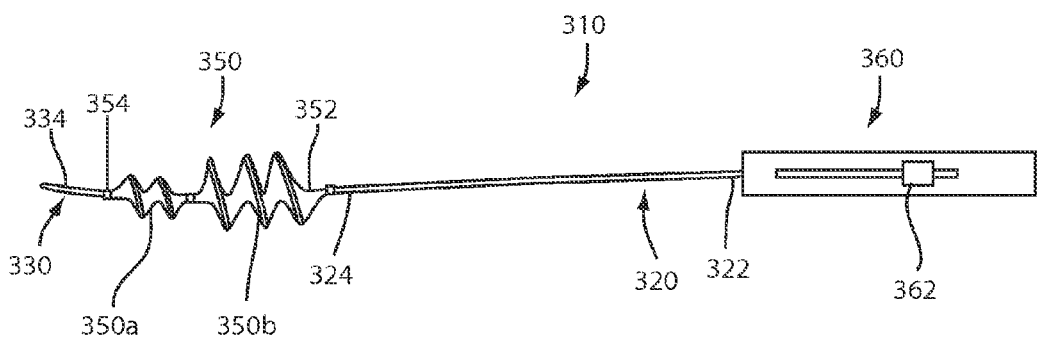
FIG. 11 is a side view of an alternative embodiment of the apparatus of FIG. 7 or 8, including an obstruction removal balloon having different size coils in different regions of the balloon.

Turning to FIG. 11, another embodiment of an apparatus 310 is shown that includes an outer member 320, an inner member 330, and an expandable member 350 carried on distal ends 324, 334 of the outer and inner members 320, 330, similar to the previous embodiments. Unlike the previous embodiments, the expandable member 350 may not include an interior coupled to a lumen extending through the outer member 320, i.e., the expandable member 350 may not be inflatable. However, alternatively, if desired, the apparatus 310 may include a lumen (not shown) extending through the outer member 320 and communicating with an interior of the expandable member 350 for selectively inflating or collapsing the expandable member 350. In addition, if desired, the apparatus 310 may include one or more sealing members or other valve (not shown) that may be opened or closed for selectively infusing fluid or inflating the expandable member 350, similar to the previous embodiments.

The expandable member 350 generally includes a proximal end 352 coupled to the outer member distal end 324 and a distal end 354 coupled to the inner member distal end 334, e.g., by bonding with adhesive, sonic welding, fusing, interference fit, one or more bands or other connectors (not shown), and the like. In addition, the apparatus 310 includes a helical member (not shown) that may also be coupled between the outer member and inner member distal ends 324, 334 and extend helically around the inner member 330, e.g., within the interior of or otherwise carried by the expandable member 350, similar to the previous embodiments.

For example, the helical member may be loose within the interior of the expandable member 350. Alternatively, the helical member may be embedded in or otherwise attached to the wall of the expandable member 350, e.g., to an inner surface of the expandable member 350.

Unlike the previous embodiment, the helical member includes a first coil within a first region 350*a* of the expandable member 350 and a second coil within a second region 350*b* of the expandable member 350 having different properties. The first and second coils may be coupled to one another, e.g., integrally formed together as a single wire, filament, and the like, or may be formed as separate wires or filaments attached to one another. Each coil includes a plurality of turns that extend helically around the inner member 330, e.g., between the proximal and distal ends 352, 354 of the expandable member 350.

The coils may be provided in a relatively low profile around the inner member 330, e.g., when the inner member 330 is extended distally relative to the outer member 320 to a first position. When the inner member 330 is retracted proximally from the first position towards a second position, the coils may be compressed axially, thereby causing the coils to expand radially outwardly and expand the expandable member 350 radially outwardly to an expanded helical shape, similar to the previous embodiments.

The coils may have different mechanical properties from one another, thereby causing the first and second regions 350*a*, 350*b* of the expandable member 350 to expand to different sizes and/or shapes in the expanded helical shape. For example, as shown in FIG. 11, the first region 350*a* may be expanded to a smaller diameter than the second region 350*b*. This may be achieved by forming the first coil from thinner, narrower, or otherwise more flexible material than the second coil. In addition or alternatively, the coils may be biased to different diameters such that when the inner member 330 is in the distal or first position, the coils may be constrained in the low profile, and when the inner member 330 is directed proximally towards the second position, the coils may resiliently expand radially outwardly to the diameters set into the coil material.

In addition or alternatively, the coils may be expandable sequentially, e.g., such that the first region 350*a* of the expandable member 350 may expand to the expanded helical shape before the second region 350*b*. For example, the first coil in the first region 350*a* may have less resistance to expansion than the second coil in the second region 350*b*, e.g., by forming the first coil from thinner, narrower, and/or otherwise more flexible material than the second coil. For example, the first coil may include a bare wire wound helically around the inner member 330, while the second coil may include the same or different wire wrapped in a section of tubing, a sleeve, and the like, which may increase resistance to expansion. Thus, when the inner member 330 is directed from the first position towards the second position, the compressive force may be applied initially to the first coil, thereby expanding the first coil and the first region 350*a* of the expandable member 350, until a predetermined threshold is achieved, whereupon the second coil may expand and expand the second region 350*b* of the expandable member 350.

In another alternative, a sleeve (not shown) attached to the inner member 330 may initially surround the second coil in the first position such that only the first coil is free to expand when initially compressed. When the inner member 330 is directed towards the second position, the second coil may become exposed from the sleeve, and then expand radially outwardly to the expanded helical shape.

Figure 12:
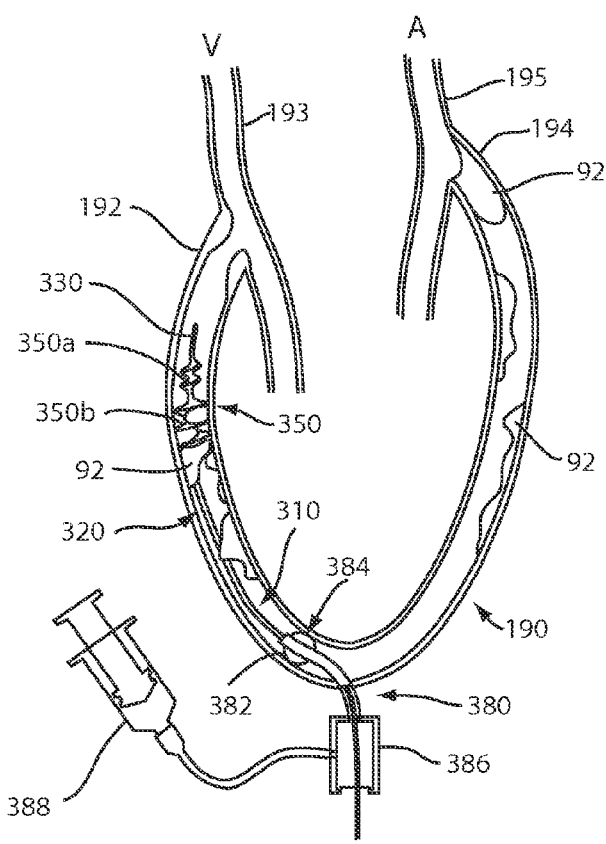
FIGS. 12 and 13 are cross-sectional views of a patient's body, showing methods for treating an arterio-venous dialysis graft using the apparatus of FIG. 11.
Figure 13:
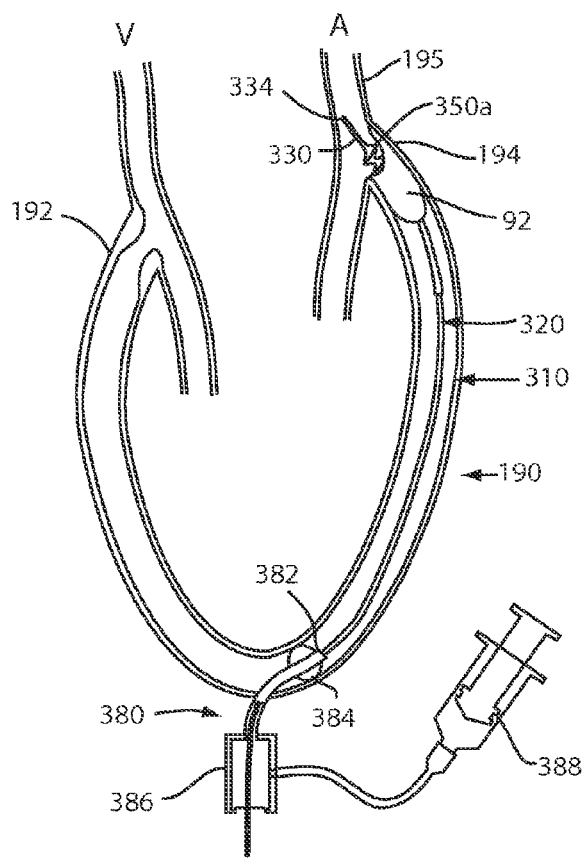

Turning to FIGS. 12 and 13, an exemplary method is shown for treating a body lumen, e.g., a arterio-venous dialysis graft 190, using the apparatus 310 of FIG. 11. As shown, the graft 190 includes a first or venous anastomosis 192 attached to a vein 193 within a patient's body, e.g., within the patient's arm, and a second or arterial anastomosis 194 attached to an artery 195 adjacent the vein 193. As shown, the graft 190 includes obstructive material 92, e.g., thrombus, plaque, and the like at multiple locations in the graft 190 including within each anastomosis 192, 194.

Initially, an introducer or guide sheath 380 may be placed within the graft 190, e.g., percutaneously through the patient's skin into a central region of the graft 190, using similar methods to those described elsewhere herein. The sheath 380 may include a distal end 382 having a size and/or shape for introduction into the graft 190 and a balloon 382 on the distal end 384 for substantially engaging a wall of the graft 190, e.g., to stabilize the sheath 380 relative to the graft 190 and/or to substantially seal the graft 190 from fluid flow between the ends 192, 194 of the graft 190. The sheath 380 may also include a reservoir 386 communicating with a lumen extending to an opening (not shown) in the distal end 382, and a source of vacuum 388, e.g., a syringe, for applying a vacuum to aspirate material from within the graft 190 during treatment.

The apparatus 310 may be introduced through the sheath 380 into the graft 190 with the expandable member 350 initially in a contracted condition. As shown in FIG. 12, the apparatus 310 may be advanced until the expandable member 350 is disposed distally beyond obstructive material 92 within the venous side of the graft 190, whereupon the inner member 330 (not shown) may be directed proximally to expand the expandable member 350 to the expanded helical shape. As shown, both coils have been expanded, thereby expanding both the first and second regions 350a, 350b of the expandable member 350, e.g., such that the second region 350b may substantially engage or otherwise contact the wall of the graft 190.

The apparatus 310 may then be withdrawn to scrape or otherwise separate adherent material 92 from the wall of the graft 190 and pull the material 92 towards the sheath 380. The source of vacuum 388 may be activated, if not already, to aspirate the material 92 through the sheath 380 into the reservoir 386. If desired, the inner member 330 may be advanced to collapse the expandable member 350 back towards the contracted condition and advanced further into the graft 190, e.g., to repeat the process of expanding the expandable member 350 to scrape or otherwise remove material 92.

Optionally, the sheath 380 may be repositioned within the graft 190 towards the arterial anastomosis 194, and the apparatus 310 reintroduced with the expandable member 350 in the contracted condition, e.g., to remove material 92 within the arterial side of the graft 190. Turning to FIG. 13, although material has been removed from the graft 190, additional obstructive material 92 remains within the arterial anastomosis 194. Because the anastomosis 194 communicates with the artery 195, care should be taken to ensure that material is not released into the artery 195, where the material may flow into tissue beds, cause ischemia, or other damage to tissue downstream of the artery 195.

The apparatus 310 may be advanced until the distal end 334 of the inner member 330 passes through material 92 within the arterial anastomosis 194 with the expandable member 350 in the contracted condition. At this point, the inner member 330 may be directed proximally sufficient distance to expand the first region 350a of the expandable member 350 without substantially expanding the second region 350b. The apparatus 310 may then be withdrawn to pull the expandable member 350 back towards the sheath 380, where any material 92 removed from the anastomosis 194 may be aspirated out of the graft 190. Thus, the smaller first region 350b may allow greater care to be used to remove material from sensitive regions, while the second region 350b may be expanded within relatively large body lumens or otherwise when it is desired to apply greater force and/or remove greater amounts of material.

Figure 14:
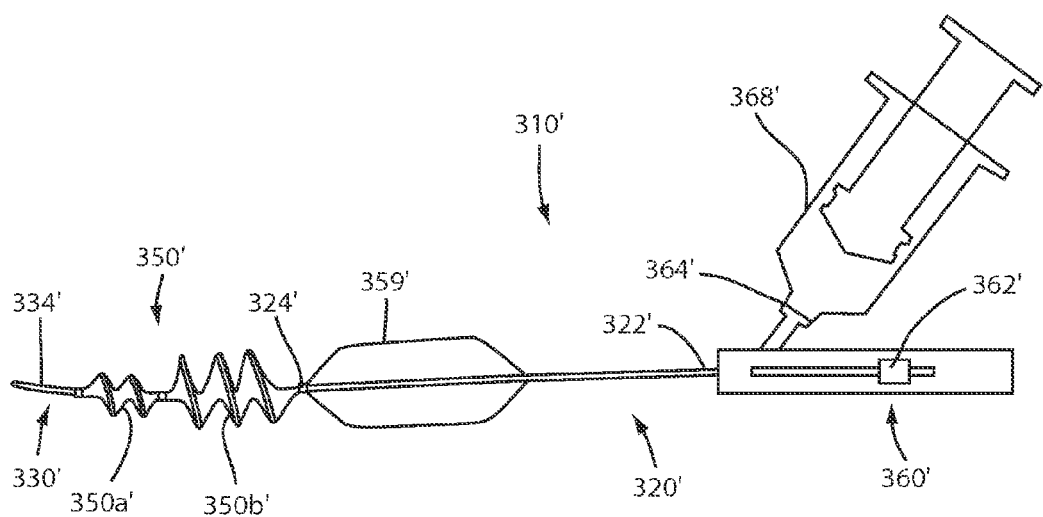
FIG. 14 is a side view of another alternative embodiment of the apparatus of FIG. 11, including a dilation balloon adjacent the obstruction removal balloon.

Turning to FIG. 14, an alternative embodiment of the apparatus 310 shown in FIG. 11 is shown. The apparatus 310' of FIG. 14 is generally the same as apparatus 310, e.g., including an outer member 320,' an inner member 330,' an expandable member 350,' and first and second coils defining a helical member within the expandable member 350,' similar to the previous embodiments. Unlike the previous embodiment, the apparatus 310' includes a dilation balloon 359,' e.g., a substantially non-compliant, high pressure balloon, on the outer member distal end 324.' In addition, the apparatus 310' includes a handle 360' that includes a side port 364' to which a source of inflation media and/or vacuum 368' may be connected.

The apparatus 310' may be used similar to the apparatus 310 shown in FIG. 11, e.g., using the methods of FIGS. 12 and 13. In addition, the dilation balloon 359' may be positioned within a stenosis, lesion, or other obstruction, e.g., in the graft 190 of FIGS. 12 and 13, or within other body lumens. The balloon 359' may then be inflated or otherwise expanded to dilate the body lumen, similar to other embodiments described above. Optionally, a stent or other prosthesis (not shown) may be carried by the balloon 359,' e.g., such that the prosthesis may be implanted within a body lumen after using the balloon 350' to remove obstructive material from the body lumen. Alternatively, a stent or other prosthesis may be carried and delivered using any of the other embodiments described herein, e.g., on the balloon 150 or 250 of the apparatus 110 or 210, shown in FIG. 7 or 8.

Figure 14A:
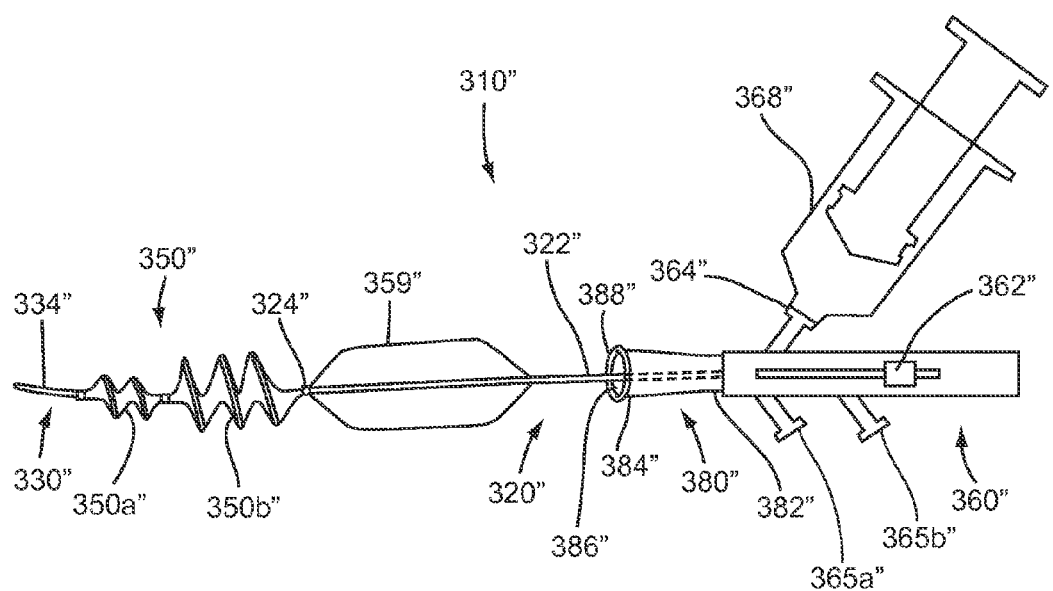
FIG. 14A is a side view of another alternative embodiment of the apparatus of FIG. 11, including

In another option, shown in FIG. 14A, an apparatus 310" may be provided that is generally similar to the apparatus 310' of FIG. 14. Unlike the apparatus 310,' the apparatus 310" also includes an outer sheath 380" at least partially surrounding the outer member 320." For example, as shown, the outer sheath 380" may include a proximal end 382" attached to the handle or otherwise disposed around the proximal end 322" of the outer member 320" and a distal end 384" extending distally to a location adjacent the distal end 324" of the outer member 320," e.g., proximal to balloon 359." The outer sheath 380" may have a diameter or other cross-section larger than the outer member 322" such that an annular lumen 386" is provided between the outer sheath 380" and the outer member 320." The lumen 386" may communicate with a side port 365a" on the handle 360," which may include a Luer fitting or other connector. Thus, a syringe or other source of vacuum (not shown, e.g., similar to syringe 368") may be coupled to the side port 365a" and used to aspirate material adjacent the balloon 359" through the lumen 386." In addition or alternatively, a source of lytic agent and/or one or more other agents (also not shown) may be coupled to the side port 365a" and the agent(s) may be delivered through the annular lumen 386" into the body lumen instead of or in conjunction with aspiration.

In addition, the apparatus 310" includes an annular balloon or other expandable member 388" on the distal end distal end 384" of the outer sheath 380." The outer sheath 380" may include an inflation lumen (not shown), e.g., extending proximally along the wall of the outer sheath 380" to the proximal end 382," and communicating with another side port 365b," which may include a Luer fitting or other connector, similar to the side port 365a" to which a syringe or other source of inflation media (not shown, e.g., similar to the syringe 368") may be coupled.

During use, the outer sheath 380" may be provided around the outer member 320" when the apparatus 310" is introduced into a body lumen, e.g., similar to other embodiments herein. Optionally, the distal end 384" of the outer sheath 380" may be tethered or otherwise coupled to the outer sheath 380'" to prevent proximal migration of the distal end 384" during advancement of the apparatus 310." In addition or alternatively, the annular balloon 388" may have a collapsed configuration that frictionally and/or otherwise engages the outer member 320" to prevent migration of the distal end 384" of the outer sheath 380."

Once the apparatus 310" is positioned within a body lumen (not shown) being treated, e.g., by the balloon 350" and/or balloon 359," the annular balloon 388" may be expanded, e.g., to engage the surrounding wall of the body lumen and/or to open the distal end 384" of the outer sheath 380." The annular balloon 350" may be formed from elastic material and/or inelastic material, e.g., that allows the annular balloon 350" to radially expand and substantially engage the surrounding wall to provide a seal, e.g., that may stop substantially all flow through the body lumen or simply prevent substantial migration of loose material within the body lumen. At any time, vacuum may be applied to the annular lumen 386" of the outer sheath 380," e.g., to aspirate or otherwise remove material separated from the wall of the body lumen (not shown) through the lumen 386."

Optionally, the outer sheath 380" may be formed from substantially flexible material, e.g., to allow the outer sheath 380" to be compressed and/or extended axially, e.g., if the apparatus 310" is moved axially and/or radially while the annular balloon 380" is engaged with the wall of body lumen. Thus, material separated from the wall of the body lumen may be directed towards the annular lumen 386," e.g., using the balloon 350" or 359" and aspirated through the annular lumen 386" from the body lumen.

Alternatively, if the outer sheath 380'" has a substantially fixed length, the annular balloon 380" may be include lubricious material that allows the balloon 380" to slide along the wall of the body lumen when the apparatus 310" is directed axially while maintaining a seal with the wall to reduce the risk of loose material within the body lumen from escaping and traveling to other locations within the patient's body. In this alternative, the aspiration vacuum may be sufficient to draw loose material from the body lumen without pushing the material towards the annular lumen with one of the balloons 350," 359."

In another alternative, at least the distal end 384" of the outer sheath 380" may be radially expandable, e.g., such that the outer sheath 380" may be provided in a collapsed configuration around the outer member 320," e.g., during introduction of the apparatus 310," yet may be expanded to open the annular lumen 386" to allow material to be aspirated from the body lumen through the annular lumen 386." In this alternative, the annular balloon 380" may be omitted. It will be appreciated that an outer sheath and/or annular balloon may be provided on other embodiments herein, e.g., to facilitate aspiration of material and/or reduce the risk of migration of material released within a body lumen during treatment.

Figure 15A:
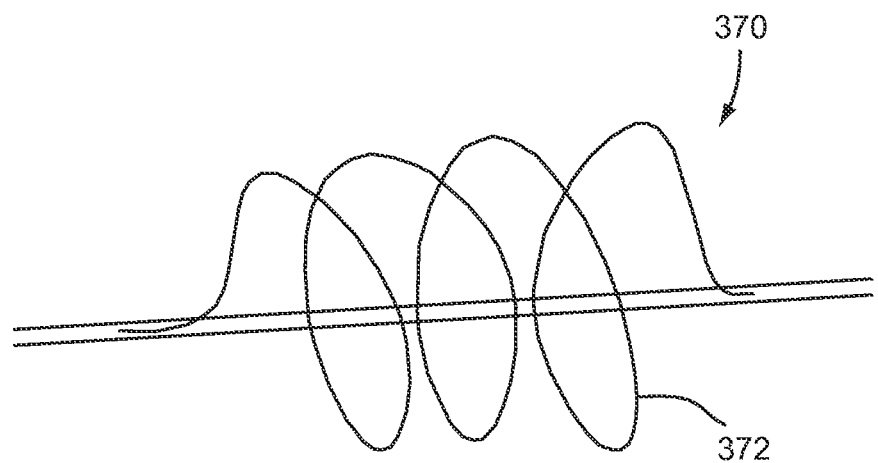
FIGS. 15A and 15B are alternative embodiments of coil structures that may be provided within the balloon of any of the apparatus of FIGS. 8-14.
Figure 15B:
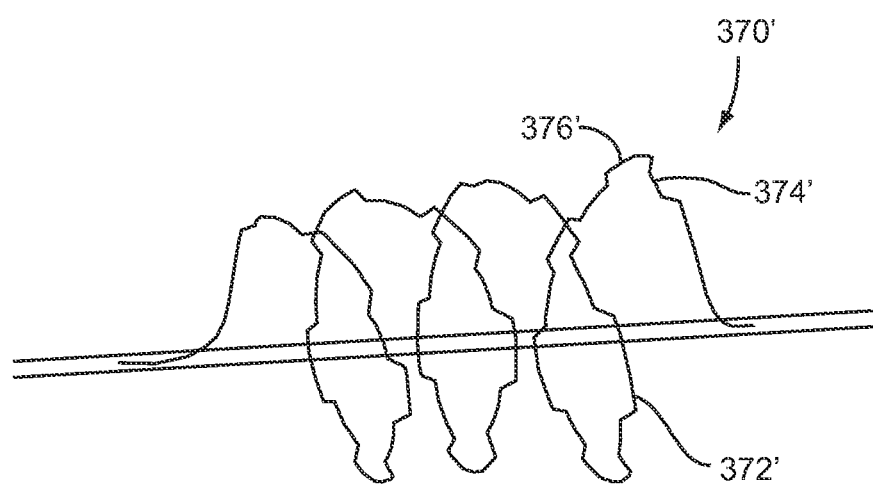

Turning to FIGS. 15A and 15B, exemplary embodiments of coils are shown that may be included in any of the apparatus described herein including a helical member for expanding a balloon or other expandable member to an expanded helical shape. For example, FIG. 15A shows a coil 370 that includes substantially smooth, uniform turns 372 that may be incorporated as a helical member in any of the apparatus described above. Alternatively, as shown in FIG. 15B, a coil 370' may be provided that includes a plurality of turns 372' having alternating high points 374' and low points 376' that may increase contact force with a wall of a body lumen when the coil 370' is included within a balloon or expandable member (not shown), such as those described elsewhere herein. The high and low points 374,' 376' may be staggered between adjacent turns, e.g., to ensure that at least some high points 374' contact and/or scrape along substantially the entire circumference of a wall of a target body lumen.

Figure 16:
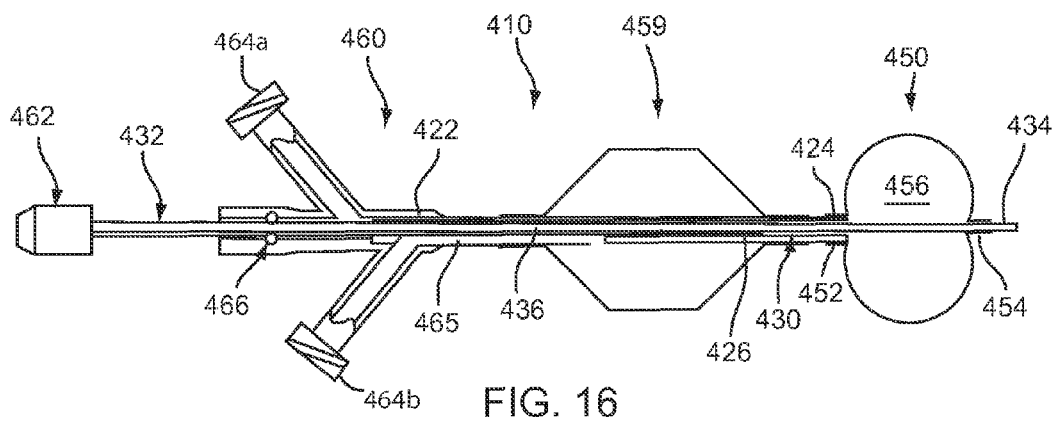
FIG. 16 is a side view of yet another exemplary embodiment of an apparatus including a balloon for treating a body lumen, the apparatus operable in a first mode for removing material within the body lumen, and in a second mode for dilating an obstruction within the body lumen.

Turning to FIG. 16, still another embodiment of an apparatus 410 is shown that includes multiple expandable devices on a single shaft, e.g., such that the apparatus 410 may be operable in multiple modes, e.g., a first mode for removing material within a body lumen, and a second mode for dilating an obstruction within a body lumen.

Generally, the apparatus 410 includes an outer member 420, an inner member 430, a handle 460, and a first balloon or other expandable member 450 carried by the outer and inner members 420, 430, similar to the previous embodiments. The outer member 420 includes proximal and distal ends 422, 424, and a first lumen 426 extending therebetween, and the inner member 430 also includes proximal and distal ends 432, 434, and a second lumen 436 extending therebetween.

The first balloon 450 includes a proximal end 452 coupled to the outer member distal end 424 and a distal end coupled to the inner member distal end 434, and includes an interior communicating with the first lumen 426. The first balloon 450 may be formed from elastic material, e.g., such that the first balloon 450 may be expanded to a range of diameters and/or shapes, e.g., depending upon the volume of inflation media delivered into the interior of the first balloon 450 and/or the position of the inner member 430 relative to the outer member 420.

In addition, a second balloon 459 may be provided on the outer member 420, e.g., proximal to the first balloon 450. The second balloon 459 may be formed from substantially inelastic material, e.g., to provide a non-compliant, high pressure dilation balloon, similar to other embodiments described elsewhere herein. The outer member 420 includes a third inflation lumen 465 communicating with the interior of the second balloon 459.

As shown, the handle 460 includes a first side port 464a communicating with the first lumen 426 for delivering inflation media into the first balloon 450, and a second side port 464b communicating with the third inflation lumen 465 for delivering inflation media into the second balloon 459. In addition, the handle 460 may include a pull handle or other actuator 462 for directing the inner member 430 to one or more axial positions relative to the outer member 420, and one or more seals, e.g., o-ring 466 for sealing the first lumen 426, similar to the previous embodiments.

Figure 17A:
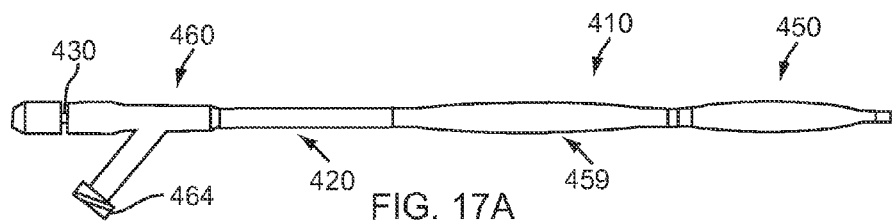
FIGS. 17A-17D are side views of the apparatus of FIG. 10, showing operation of the apparatus between an initial delivery configuration (FIG. 11A), the first mode for removing material within a body lumen (FIGS. 11B and 11C), and the second mode for dilating an obstruction within a body lumen (FIG. 11D).

Turning to FIGS. 17A-17D, the apparatus 410 is shown in different modes with the inner member 430 in respective positions. First, as shown in FIG. 17A, the inner member 430 is in a first or distal position with the first and second balloons 450, 459 in contracted conditions. In this configuration, the apparatus 410 may be introduced into a patient's body, into a target body lumen being treated, similar to the previous embodiments.

Figure 17B:
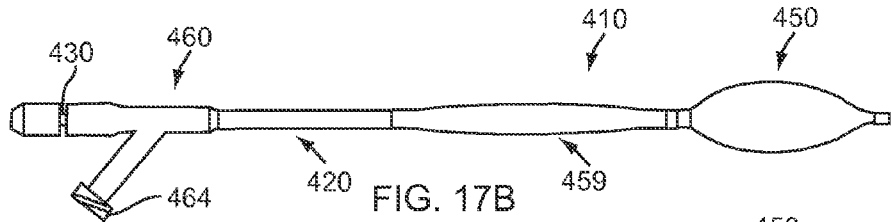
Figure 17C:
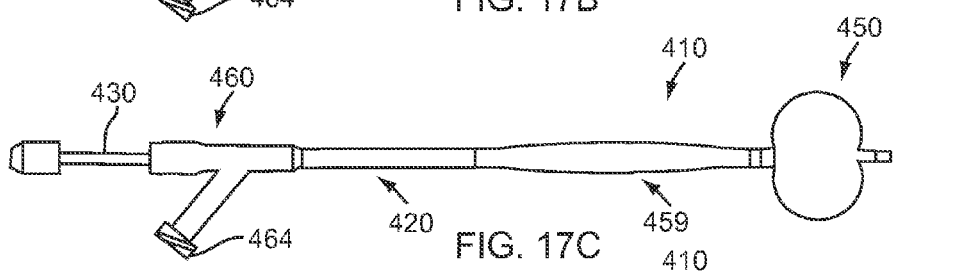

Turning to FIG. 17B, the first balloon 450 has been inflated to an expanded condition with the inner member remaining in the first position. Thus, the first balloon 450 may be expanded to one or more diameters, e.g., to engage or contact the wall of a body lumen being treated. The apparatus 410 may then be retracted or otherwise directed axially to scrape the first balloon 450 along the wall, e.g., to remove thrombus or other adherent material from the wall. Optionally, as shown in FIG. 17C, if greater pressure is desired, or a larger balloon is desired due to the size of the body lumen, the pull handle 462 may be directed proximally to pull the inner member 430 proximally relative to the outer member 420, thereby axially compressing and radially expanding the first balloon 450.

Figure 17D:
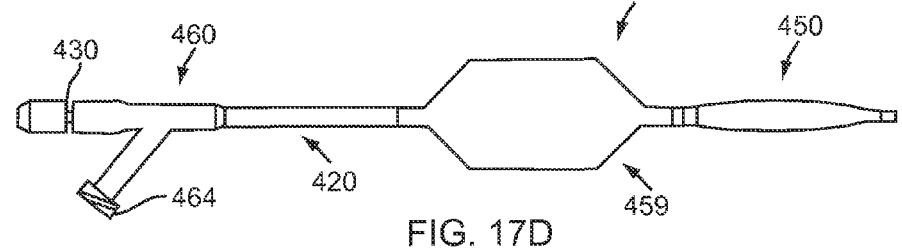

Finally, as shown in FIG. 17D, if it desired to dilate a stenosis, lesion, or other obstruction, the first balloon 450 may be collapsed to the contracted condition, and the second balloon 459 may be positioned adjacent the obstruction and inflated to expand and dilate the obstruction, similar to the previous embodiments. Thus, the apparatus 410 may be used for different treatments, e.g., embolectomy and/or angioplasty, without having to remove the apparatus 410, similar to the previous embodiments. The apparatus 410 may be tracked over a guidewire or other rail received through the second lumen 436 of the inner member 430, which may facilitate directing the apparatus 410 to various positions within a body lumen during treatment.

Figure 18A:
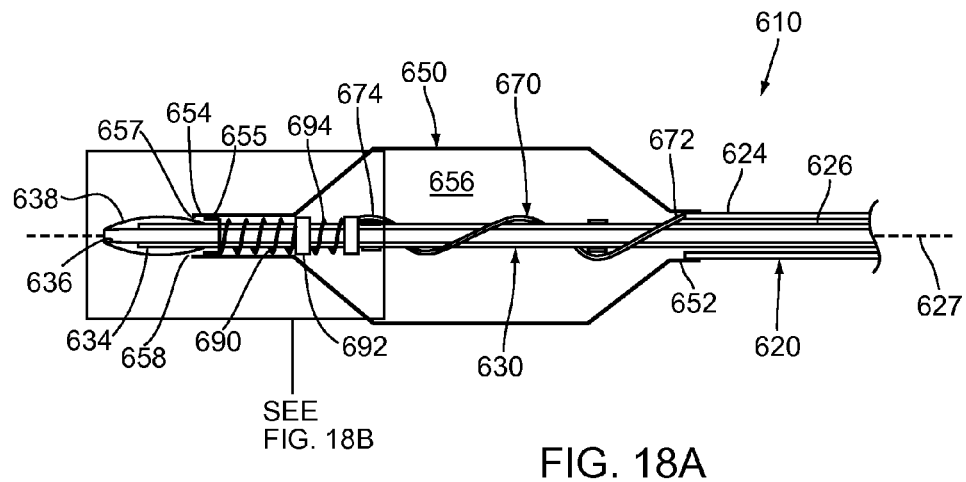
FIGS. 18A-18C are cross-sectional views of a distal end of another embodiment of an apparatus including a balloon for treating a body lumen, the apparatus operable in a first mode for dilating an obstruction within the body lumen, a second mode for infusing fluid into the body lumen, and a third mode for removing material within the body lumen.
Figure 18B:
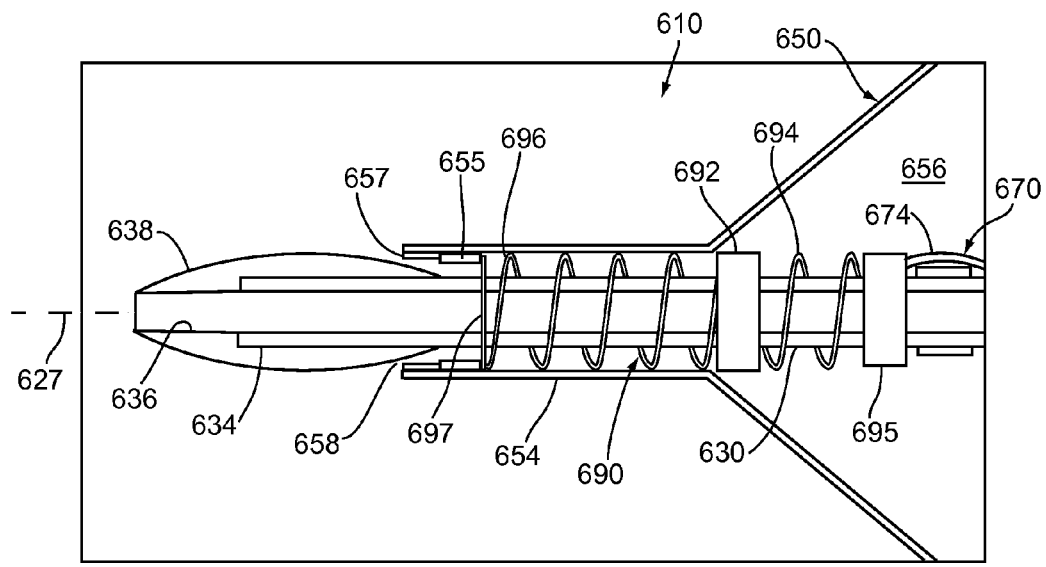
Figure 18C:
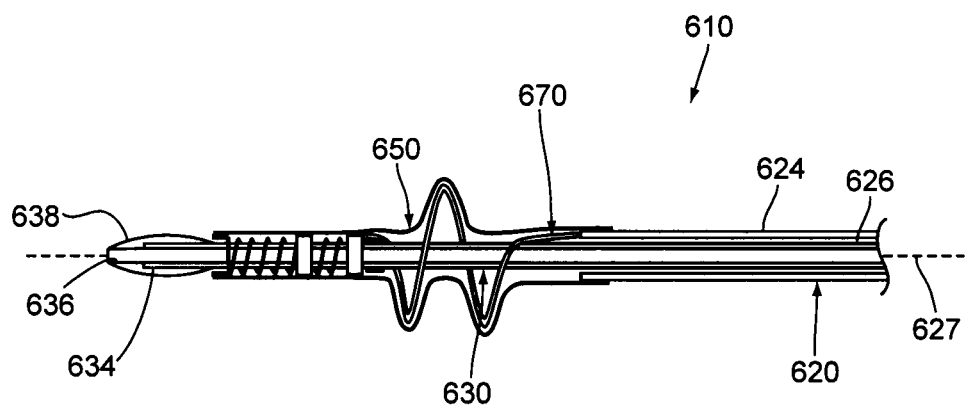
Figure 19A:
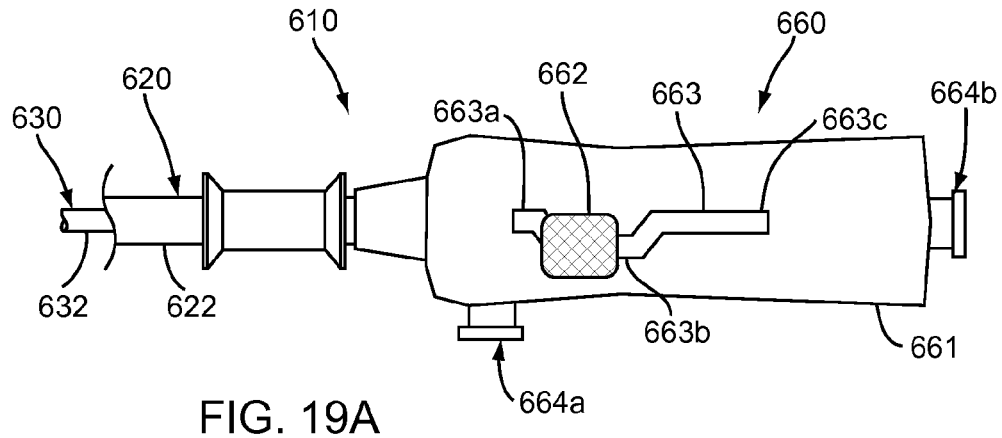
FIGS. 19A-19C are side views of a proximal end of the apparatus of FIGS. 18A-18C, showing an actuator on the proximal end directed between first, second, and third positions for operating the apparatus in the first, second, and third modes, respectively.
Figure 19B:
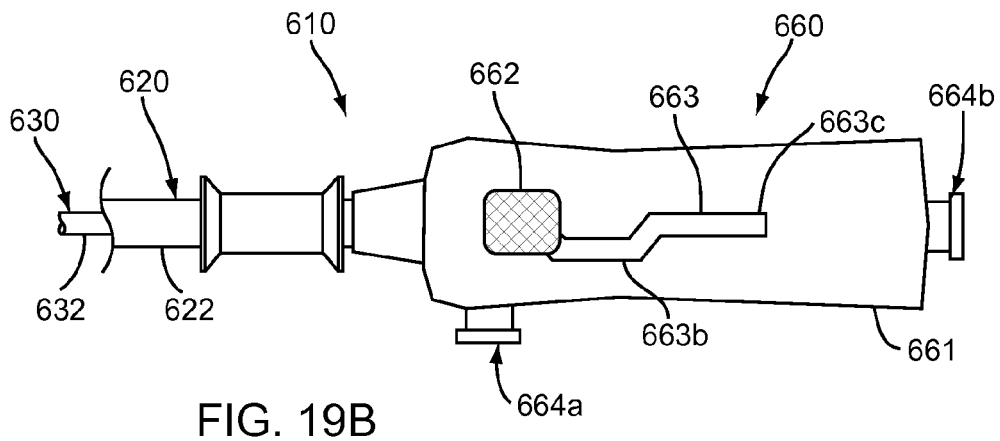
Figure 19C:
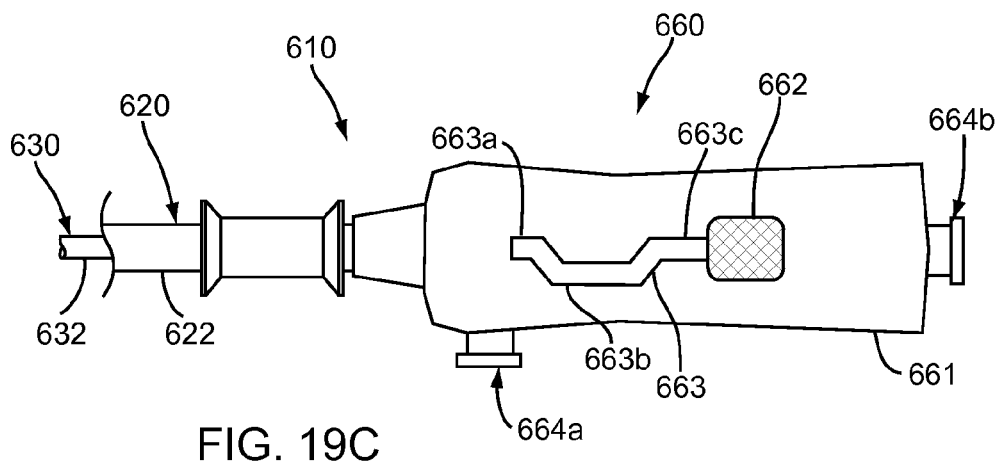

Turning to FIGS. 18A-18C, another embodiment of an apparatus 610 is shown for treating a body lumen that includes an outer tubular member 620, an inner member 630, and an expandable balloon 650 carried by the inner and/or outer members 620, 630, generally similar to the previous embodiments. In addition, as shown in FIGS. 19A-19C, the apparatus 610 may include a handle or hub 660 coupled to or otherwise provided on a proximal end 622 of the outer member 620, e.g., for manipulating the outer member 620 and/or the entire apparatus 610, generally similar to the previous embodiments. Also similar to previous embodiments, the apparatus 610 may be operable in multiple modes, e.g., a first mode for dilating an obstruction within a body lumen (FIGS. 18A, 19A), a second mode for infusing fluid into a body lumen (FIGS. 18B, 19B), and/or a third mode for removing obstructive material within a body lumen (FIGS. 18C, 19C), as described further below.

As shown, the outer member 620 includes a proximal end 622, a distal end 624 sized for introduction into a body lumen, and a first lumen 626 extending along a central longitudinal axis 627 therebetween, which may be constructed similar to the previous embodiments. The inner member 630 also includes a proximal end 632, a distal end 634, and, optionally, a second lumen 636 extending between the proximal and distal ends 632, 634, e.g., sized to slidably receive a guidewire, or other rail (not shown) therethrough. The inner member 630 is sized to be slidably received within the first lumen 626 of the outer member 620, e.g., such that an annular space is defined between the outer and inner members 620, 630 for passing one or more fluids therethrough, also similar to the previous embodiments. One or more sealing members, e.g., a nosecone 638, may be provided on the distal end 634 of the inner member 630, also similar to the previous embodiments.

As best seen in FIG. 18A, the balloon 650 includes a proximal end 652 coupled to the outer member distal end 624, a distal end 654 defining an outlet 658, and an interior 656 communicating with the first lumen 626 and the outlet 658. The distal end 634 of the inner member 630 may extend through the distal end 654 of the balloon 650, e.g., such that the outlet 658 defines an annular passage between the distal end 654 of the balloon 650 and the distal end 634 of the inner member 630. As best seen in FIG. 18B, the distal end 654 of the balloon 650 includes a spring stop, e.g., a collar or sleeve 655, attached or otherwise secured within the distal end 654, e.g., by bonding with adhesive, interference fit, sonic welding, fusing, and the like. The spring stop 655 may be spaced proximally from the outlet 658, e.g., such that the spring stop 655 does not interfere substantially with fluid flowing through the outlet 658 when the nosecone 638 is directed away from the outlet 658, as described further elsewhere herein.

Optionally, the distal end 654 of the balloon 650 may include a coating or other liner 657, e.g., adjacent the spring stop 655. For example, the liner 657 may include a lubricious and/or low surface energy material, e.g., PTFE, applied to the interior portion of the distal end 654 of the balloon 650 that may contact the nosecone 638, e.g., to reduce friction and/or adhesion between the balloon 650 and the nosecone 638, as described further below. Alternatively, the distal end 654 may be constructed similar to other embodiments herein, such as the embodiments shown in and described with respect to FIGS. 31A-32B.

The balloon 650 may be formed using similar materials and methods to any of the other embodiments described herein, for example, from substantially inelastic material, e.g., to provide a non-compliant balloon that expands to a predetermined size when inflated independent of pressure. The nosecone 638 may be carried on the inner member distal end 634 such that the nosecone 638 is movable relative to the balloon 650 as the inner member 630 is moved, e.g., to provide a valve for selectively opening and closing the outlet 658 of the balloon 650. The liner 657 may slidably contact the balloon 650, e.g., when the apparatus 610 is in the first position shown in FIG. 18A, such that a substantially fluid-tight seal is created without substantial friction or resistance to separation of the nosecone 638, e.g., when the outlet 658 is opened. For example, if the apparatus 610 is positioned in the first position after manufacturing and/or assembly, the liner 657 and nosecone 638 may remain in contact with one another for an indefinite time, e.g., during packaging, shipping, and/or storage, before use. The liner 657 may reduce the risk of adhesion between the balloon 638 and nosecone 638, e.g., which may otherwise occur if they are formed from similar materials and/or exposed to elevated temperatures.

As best seen in FIG. 18A, the apparatus 610 also includes a helical member or coil 670 coupled between the outer and inner members 620, 630 within the balloon interior 656. The helical member 670 may be movable from a relatively low profile, such as that shown in FIG. 18A, to an expanded helical shape, as shown in FIG. 18C and described further below. The helical member 670 may be a wire, tube, or other filament including a first end 672 coupled to the distal end 624 of the outer member 620 and a second end 674 coupled to the inner member 630. For example, similar to other embodiments herein, the helical member 670 may be formed from a core wire having a tube or sleeve formed or attached around the wire (not shown). Alternatively, the helical member 670 may be formed from a plurality of wires, e.g., braided or otherwise formed together into a single filament. Between the first and second ends 672, 674, the helical member 670 may wrap helically around the inner member 630 one or more times, also similar to other embodiments herein.

As shown, the first end 672 of the helical member 670 may be attached or otherwise secured directly to the distal end 624 of the outer member 620, e.g., by one or more of bonding with adhesive, sonic welding, soldering, interference fit (e.g., by wrapping the first end 672 one or more times around the distal end 624), inserting the first end 672 into an annular groove, hole, or pocket (not shown) in the distal end 624, fusing, providing a sleeve (not shown) around the distal end 624, and the like. Alternatively, the first end 672 of the helical member 670 may extend proximally through or along the outer member 622 or may be coupled to an actuator cable extending along the outer member 622, e.g., as shown in FIGS. 22A-22D and described further below.

Unlike the previous embodiments, the second end 674 of the helical member 670 may be coupled indirectly to the inner member 630, e.g., via spring element 690, best seen in FIG. 18B. The spring element 690 may include one or more springs or other biasing devices including an intermediate portion fixed to the inner member 630, e.g., by a first collar or attachment element 692, a proximal portion 694 coupled to the second end 674 of the helical member 670 by a second collar or attachment element 695, and a distal portion 696 extending distally from the first attachment element 692. Optionally, a membrane, sheath, or other structure (not shown) may be provided around at least a portion of the spring element 690, for example, over the proximal and/or distal portions 694, 696, which may protect the balloon 650 or other features of the apparatus 610, e.g., from being captured within windings of the spring element 690.

As best seen in FIG. 18B, the first collar 692 may be attached or otherwise fixed relative to the inner member 630, e.g., by bonding with adhesive, fusing, interference fit, one or more connectors (not shown), and the like. The distal end 697 of the spring element 690 and the second collar 695 may float freely around the inner member 630, e.g., to provide desired bias and/or compliance to the apparatus 610, as explained further below. Alternatively, the distal end 697 of the spring element 690 may be attached or otherwise fixed to the spring stop 655 or to the distal end 654 of the balloon 650, if desired.

The first collar 692 may be located generally at a midpoint on the spring element 690 or may be located closer to one end than the other. For example, as shown in FIG. 18B, the first collar 692 may be attached to the spring element 690 closer to the second collar 695 than to the distal end 697. Thus, in this embodiment, the distal portion 696 of the spring element 690 includes more windings than the proximal portion 694, although it will be appreciated that fewer or more windings may be provided in either the proximal or distal portions 694, 696, e.g., to provide predetermined spring properties, as desired.

In one embodiment, the spring element 690 may be a single spring having a substantially uniform spring constant and/or other mechanical properties along its length, or the properties may be varied, e.g., between the proximal portion 694 and the distal portion 696. In an alternative embodiment, the proximal and distal portions 694, 696 may be separate springs independently attached to the first collar 692, each having desired properties for their respective purposes, e.g., biasing and/or providing compliance to the apparatus 610, as described further below. The spring element 690 may be formed from one or more materials, e.g., metal, such as stainless steel, thermoplastic, thermoset plastics, glass, or composite materials.

As best seen in FIG. 18B, the distal portion 696 of the spring element 690 may terminate in a distal end 697 for contacting the spring stop 655, e.g., to bias the inner member 630 axially relative to the balloon distal end 654. Optionally, the distal end 697 may include a planar ring defining a plane substantially perpendicular to the longitudinal axis 627, e.g., to provide enhanced apposition against the spring stop 655, if desired. The distal portion 696 of the spring element 690 may have a diameter smaller than the distal end 654 of the balloon 650 and larger than the inner diameter of the spring stop 655, e.g., such that the distal portion 696 may move freely within the distal end 654 of the balloon 650 limited by contact between the distal end 697 and the spring stop 655, as described further below.

The first collar 692 may be offset proximally from the nosecone 638 by a predetermined distance and/or the distal portion 696 of the spring element 690 may have a predetermined length to provide a desired bias. For example, these distances and/or the spring constant of the distal portion 696 may be such that the spring element 690 biases the nosecone 638 against the distal end 654 of the balloon 650, e.g., to substantially seal the outlet 658, yet allow the inner member 630 to be directed distally to move the nosecone 638 away from the balloon 650 to open the outlet 658, as described further below.

As shown in FIGS. 18A and 18B, the second end 674 of the helical member 670 and the proximal end 694 of the spring element 690 are attached to the second collar 695, e.g., by bonding with adhesive, fusing, interference fit, one or more connectors (not shown), and the like. The second collar 695 may be free to move axially relative to the inner member 630, e.g., without substantial lateral movement, to provide compliance to the helical member 670, as described further below.

Optionally, the apparatus 610 may include one or more markers (not shown) to facilitate positioning and/or advancement of the apparatus 610 during use, e.g., on the distal end 634 of the inner member 630, balloon 650, and/or helical member 670, similar to other embodiments herein.

Turning to FIGS. 19A-19C, the handle 660 may be coupled to or otherwise provided on the proximal end 622 of the outer member 620, e.g., for manipulating the outer member 620 and/or the entire apparatus 610, similar to the previous embodiments. The handle 660 generally includes a housing 661 attached to the outer member 620, and may include one or more ports 664 for accessing the lumens of the apparatus 610 and/or one or more actuators 662 for operating features of the apparatus 610.

For example, the handle 660 may include a first side port 664a that communicates with the annular first lumen 626 in the outer member 620, and may include a connector, e.g., a Luer lock fitting, for coupling one or more fluid or vacuum sources to the apparatus 610, e.g., a syringe or other source (not shown) for delivering fluid through the first lumen 626 into the interior 656 of the balloon 650 and/or through the outlet 658 (depending upon the position of the inner member 630). In addition, the handle 660 may include a second port 664b that communicates with the second lumen 636 of the inner member 630. The second port 664b may include one or more seals, e.g., a hemostatic seal (not shown), that may accommodate receiving a guidewire or other instrument (not shown) through the second port 664b into the second lumen 636 while maintaining a substantially fluid-tight seal to prevent substantial fluid flow proximally from the second lumen 636.

In addition, the handle 660 may include a slider, thumb control, push button, or other actuator 662 coupled to the inner member 630 for moving the inner member 630, e.g., to open and/or close the outlet 658 (see FIGS. 18A, 18B) and/or expand and collapse the helical member 670, as described further below and/or similar to other embodiments herein. Optionally, the handle 660 may include one or more seals, bushings, and the like (not shown), between the outer and inner members 620, 630, which may guide the inner member 630 as it moves axially relative to the outer member 630 and handle 660, e.g., also similar to other embodiments herein.

Figure 20A:
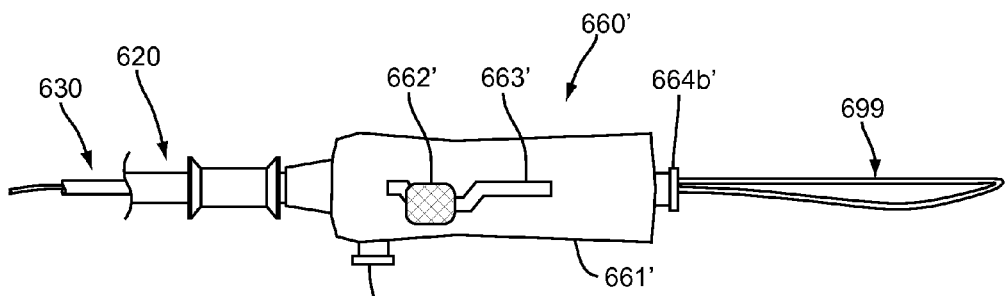
FIGS. 20A-20C are side views of an alternative embodiment of a proximal end that may be provided on the apparatus of FIGS. 18A-18C.
Figure 20B:
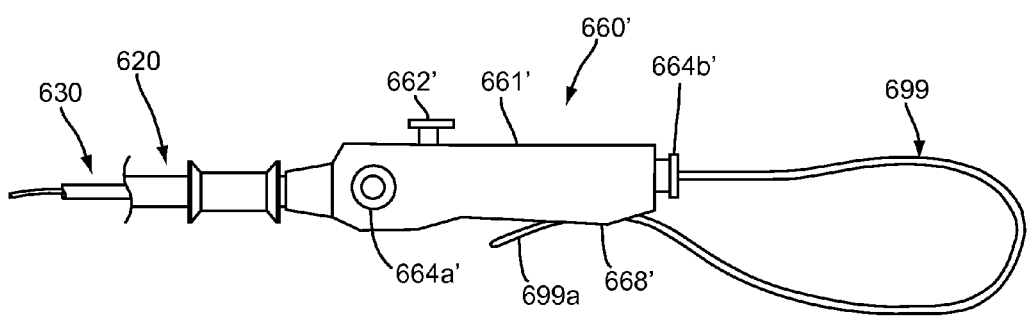
Figure 20C:
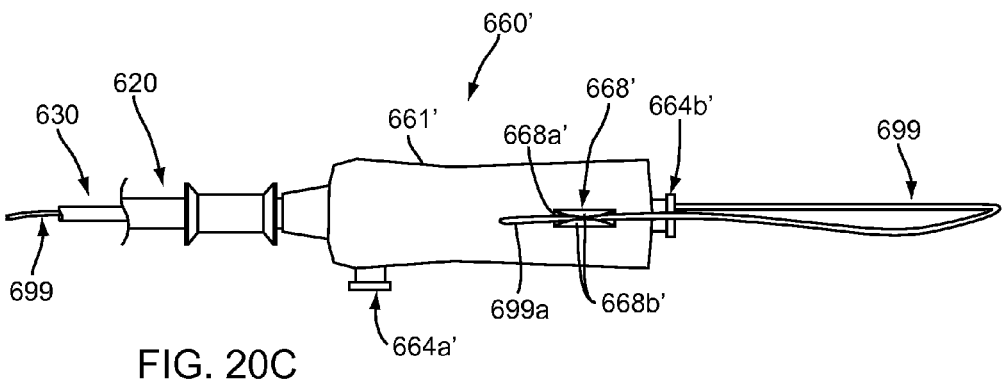

FIGS. 20A-20C show an alternative embodiment of a handle 660' that may be generally similar to the handle 660 shown in FIGS. 19A-19C, e.g., including a housing 661' that includes side ports 664' and a slot 663' within which a push button, thumb control, or other actuator 662' moves. Unlike the handle 660, the housing 661' may include a clip or other receptacle 668' for engaging a guidewire or other instrument 699 received in the side port 664b'. For example, as best seen in FIG. 20C, a recess 688a' may be provided on the bottom of the housing 661' within which a pair of opposing flexible members, rubber molding or other structures 668b', and the like are attached. A guidewire 699 is shown pressed into the recess 668a' between and/or under the structures 668b' to removably capture the guidewire 699 in the recess 668a'. Alternatively, the clip 668' may include other opposing elements, e.g., ridges, cleats, and the like (not shown), mounted or otherwise attached to the housing 661'. Although the clip 668' is shown on the bottom of the housing 661', it will be appreciated that the clip 668' may be provided on other surfaces or locations of the housing 661', e.g., at a location that minimizes interference with holding and/or operating the handle 660'.

During use, a guidewire 699 or other instrument may be introduced through the second port 664b', e.g., by insertion into the second port 664b' or by backloading into the distal end 634 of the inner member 630 (not shown), such that a proximal end 699a of the guidewire 699 extends proximally from the second port 664b'. The exposed portion of the guidewire 699 may be looped back and the proximal end 699a captured in the clip 668', e.g., by pressing the proximal end 699a through the structures 668b' into the recess 668a'. Friction of the structures 668b' may releasably retain the proximal end 699a in the recess 668a' If desired to move or otherwise manipulate the proximal end 699a, the guidewire 699 may be pulled away from the housing 661' to open the structures 668b' and remove the proximal end 699a from the clip 668'. Thus, the clip 668' may be useful for managing long guidewires or other instruments, which may otherwise fall off a procedure table or risk leaving a sterile field in which a procedure is being performed.

Figure 28A:
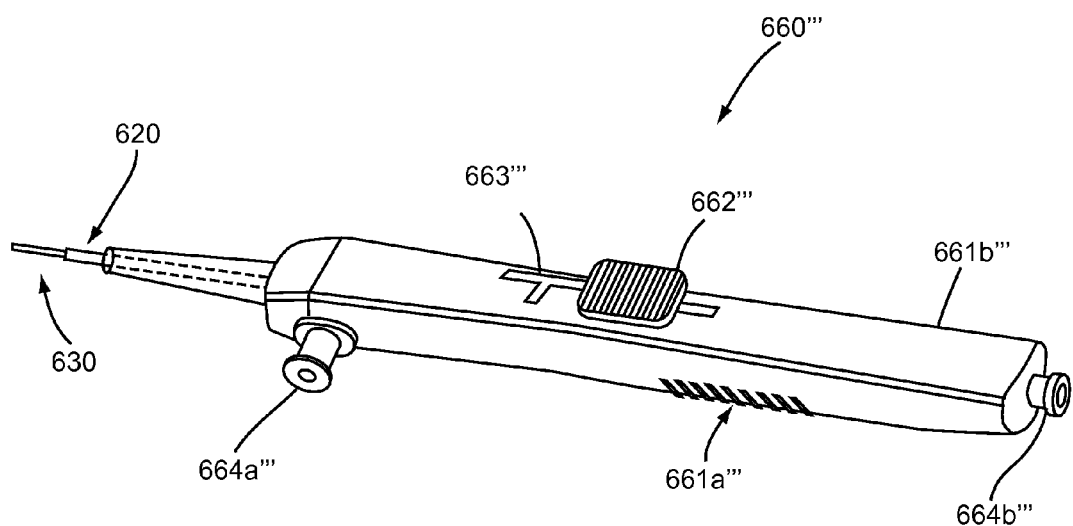
FIG. 28A is a perspective view of an exemplary embodiment of a handle that may be provided on a balloon apparatus, such as the apparatus of FIGS. 21A-22D.
Figure 28B:
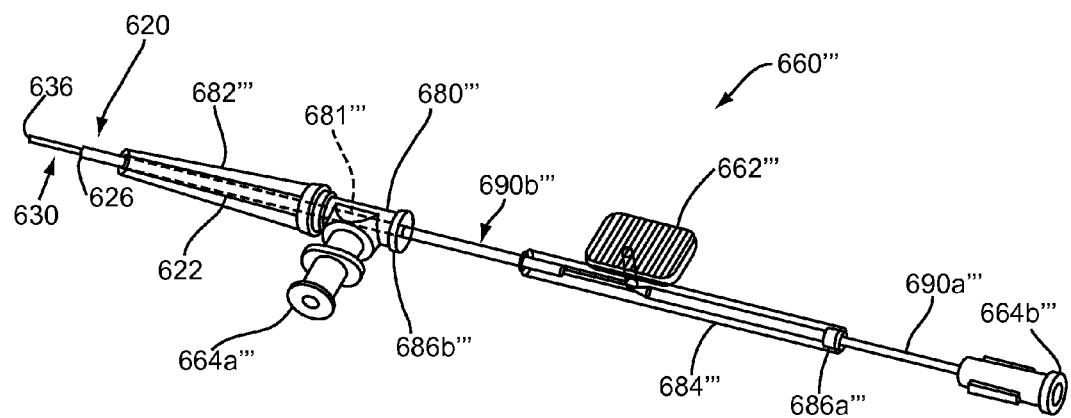
FIG. 28B is a perspective view of components of the handle of FIG. 28A with an outer housing of the handle removed.

FIGS. 28A and 28B show another exemplary embodiment of a handle 660''' generally similar to those described above, e.g., including a housing 661''' that includes side ports 664''' and a push button, thumb control, or other actuator 662''' that moves within or otherwise relative to a slot or track 663.''' As shown in FIG. 28A, the housing 661''' may include mating clam shell halves that may be attached together, e.g., by bonding with adhesive, sonic welding, fusing, mating connectors, and the like along a seam therebetween, to define the slot 663''' and gripping surfaces for the handle 660.'''

FIG. 28B shows an exemplary configuration of internal components of the handle 660''' after the housing 661''' shown in FIG. 28A has been removed for clarity. As shown, the handle 660''' includes stationary components that are coupled to the outer member 620 and/or housing 661,''' e.g., a manifold 680,''' a stress relief transition 682,''' and a proximal hypotube or other tubular body 690a,''' and movable components that are coupled to the inner member 630 and movable axially within the housing 661,''' e.g., a carriage 684''' and a distal hypotube or other tubular body 690b.'''

For example, the manifold 680''' and transition 682''' may be attached to or otherwise substantially fixed relative to the housing 661''' and the proximal end 622 of the outer member 620 may be received in and/or attached to the transition 682''' and/or manifold 680''' such that these components remain substantially stationary relative to the handle 660.''' The manifold 680''' includes an inner chamber or passage 681''' that communicates with the first lumen 626 of the outer member 620. A Luer fitting or other connector may be attached to the manifold 680''' to provide a first side port 664a''' that communicates with the chamber 681''' and, consequently, with the first lumen 626.

The proximal tubular body 690a''' may also be substantially fixed or otherwise mounted to the housing 661''' with a proximal end extending from the housing 661''' and including a Luer fitting to provide a second side port 664b,''' e.g., for receiving a guidewire or other instrument (not shown), similar to other embodiments herein. The distal end of the proximal tubular body 690a''' may be received within the carriage 684''' such that the carriage 684''' may be slid axially at least partially over the proximal tubular body 690a.''' As shown, the carriage 684''' may include an o-ring or other seal 686a,''' e.g., received within a retainer or seat, to provide a substantially fluid-tight seal between the proximal tubular body 690a''' and carriage 684''' while the carriage 684''' moves.

The carriage 684''' may be supported within the housing 661''' such that the carriage 684''' is free to move axially therein between proximal and distal positions with minimal lateral movement. The actuator 662''' may be attached or otherwise coupled to the carriage 684''' such that the actuator 662''' extends through the slot 663''' in the housing 661,''' similar to the previous embodiments. The distal tubular body 690b''' may include a proximal end received in and/or otherwise fixed relative to the carriage 684''' and a distal end that extends through the manifold 680''' and/or transition 682''' to accommodate attaching the distal tubular body 690b''' to the inner member 630. The manifold 680''' may also include an o-ring or other seal 686b,''' e.g., received within a retainer or seat, to provide a substantially fluid-tight seal between the distal tubular body 690b''' and the manifold 680''' while accommodating axial movement of the distal tubular body 690b.''' Thus, fluid introduced into the chamber 681''' of the manifold 680''' via the first side port 664a''' may pass into the lumen 626 of the outer member 620 without substantial leakage.

Similar to previous embodiments, the actuator 662''' may be directed axially between two or more positions, thereby causing the carriage 684''' to slide axially within the housing 661''' and, consequently, direct the distal tubular body 690b''' and inner member 630 to move axially relative to the outer member 620 and handle 660.'''

Returning to FIGS. 19A-19C, the housing 661 may include an elongate slot 663 and the actuator 662 may be slidable generally axially within the slot 663 to direct the apparatus 610 between one or more modes of operation. For example, the slot 663 may include three distinct axial regions 663a, 663b, 663c connected by diagonal regions 663d, 663e, which may correspond to three different modes of operation for the apparatus 610. With the actuator 662 in the second region 663b, as shown in FIG. 19A, the inner member 630 may be positioned axially such that the nosecone 638 contacts the distal end 654 of the balloon 650 to substantially seal the outlet 658, as shown in FIG. 18A.

If balloon inflation is desired during injection, the distal balloon section 654 may be sized to offer resistance to flow. This resistance to flow may cause at least partial inflation of the balloon 650 while also delivering fluid from the outlet 658. Alternatively, the balloon section 654 may be made large enough not to offer significant resistance to flow, in which case fluid may be delivered from the outlet 658 while the balloon 650 remains substantially collapsed.

When the actuator 662 is directed distally into the first region 663a, as shown in FIG. 19B, the inner member 630 is advanced distally to direct the nosecone 638 away from the distal end 654 of the balloon 650 and open the outlet 658, e.g., as shown in FIG. 18B. When the actuator 662 is directed proximally into the third region 663c, the inner member 630 may be retracted proximally to expand the helical member 670. If desired, the third region 663c may have sufficient length to allow the actuator 662 to be directed along the length of the third region 663c, e.g., to vary the size of the helical member 670 in the expanded helical shape. For example, the actuator 662 may be placed in any intermediate position along the third region 663c with the helical member 670 growing to a progressively larger diameter as the actuator 662 is directed proximally within the third region 663c. Thus, by modulating the position of the actuator 662 within the third region 663, a user may control the diameter of the helical member 670 to approximate the size of the anatomy encountered.

Optionally, the slot 663 may include one or more pockets or detents (not shown) that may capture a feature on the actuator 662, e.g., to releasably secure the actuator 662 in one or more of the positions, e.g., similar to other embodiments herein. In addition or alternatively, the housing 661 may include one or more visual indicators (not shown), e.g., for identifying the position of the inner member 630 and/or mode of the apparatus 610 when the actuator 662 is received in a particular region or pocket, also similar to other embodiments herein.

The apparatus 610 may be biased to one of the three modes, e.g., such that the actuator 662 is biased to move into one of the regions 663a-663c yet may be selectively directed into one of the other regions 663a-663c to direct the apparatus 610 to one of the other modes. For example, as described above, spring element 690 may include distal portion 696, which may bias the inner member 630 proximally to engage the nosecone 638 with the distal end 654 of the balloon 650 to substantially seal and/or enhance sealing the outlet 658, as shown in FIG. 18B. The length of the distal portion 696 and relative locations of the first collar 692 and spring stop 655 may be set such that the distal portion 696 is under slight compression when the nosecone 638 is engaged with the distal end 654 of the balloon 650, which may ensure that the outlet 658 is maintained substantially sealed. Consequently, the actuator 662 may be biased towards the second region 663b, as shown in FIG. 19B.

In addition, the proximal portion 694 of the spring element 690 may provide compliance to the helical member 670, e.g., as it is directed between the first and second modes. For example, with the actuator 662 in the second region 663b, the proximal portion 694 of the spring element 690 may maintain sufficient tension on the helical member 670 to constrain the helical member 670 closely around the inner member 630. If the distal end 674 of the helical member 670 were attached directly to the inner member 630, sufficient slack would need to be provided to accommodate advancement of the inner member 630 to open the outlet 658, which may increase the profile of the helical member 670 and, consequently, the overall apparatus 610.

When the actuator 662 is advanced to the first region 663a, the first collar 692 moves distally, and the proximal portion 694 of the spring element 690 may absorb most or substantially all of the resulting displacement. For example, the proximal portion 694 may have sufficient elasticity to extend axially rather than the helical member 670 being subjected to substantial axial tension, which could apply a proximal force that may interfere with opening the outlet 658 (i.e., the helical member 670 may otherwise operate as a spring against the desired distal movement of the inner member 630). The proximal portion 692 of the spring element 690 may also reduce distal tension that may otherwise pull the distal end 674 of the helical member 670 distally, potentially stretching or plastically deforming the helical member 670 when the outlet 658 is opened.

Figure 21A:
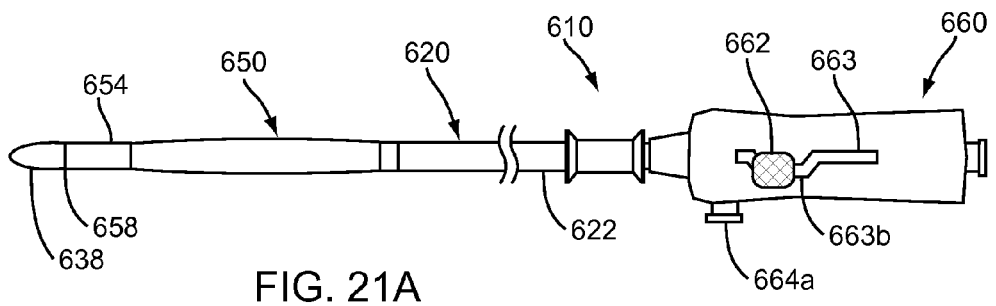
FIGS. 21A-21D are side views of the apparatus of FIGS. 18A-19C, showing the apparatus being directed between different modes of operation.

With additional reference to FIGS. 21A-21D, during use, the apparatus 610 may be provided to a user as shown in FIG. 21A, i.e., with the balloon 650 and helical member 670 collapsed, and the valve provided by the nosecone 638 sealed, i.e., with the actuator 662 in the second region 663b of the slot 663. For example, as explained above, the nosecone 638 may be biased to seal the outlet 658 in the distal end 654 of the balloon 650, thereby biasing the actuator 662 towards the second region 663b.

The distal end of the apparatus 610 may be introduced into a patient's body, e.g., into a body lumen (not shown), similar to the previous embodiments, with the outlet 658 substantially sealed. At a desired location, the actuator 662 may be advanced into the first region 663a, as shown in FIG. 19B, thereby directing the apparatus 610 to the infusion mode, i.e., moving the nosecone 638 away from the distal end 654 of the balloon 650 to open the outlet 658 and compressing the distal portion 696 of the spring element 690, e.g., as shown in FIG. 18B (although without expanding the balloon 650). Thus, fluid introduced into the first port 664a and through the first lumen 626 of the outer member 620 may pass through the balloon interior 656 and out the outlet 658, e.g., into the body lumen beyond the nosecone 638, without substantially expanding the balloon 650, similar to the previous embodiments. Alternatively, as described above, the outlet 658 may provided sufficient resistance to fluid flow therethrough that the balloon 650 is at least partially expanded as fluid is delivered through the outlet 658. In the infusion mode, contrast, diagnostic or therapeutic fluids, and the like may be introduced into the body lumen, while the apparatus 610 is manipulated or maintained substantially stationary, similar to the previous embodiments.

Figure 21B:
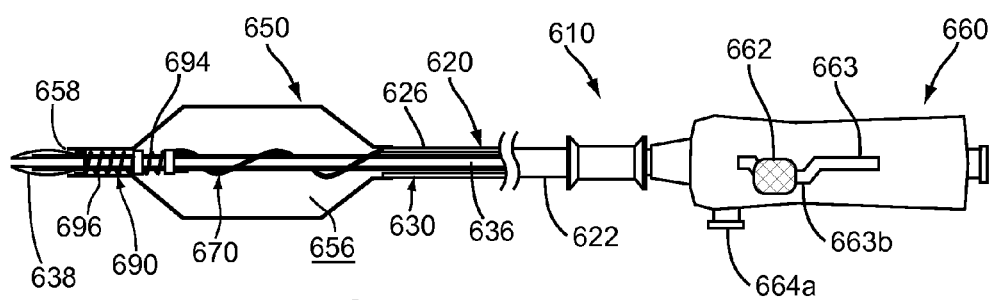

After sufficient fluid has been delivered and/or it is otherwise desired to seal the outlet 658, the actuator 662 may be retracted into the second region 663b, thereby directing the inner member 630 proximally until the nosecone 638 engages the distal end 654 of the balloon 650, substantially sealing the outlet 658, as shown in FIGS. 18A and 21B. The spring element 690 may have a spring constant that provides sufficient bias to ensure that the outlet 658 is substantially sealed by the nosecone 638. Alternatively, the spring element 690 may provide sufficient bias such that, when the actuator 662 is released, the energy stored in the distal portion 696 of the spring element 690 may automatically direct the inner member 630 proximally until the nosecone 638 engages the distal end 654 of the balloon 650, substantially sealing the outlet 658. Consequently, the actuator 662 may be directed automatically back into the second region 663b of the slot 663, and the spring element 690 may provide a positive valve closure of the outlet 658. This may be useful because the force to close the outlet 658 is provided by the spring element 690 at the distal end of the apparatus 610 and does not rely on forces being transmitted over the length of the apparatus 610, which may otherwise be subject to axial compliance within the inner and outer members 630, 620 and therefore less reliable.

As shown in FIG. 21B, in the second mode, any fluid introduced through the first lumen 626 enters the balloon interior 656 and expands the balloon 650, similar to the previous embodiments. For example, in this mode, the balloon 650 may be expanded to an elongate substantially cylindrical shape, e.g., having a substantially uniform diameter main portion between tapered end portions. The balloon 650 may be used to dilate or otherwise apply substantial pressure to a wall of a body lumen, e.g., for dilating a stenosis, obstruction, or other lesion, similar to the method shown in FIGS. 9E-9G and described elsewhere herein. Alternatively, the balloon 650 may be formed from elastic and/or substantially compliant material such that the balloon 650 may be expanded within a body lumen and directed axially to remove material within the body lumen, similar to other embodiments herein.

Figure 21C:
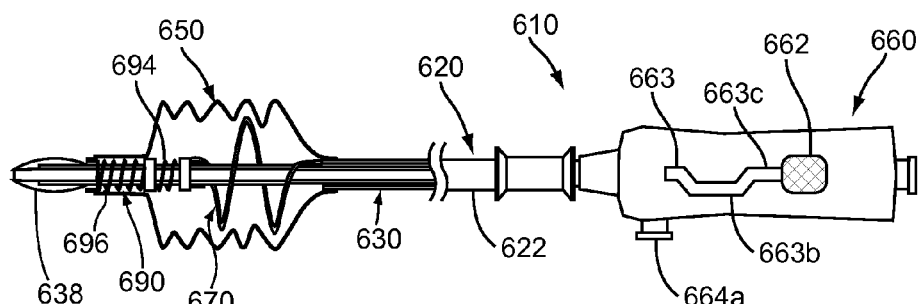
Figure 21D:
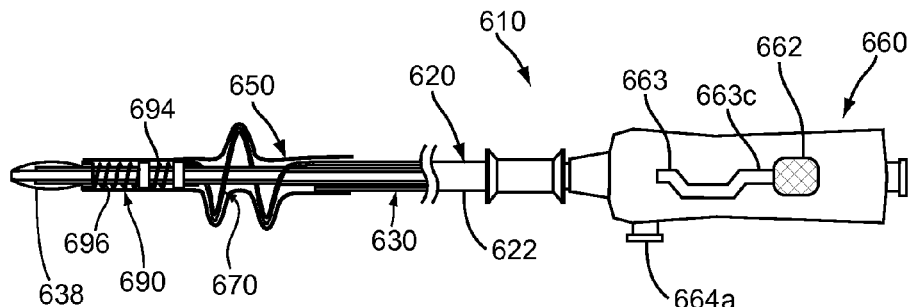

In addition, as shown in FIG. 19C, the actuator 662 may be retracted into the third region 663c to direct the apparatus 610 to the third mode shown in FIGS. 18C and 21D, e.g., for removing thrombus or other undesired material within a body lumen, similar to the other embodiments herein. For example, with the balloon 650 collapsed, the actuator 662 may be retracted to direct the inner member 630 proximally, thereby axially compressing the helical member 670 and directing the distal end 674 of the helical member 670 proximally towards the proximal end 672. Similar to other embodiments herein, this causes the helical member 670 to expand radially outwardly as it is compressed axially, thereby causing the balloon 650 also to compress axially and expand radially into an expanded helical shape around the helical member 670, as shown in FIGS. 18C and 21D.

The length of the third region 663c of the slot 663 may limit proximal movement of the inner member 630 in a predetermined manner when compressing and expanding the balloon 650 and helical member 670, e.g., to prevent over-compression of the balloon 650 and/or helical member 670. For example, as described above, the actuator 662 may be placed in any intermediate position along the length of the third region 663c to vary the diameter of the helical member 670 in the expanded helical shape. By modulating the position of the actuator 662 along the third region 663c, the user may control the diameter of the helical member 670 to correspond to the patient's vasculature, e.g., to provide sufficient friction and/or engagement with the wall of a body lumen being treated to remove sufficient material from the wall.

If the balloon 650 has been previously inflated, a source of vacuum, e.g., a syringe or vacuum line (not shown), may be coupled to the side port 664a to evacuate fluid from the interior 656 to collapse the balloon 650 to the contracted condition around the helical member 670 before directing the actuator 662 into the third region 663c. Alternatively, if the balloon 650 has not been previously inflated, e.g., if thrombus is to be removed before dilating a body lumen, it may not be necessary to collapse the balloon 650 further using vacuum since the balloon 650 may already be sufficiently collapsed or otherwise remain in the contracted condition.

Alternatively, as shown in FIGS. 21C and 21D, the actuator 662 may be directed from the second region 663b to the third region 663c while the balloon 650 remains inflated. For example, as shown in FIG. 21B, the balloon 650 may be inflated (if not already inflated) while the helical member 670 remains wound closely around the inner member 630. Turning to FIG. 21C, the inner member 630 may be directed proximally relative to the outer member 620, e.g., by directing the actuator 662 proximally into the third region 663c, as described above. This may cause the balloon 650 to buckle but remain generally cylindrical as it is compressed axially, e.g., due to being partially constrained within a body lumen and/or fluid remaining within the interior 656 of the balloon 650.

Optionally, the apparatus 610 may include one or more relief valves or other features (not shown), e.g., on the handle 660 or other location on the proximal end 622 of the outer member 620, that communicate with the first lumen 626 to prevent overexpansion of the balloon 650 as it is axially compressed. For example, a relief valve may bleed excess fluid from the interior 656 of the balloon 650 as the inner member 630 is directed proximally, thereby automatically reducing the volume of fluid within the interior 656 of the balloon 650 and/or the first lumen 626. Alternatively, a manual valve or other feature (not shown) may be provided on the handle 660 that may be opened by the user before or as the inner member 630 is directed proximally or that is activated when the actuator 662 is directed along the slot 663 to a predetermined position within or adjacent the third region 663c.

As shown in FIG. 21C, the helical member 670 may expand radially outwardly within the expanded balloon 650 as the inner member 630 is directed proximally to adopt the expanded helical shape. Movement of the helical member 670 may be relatively unimpeded by the balloon 650, which may allow the helical member 670 to expand more uniformly than if the helical member 670 were expanded within a collapsed balloon 650. In addition, because the balloon 650 is already inflated, expansion of the helical member 670 in this manner may reduce the risk of creating tight folds or other stress on the balloon 650 as the helical member 670 expands, which may otherwise damage the balloon 650.

Turning to FIG. 21D, once the helical member 670 is sufficiently expanded, the balloon 650 may be deflated, allowing the balloon 650 to collapse around and substantially adopt the shape of the expanded helical member 670. Thus, the balloon 650 may provide a substantially impervious layer around the helical member 670, which may prevent material being removed from being captured within or around the helical member 670. The collapsed balloon 650 draped around the expanded helical member 670 may also provide mechanical reinforcement to the helical member 670, e.g., to provide a more robust helical structure for removing thrombus or other material within the body lumen.

After sufficient thrombus or other material is removed, the balloon 650 may be partially or fully inflated again, and the actuator 662 and inner member 630 may be advanced distally to direct the helical member 670 back towards the low profile around the inner member 630. Once the actuator 662 and inner member 630 are advanced to the second position, the balloon 650 may be deflated, e.g., by coupling a source of vacuum to the first port 664a, and/or the actuator 662 and inner member 630 may be advanced to the distal position to open the valve. Alternatively, the inner member 630 may be advanced distally with the balloon 650 remaining collapsed to direct the helical member 670 towards the low profile, similar to the previous embodiments. Once collapsed, the apparatus 610 may be directed to another location within the patient's body, e.g., for additional fluid infusion, dilation, and/or thrombus removal, or removed entirely from the patient's body.

Turning to FIGS. 22A-22D, another exemplary embodiment of an apparatus 610" is shown for treating a body lumen that includes an outer member 620," an inner member 630," a balloon 650," a nosecone 638," a spring element 690," and a handle 660," which are generally constructed and operated similar to the apparatus 610. Although the apparatus 610" includes a helical member 670' with a distal end 674" coupled to the inner member 630," e.g., via the spring element 690," unlike the apparatus 610, a proximal end 672" of the helical member 670" is not coupled to the outer member 620." Instead, the proximal end 672" of the helical member 670" may be coupled to an actuator cable, wire, or other elongate member 673" that extends proximally through the outer member 620" and is coupled to a first actuator 662a" on the handle 660."

Thus, axial movement of the inner member 630" relative to the outer member 620" may be substantially independent of expansion and/or collapse of the helical member 670." For example, a second actuator 662b" on the handle 660" may be directed to move the inner member 620" and nosecone 638" to open and/or close the outlet 658," similar to the embodiments described above. However, the distal end 674" of the helical member 670" may be substantially decoupled from such movement, e.g., by the spring element 690," similar to the previous embodiment. Instead, the first actuator 662a" may be directed axially, as shown in FIGS. 22B and 22C, to direct the actuator member 673" axially. This action may direct the proximal end 672" of the helical member 670" distally towards the distal end 674" to expand the helical member 670," or proximally away from the distal end 674" to collapse the helical member 670."

Figure 22A:
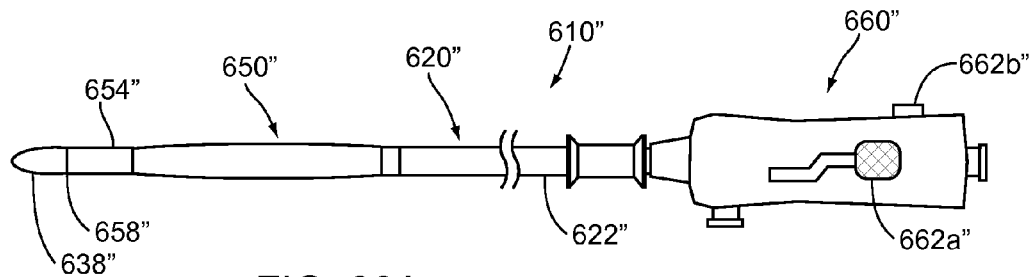
FIGS. 22A-22D are side views of an alternative embodiment of the apparatus similar to the apparatus of FIGS. 18A-21D, but including a balloon and an expandable coil for treating a body lumen that is de-coupled from the balloon.
Figure 22B:
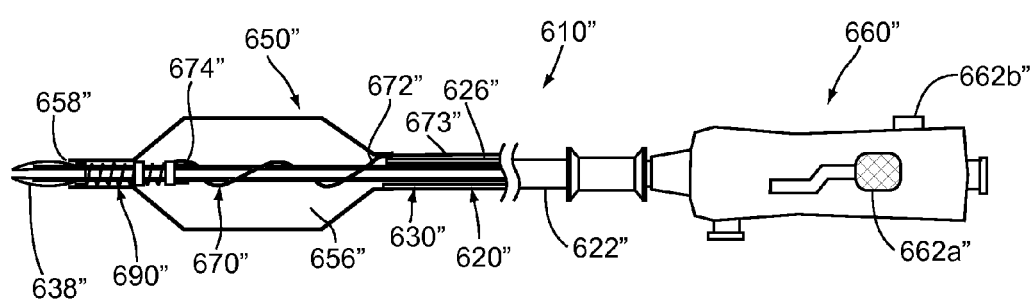
Figure 22C:
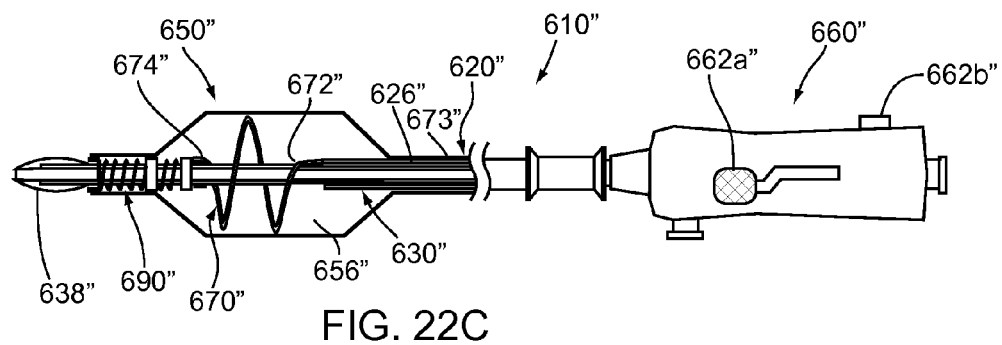

During use, the apparatus 610" may be provided to a user as shown in FIG. 22A, i.e., with the balloon 650" and helical member 670" collapsed, and the nosecone 638" substantially sealing the outlet 658." For example, as explained above, the inner member 630" and, consequently, the nosecone 638" may be biased by the spring element 690" to substantially seal the outlet 658" in the distal end 654" of the balloon 650, and the second actuator 662b" in a proximal position. If it is desired to infuse fluid through the first lumen 626" of the outer member 620," the second actuator 662b" may be directed to a distal position, thereby advancing the inner member 630" and nosecone 638" away from the distal end 654" of the balloon 650" to open the outlet 658," e.g., as described above. When the second actuator 662b" is retracted, the nosecone 638" may substantially seal the outlet 658" with the spring element 690" providing sufficient bias to enhance the seal. Alternatively, the spring element 690" may provide sufficient bias such that, when the second actuator 662b" is released, the nosecone 638" may automatically seal the outlet 658" and the second actuator 662b" may automatically retract to its proximal position, similar to other embodiments herein.

As shown in FIG. 21B, with the second actuator 662b" in the proximal position, any fluid subsequently introduced through the first lumen 626" enters the balloon interior 656" and expands the balloon 650," similar to the previous embodiments. For example, in this mode, the balloon 650" may be used to dilate or otherwise apply substantial pressure to a wall of a body lumen, e.g., for dilating a stenosis, lesion, or other obstruction, similar to the methods described elsewhere herein.

Figure 22D:
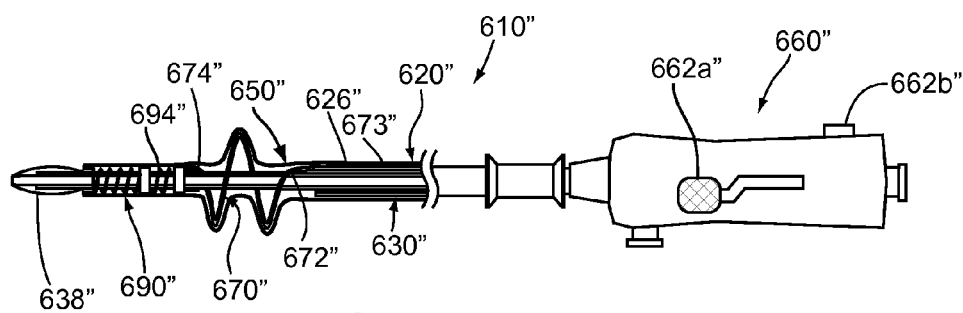

If desired, with the balloon 650" expanded, the actuator 662a" may be advanced to its distal position to expand the helical member 670" radially outwardly within the balloon 650", as shown in FIG. 22C. As the helical member 670" is expanded, the balloon 650" may remain fully expanded without substantially shortening, which may reduce the formation of folds in the balloon 650" as may occur in the previous embodiments. Thus, the helical member 670" may expand freely to a desired helical shape without substantial interference from the balloon 650." As shown in FIG. 22D, once the helical member 670" is sufficiently expanded, the balloon 650" may be deflated, e.g., by opening the valve and/or aspirating fluid from the balloon 650," allowing the balloon 650" to collapse around and substantially adopt the shape of the expanded helical member 670," as described above.

After sufficient thrombus or other material is removed, the balloon 650" may be partially or fully inflated again, and the actuator 662a" may be retracted proximally to direct the helical member 670" back towards the low profile around the inner member 630." Once the actuator 662a" is directed to its proximal position, the balloon 650" may be deflated and the apparatus 610" may be directed to another location or removed from the patient's body.

Figure 29:
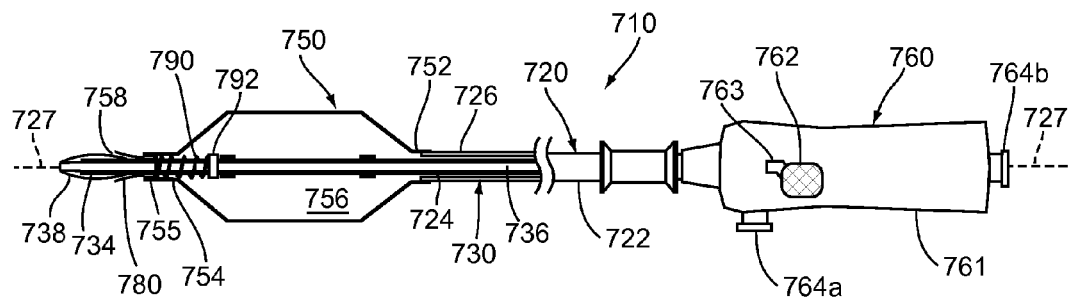
FIG. 29 is a partially cross-sectional side view of still another exemplary embodiment of an apparatus for treating a body lumen.
Figure 30A:
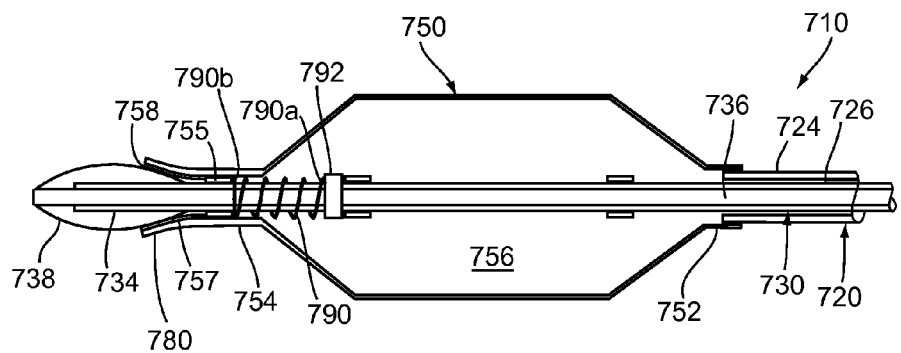
FIGS. 30A and 30B are details of the distal end of the apparatus of FIG. 29, showing a valve closed and open, respectively.
Figure 30B:
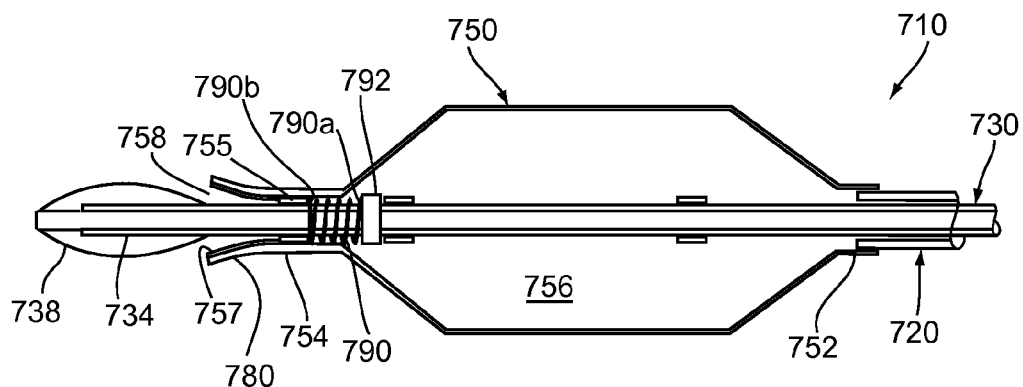

Turning to FIGS. 29, 30A, and 30B, still another embodiment of an apparatus 710 is shown for treating a body lumen that is generally similar to the previously embodiments, e.g., generally similar to apparatus 610 shown in FIGS. 18A-19C without the helical member 670.

For example, the apparatus 710 includes an outer tubular member 720, an inner member 730, and an expandable balloon 750 carried by the inner and/or outer members 720, 730, generally similar to the previous embodiments. In addition, the apparatus 710 includes a handle or hub 760 coupled to or otherwise provided on a proximal end 722 of the outer member 720, e.g., for manipulating the outer member 720 and/or the entire apparatus 710, also generally similar to the previous embodiments. Also similar to previous embodiments, the apparatus 710 may include an actuator 762 on the handle 760 for operating the apparatus 710 in multiple modes, e.g., a first mode for dilating an obstruction within a body lumen (shown in FIG. 30A), and a second mode for infusing fluid into a body lumen (shown in FIG. 30B, although with the balloon 750 collapsed).

As shown, the outer member 720 includes a proximal end 722, a distal end 724 sized for introduction into a body lumen, and a first lumen 726 extending along a central longitudinal axis 727 therebetween, which may be constructed similar to the previous embodiments. The inner member 730 also includes a proximal end (not shown), a distal end 734, and, optionally, a second lumen 736, e.g., sized to slidably receive a guidewire or other instrument (not shown) therethrough. The inner member 730 is sized to be slidably received within the first lumen 726 of the outer member 720, e.g., such that an annular space is defined between the outer and inner members 720, 730 for passing one or more fluids therethrough, also similar to the previous embodiments. One or more sealing members, e.g., a nosecone 738, may be provided on the distal end 734 of the inner member 730 to provide a valve, also similar to the previous embodiments.

As best seen in FIG. 30A, the balloon 750 includes a proximal end 752 coupled to the outer member distal end 724, a distal end 754 defining an outlet 758, and an interior 756 communicating with the first lumen 726 and the outlet 758. The distal end 734 of the inner member 730 may extend through the distal end 754 of the balloon 750, e.g., such that the outlet 758 defines an annular passage between the distal end 754 of the balloon 750 and the distal end 734 of the inner member 730 when open. The distal end 754 of the balloon 750 includes a spring stop, e.g., a collar or sleeve 755, attached or otherwise secured within the distal end 754, e.g., by bonding with adhesive, interference fit, sonic welding, fusing, and the like. The spring stop 755 may be spaced proximally from the outlet 758, e.g., such that the spring stop 755 does not interfere substantially with fluid flowing through the outlet 758 when the nosecone 738 is directed away from the outlet 758, similar to the previous embodiments.

A spring element 790 may be coupled to the inner member 730, e.g., by a collar or other attachment element 792, such that the spring element 790 may be compressed between the collar 792 and the spring stop 755, e.g., to bias the nosecone 738 to substantially seal the outlet 758, similar to the previous embodiments. For example, a proximal or first end 790a of the spring element 790 may be attached or otherwise coupled to the collar 792 and a distal or second end 790b of the spring element 790 may be coupled to or merely in contact with the spring stop 755.

The collar 792 may be attached or otherwise fixed relative to the inner member 730, e.g., by bonding with adhesive, fusing, interference fit, one or more connectors (not shown), and the like. The distal end 790b of the spring element 790 may float freely around the inner member 730, e.g., to provide desired bias to the apparatus 710, similar to the previous embodiments. Optionally, the distal end 790b may include a planar ring defining a plane substantially perpendicular to the longitudinal axis 727, e.g., to provide enhanced apposition against the spring stop 755, if desired. The spring element 790 may have a diameter smaller than the distal end 754 of the balloon 750 and larger than the inner diameter of the spring stop 755, e.g., such that the spring element 790 may move freely within the distal end 754 of the balloon 750 limited by contact between the distal end 790b and the spring stop 755. Alternatively, the distal end 790b of the spring element 790 may be attached or otherwise fixed to the spring stop 755 or to the distal end 754 of the balloon 750, if desired.

The collar 792 may be located on the inner member 730 such that the collar 792 does not interfere substantially with fluid flow through the distal end 754 and the outlet 758 when the outlet 758 is open, e.g., as shown in FIG. 30B. For example, the collar 792 may be offset proximally from the nosecone 738 by a predetermined distance and/or the spring element 790 may have a predetermined length to provide the desired bias without interfering with fluid flow. Similar to the previous embodiments, these lengths and/or the spring constant of the spring element 790 biases the nosecone 738 against the distal end 754 of the balloon 750, e.g., to substantially seal the outlet 758, yet allow the inner member 730 to be directed distally to move the nosecone 738 away from the balloon 750 to open the outlet 758.

Optionally, a membrane, sheath, or other structure (not shown) may be provided around at least a portion of the spring element 790, e.g., to protect the balloon 750 or other features of the apparatus 710, e.g., from being captured within windings of the spring element 790, similar to the previous embodiments. In addition or alternatively, the apparatus 710 may include one or more markers (not shown) to facilitate positioning and/or advancement of the apparatus 710 during use, e.g., on the distal end 734 of the inner member 730 and/or the balloon 750, similar to other embodiments herein.

Unlike the previous embodiments, the distal end 754 of the balloon 750 includes a distal extension or tip 780 that is shaped and/or otherwise configured to facilitate opening and/or closing of the outlet 758. For example, as best seen in FIG. 30B, the distal end 754 of the balloon 750 may terminate in a distal tip 780 that is flared outwardly away from the balloon 750, i.e., in the distal direction. The distal tip 780 may be integrally formed from the distal end 754 of the balloon 750, e.g., extruded or blown from the same material as the entire balloon 750, or may be formed separately and attached to the distal end 754, e.g., by bonding with adhesive, sonic welding, fusing, and the like.

Optionally, the distal end 754 and/or distal tip 780 of the balloon 750 may include a coating or other liner 757, e.g., adjacent the spring stop 755. For example, the liner 757 may include a lubricious and/or low surface energy material, e.g., PTFE, applied to the interior portion of the distal tip 780 and/or distal end 754 of the balloon 750 that may contact the nosecone 738, e.g., to reduce friction and/or adhesion between the balloon 750 and the nosecone 738, similar to the previous embodiments.

In an exemplary embodiment, best seen in FIG. 30B, the distal tip 780 may flare outwardly in a similar shape as the nosecone 738, e.g., to enhance receiving the nosecone 738 within the distal tip 780 and/or maximize surface contact therebetween, to substantially seal the outlet 758 when closed. In addition or alternatively, the distal tip 780 may increase the clearance of the outlet 758 around the nosecone 738 when opened, thereby increasing the open area of the outlet 758. The distal tip 780 may be biased to the outward flared shape and/or may have sufficient structural integrity to substantially maintain the outward flared shape when the nosecone 738 is directed away from the tip 780 to open the outlet 758.

Figure 31A:
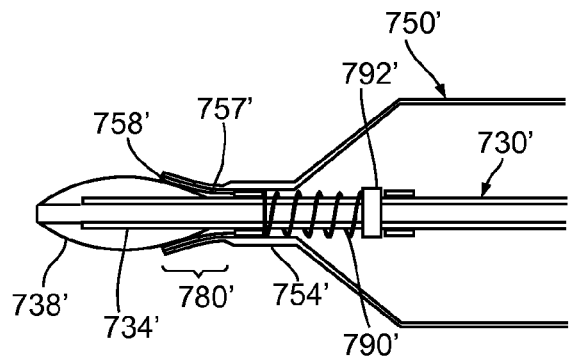
FIGS. 31A and 31B are details of an alternative embodiment of a distal end of the apparatus of FIG. 29, showing a valve closed and open, respectively.
Figure 31B:
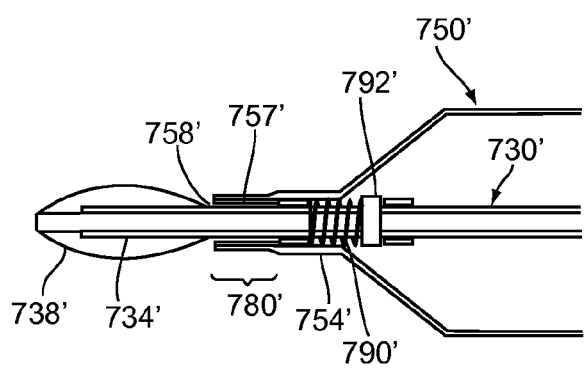

Alternatively, as shown in FIGS. 31A and 31B, the distal tip 780' may be biased to a substantially constant diameter, e.g., similar to the distal end 754,' but may expandable and/or relatively flexible compared to the distal end 754' of the balloon 750.' For example, the distal tip 780' may be sufficiently flexible and/or resilient to expand when the nosecone 738' is received within the outlet 758.' To facilitate such expansion, the distal tip 780' may have a wall thickness that is substantially less than the adjacent distal end 754' but sufficiently thick to resist tearing or other damage to the distal tip 780.'

Thus, as shown in FIG. 31A, when the nosecone 738' is seated within the tip 780,' the distal tip 780' may resiliently expand to provide substantial surface contact between the nosecone 738' and the distal tip 780,' which may enhance the resulting seal. The flexibility of the distal tip 780' may also resist indenting or otherwise pressing into the nosecone 738,' which may facilitate subsequent separation. When the nosecone 738' is directed away from the distal tip 780' to open the outlet 758,' the distal tip 780' may resiliently return towards its original diameter, as shown in FIG. 31B to define the outlet 758.' When the nosecone 738' is again seated into the distal tip 780,' the distal tip 780' may resist buckling and instead expand freely to enhance sealing without substantial leakage around the distal tip 780.'

Returning to FIG. 29, similar to the previous embodiments, the handle 760 may be coupled to or otherwise provided on the proximal end 722 of the outer member 720, e.g., for manipulating the outer member 720 and/or the entire apparatus 710. The handle 760 generally includes a housing 761 attached to the outer member 720, and may include one or more ports 764 for accessing the lumens of the apparatus 710 and/or one or more actuators 762 for directing the apparatus 710 between the infusion and expansion modes.

For example, the handle 760 may include a first side port 764*a* that communicates with the annular first lumen 726 in the outer member 720, and may include a connector, e.g., a Luer lock fitting, for coupling one or more fluid or vacuum sources to the apparatus 710, e.g., a syringe or other source (not shown) for delivering fluid through the first lumen 726 into the interior 756 of the balloon 750 and/or through the outlet 758 (depending upon the position of the inner member 730 and nosecone 738). In addition, the handle 760 may include a second port 764*b* that communicates with the second lumen 736 of the inner member 730. The second port 764*b* may include a connector, e.g., a Luer lock fitting and/or one or more seals, e.g., a hemostatic seal (not shown), that may accommodate receiving a guidewire or other instrument (not shown) through the second port 764*b* into the second lumen 736 while maintaining a substantially fluid-tight seal.

In addition, the handle 760 may include a slider, thumb control, push button, or other actuator 762 coupled to the inner member 730 for moving the inner member 730, e.g., to open and/or close the outlet 758 (see FIGS. 30A, 30B), similar to other embodiments herein. Optionally, the handle 760 may include one or more seals, bushings, and the like (not shown), between the outer and inner members 720, 730, which may guide the inner member 730 as it moves axially relative to the outer member 730 and handle 760, e.g., also similar to other embodiments herein.

The actuator 762 may be slidable within the slot 763 between a first or proximal position, shown in FIG. 29 for sealing the outlet 758 and a second or distal position (not shown) for opening the outlet 758, as shown in FIG. 30B.

Turning to FIG. 32, another embodiment of an apparatus 710" is shown that is generally similar to the apparatus 710 of FIG. 29 (with like features having the same reference numbers but including a" thereafter). For example, the apparatus 710" includes an outer member 720," an inner member 730," a balloon 750," a handle 760" with actuator 762," and a spring element 790" coupled between a collar 792" and a spring stop 755," similar to the previous embodiments. Optionally, the distal end 754" of the balloon 750" may include a distal tip 780" shaped and/or otherwise configured to facilitate opening and/or closing of the outlet 758," similar to the previous embodiments.

Unlike the previous embodiments, the nosecone 738" includes a beveled tip 739" (which may be provided on any of the embodiments described herein) that may be substantially flexible, semi-rigid or substantially rigid to facilitate advancement and/or other manipulation of the apparatus 710" within a body lumen (not shown). For example, the beveled tip 739″ may facilitate crossing obstructions or other features within a body lumen. When an obstruction is encountered by the beveled tip 739,″ the apparatus 710″ may be rotated about its longitudinal axis 727″ and/or advanced distally, allowing the beveled tip 739″ to climb over and/or around the obstruction and allow further advancement of the apparatus 710.″

Turning to FIGS. 33A and 33B, another alternative distal tip 739‴ is shown that may be provided on apparatus 710‴ (which may be any of the embodiments described elsewhere herein). Generally, the apparatus 710‴ includes an outer member 720,‴ an inner member 730,‴ a balloon 750,‴ a handle 760‴ with actuator 762,‴ and a spring element 790‴ coupled between a collar 792‴ and a spring stop 755,‴ similar to the previous embodiments. Optionally, the distal end 754‴ of the balloon 750‴ may include a distal tip 780‴ shaped and/or otherwise configured to facilitate opening and/or closing of the outlet 758,‴ similar to the previous embodiments.

Unlike the previous embodiments, the nosecone 738‴ includes an extended "J" shaped or otherwise curved distal tip 739‴ (which may be provided on any of the embodiments described herein) extending distally from the nosecone 738.‴ The distal tip 739‴ may have a length beyond the nosecone 738,‴ e.g., between about five and forty millimeters (5-40 mm). The distal tip 739‴ may be biased to a curved shape, e.g., as shown in FIG. 33B, yet may be substantially flexible such that, when a guidewire 699 or other instrument is inserted through the inner member 730,‴ the distal tip 739‴ may be at least partially straightened, as shown in FIG. 33A. The distal tip 739‴ may be useful for tracking the apparatus 710‴ through tortuous vessels or other body lumens (not shown).

For example, during use, the apparatus 710‴ may be advanced over a guidewire or other rail 699, which may substantially straighten the distal tip 739‴ as shown in FIG. 33A. Because of the flexibility of the distal tip 739,‴ the apparatus 710‴ may be easily advanced without the distal tip 739‴ bending the guidewire 699 or otherwise interfering substantially with advancement. However, when a tight or angulated branch lumen is encountered through which the apparatus 710‴ is to be directed from a main lumen, the guidewire 699 may be at least partially withdrawn, i.e., at least from the distal tip 739‴ such that the distal tip 739‴ resiliently returns towards its "J" or curved shape. The apparatus 710‴ may then be rotated and/or manipulated axially to insert the distal tip 739‴ into the target branch lumen and then advanced to direct the distal tip 739‴ sufficiently into the branch lumen. The guidewire 699 may then be advanced through the distal tip 739‴ and into the branch lumen to guide the apparatus 710‴ further into the patient's body.

Figure 34A:
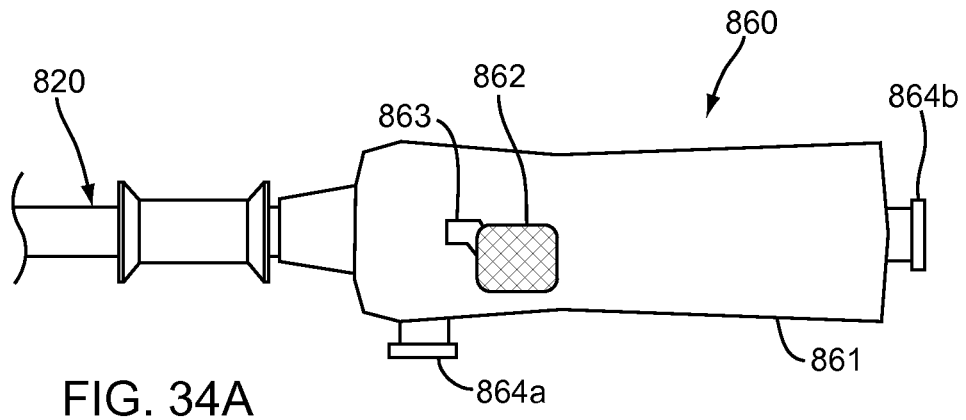
FIGS. 34A-34C are side views of alternative embodiments of handles that may be provided on an apparatus, such as the apparatus of FIGS. 29-33A.
Figure 34B:
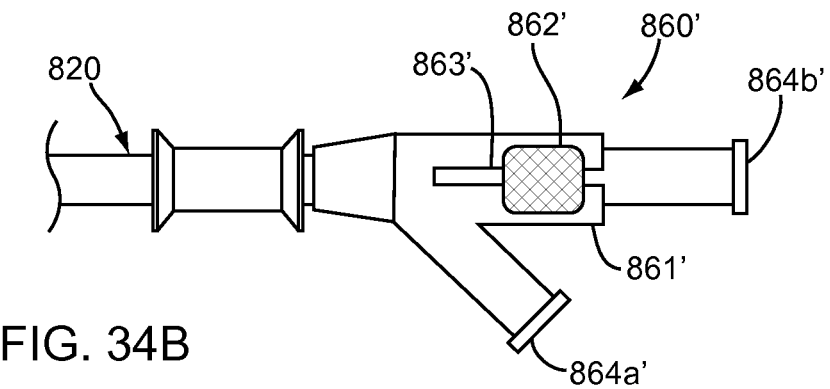
Figure 34C:
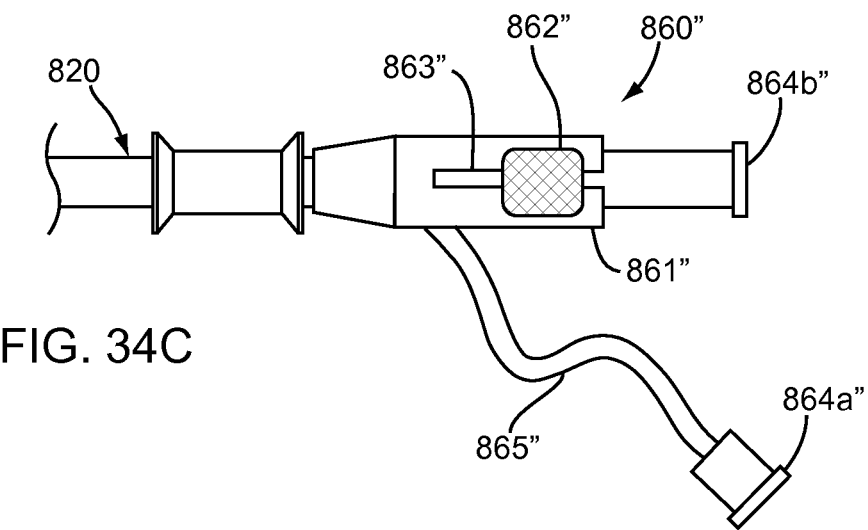

Turning to FIGS. 34A-34C, alternative embodiments of a handle are shown that may be provided on any of the apparatus herein, e.g., the apparatus 710, 710,' 710,″ or 710.‴ For example, FIG. 34A shows a handle 860 that includes a housing 861 attached to an outer member 820 (which may any of the embodiments herein), and may include one or more ports 864 for accessing the lumens of the apparatus and/or one or more actuators 862 for directing the apparatus between its different modes of operation.

For example, the handle 860 may include a first side port 864*a* that communicates with an annular first lumen (not shown) in the outer member 820, and may include a connector, e.g., a Luer lock fitting, for coupling one or more fluid or vacuum sources to the handle 820, similar to the previous embodiments. In addition, the handle 860 may include a second port 864*b* that communicates with a second lumen of an inner member (not shown), which may include a connector, e.g., a Luer lock fitting and/or one or more seals, e.g., a hemostatic seal (not shown), that may accommodate receiving a guidewire or other instrument (also not shown) through the second port 864*b* while maintaining a substantially fluid-tight seal.

In addition, the handle 860 may include a slider, thumb control, push button, or other actuator 862 coupled to the inner member (not shown) for moving the inner member, e.g., to open and/or close an outlet of a balloon (also not shown), similar to other embodiments herein. As shown, the housing 861 includes a slot 863 including a first or proximal region that receives the actuator 762 to seal the outlet and a second or distal region that receives the actuator 762 to open the outlet, similar to the previous embodiments.

Unlike the previous embodiments, the handle 860 may include a relatively long housing 861, e.g., having a length as long as or longer than a typical user's hand. Thus, such an embodiment may facilitate gripping and/or otherwise manipulating the handle 860 and consequently the apparatus in which the handle 860 is incorporated.

In contrast, FIG. 34B shows another embodiment of a handle 860' that includes a relatively short and/or small handle 861.' Some procedures may be performed in relatively tight fields of operation and consequently, compactness may be more important than the ergonomic benefits provided by longer handles, such as handle 860 of FIG. 34A. Thus, the handle 860' may include a slot 863' that extends substantially the entire length of the handle 860.' Also unlike handle 860, handle 860' of FIG. 34B includes a first side port 864*a'* that extends diagonally from the housing 861' rather than substantially perpendicular to the housing 861.'

FIG. 34C shows yet another embodiment of a handle 860″ similar to handle 860' except that the first side port 864*a″* is located on the end of a length of flexible tubing 865.″ Such tubing 865″ may provide more flexibility for the relative position of a source of fluid, e.g., a syringe or other inflation device (not shown) coupled to the first side port 864*a.″* In addition, the first side port 864*a″* may include a Luer-activated valve rather than a standard Luer fitting, such as those disclosed in U.S. Pat. Nos. 3,192,949, 5,390,898, or 5,775, 671, the entire disclosures of which are expressly incorporated by reference herein. Such valves may facilitate preparation and use of a balloon on an apparatus into which the handle 860″ is incorporated. For example, after preparing a path to the balloon to remove all air, e.g., between the first side port 864*a″* along a first lumen of outer member 820 to an interior of the balloon (not shown), the syringe or other inflation device may be removed from the first side port 864*a″* and refilled or another device may be attached to the first side port 864*a″* without substantial risk of reintroducing air into the apparatus. Thus, a user may not need to have all inflation and/or injection devices attached concurrently to the apparatus, but may remove and attach various devices, as needed during a procedure.

Figure 35:
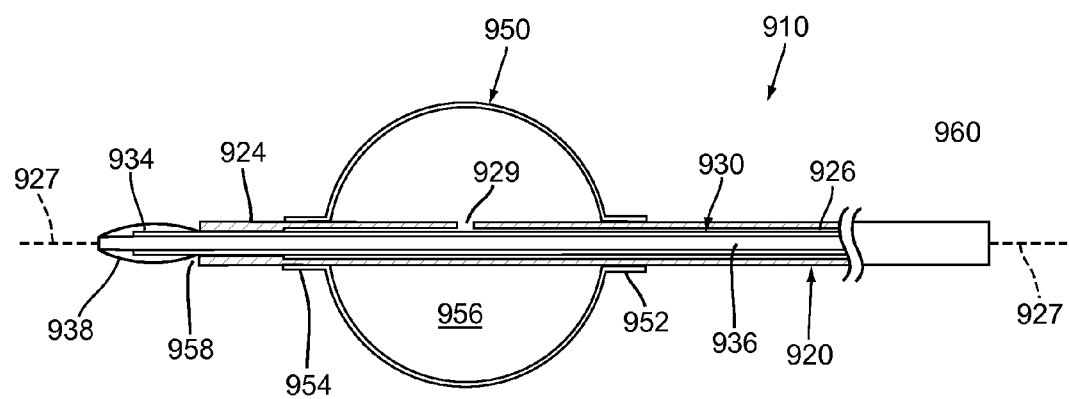
FIG. 35 is a side view of a distal end of yet another exemplary embodiment of an apparatus for treating a body lumen.

Turning to FIG. 35, still another embodiment of an apparatus 910 is shown for treating a body lumen generally similar to the previously embodiments. As shown, the apparatus 910 includes an outer tubular member 920, an inner member 930, an expandable balloon 950, and a handle 960, which may be constructed generally similar to the previous embodiments.

The outer member 920 includes a proximal end (not shown), a distal end 924 sized for introduction into a body lumen, and a first lumen 926 extending along a central longitudinal axis 927 therebetween, which may be constructed similar to the previous embodiments. The inner member 930 also includes a proximal end (not shown), a distal end 934, and, optionally, a second lumen 936, e.g., sized to slidably receive a guidewire or other instrument (not shown) therethrough. The inner member 930 is sized to be slidably received within the first lumen 926 of the outer member 920, e.g., such that an annular space is defined between the outer and inner members 920, 930 for passing one or more fluids therethrough, also similar to the previous embodiments. One or more sealing members, e.g., a nosecone 938, may be provided on the distal end 934 of the inner member 930 to provide a valve, also similar to the previous embodiments.

Unlike the previous embodiments, the balloon 950 includes proximal and distal ends 952, 954 that are both attached or otherwise coupled to the outer member 920. The outer member 920 includes one or more openings 929 (one shown) in the distal end 924 such that an interior 956 communicates with the first lumen 926 via the opening(s) 929. The distal end 934 of the inner member 930 may extend through the distal end 924 of the outer member 920, e.g., beyond an outlet 958 in the outer member 920 such that the outlet 958 defines an annular passage between the outer and inner members 920, 930. The inner member 930 may be movable relative to the outer member 920 between a first or proximal position where the nosecone 938 may be partially received in or otherwise engage the distal end 924 of the outer member 920 to substantially seal the outlet 958 and a second or distal position where the nosecone 938 is spaced away from the outer member 920 to open the outlet 958, similar to the previous embodiments.

The handle 960 may be attached to or otherwise provided on the proximal end of the outer member 920, e.g., for manipulating the outer member 920 and/or the entire apparatus 910. Similar to previous embodiments, the handle 960 may include an actuator (not shown) for operating the apparatus 910 in multiple modes, e.g., a first mode for dilating an obstruction within a body lumen, and a second mode for infusing fluid into a body lumen. For example, the actuator may be movable from a first position where the nosecone 938 substantially seals the outlet 958 and a second position where the outlet 958 is open.

With the nosecone 938 sealing the outlet 958, any fluid introduced into the first lumen 926 enters the interior 956 of the balloon 950, thereby expanding the balloon 950. Unlike the previous embodiments, because both the proximal and distal ends of the balloon 950 are attached to the outer member 920, the length of the balloon 950 may remain substantially constant during expansion and/or collapse. With the nosecone 938 directed away from the outer member 920 to open the outlet 958, the balloon 950 may remain collapsed and any fluid introduced through the first lumen 926 may exit the outlet 958 into a body lumen within which the apparatus 910 is introduced.

As shown, the inner member 930 may be integrally incorporated into the apparatus 910, similar to the previous embodiments. Alternatively, the inner member 930 may be decoupled or independent from the other components of the apparatus 910. For example, in one embodiment, the inner member 930 may be introduceable into a patient's body independently from the outer member 920, e.g., over a guidewire or instead of a guidewire. Once the distal end 934 is positioned at a desired location within the patient's body, the rest of the apparatus 910, i.e., the outer member 920 with the balloon 950 collapsed may be advanced over the inner member 930 to the desired location.

For example, the proximal end of the inner member 930 extending from the patient's body and may be backloaded through the outlet 958, and the outer member 920 advanced until the proximal end of the inner member 930 is received in or extends from the handle 960. The relative length of the outer and inner members 920, 930 may be such that the outlet 958 is disposed adjacent the nosecone 938 when the proximal end of the inner member 930 is received in or extends from the handle 960.

If desired, the handle 960 may include a coupler (not shown) that may be activated to engage the inner member 930 to a push button, thumb control, or other actuator (not shown) on the handle 960 once the outer member 920 is advanced sufficiently over the inner member 930. Thus, subsequently, the actuator may be activated to direct the inner member 930 and nosecone 938 axially relative to the outer member 920 to seal or open the outlet 958. It will be appreciated that other embodiments described elsewhere herein may be decoupled in this manner, i.e., provided with the inner member independent from the outer member and/or other components of the apparatus.

Optionally, an independent inner member 930 may include one or more markers or other visual indicators (not shown) that may provide confirmation to a user that the outer member 920 has been advanced sufficiently to place the outlet 958 adjacent the nosecone 938. For example, a marker may be provided on the proximal end of the inner member 930 that may be visible when the proximal end of the inner member 930 extends from the handle 960, thereby providing a visual indication that the nosecone 938 is sealing or adjacent the outlet 958. In addition or alternatively, the outer member 920 may be advanced until the distal end 924 contacts or engages the nosecone 938, which may provide tactile feedback that the nosecone 938 may be used to seal or open the outlet 958.

With the outer member 920 advanced over the inner member 930, the outlet 958 may be opened and fluid delivered into the desired location, e.g., contrast to facilitate imaging the desired location or one or more diagnostic and/or therapeutic agents. If desired to expand the balloon 950, the nosecone 938 may be directed proximally to seal the outlet 958, and fluid delivered to inflate the balloon 950, e.g., to dilate a stenosis or other lesion at the desired location, similar to the methods described above. After treating the desired location, the apparatus 910 may be directed to another location or removed from the patient's body. For example, the outer and inner members 920, 930 may be removed together or the outer member 920 may be removed first (e.g., after decoupling the outer member 920 from the inner member 930 if coupled together after advancing the outer member 920 over the inner member 930).

Turning to FIGS. 36-37C, yet another embodiment of an apparatus 1010 is shown for treating a body lumen that includes an outer tubular member 1020, an inner member 1030, and an expandable balloon 1050 carried by the inner member 1030, which may be constructed generally similar to other apparatus described above. Also similar to the previous embodiments, the apparatus 1010 may be operable in multiple modes, for example, a first mode for expanding the balloon 1050, e.g., to remove material, dilate, or otherwise treat a body lumen, and a second mode for delivering fluid into a body lumen, similar to other embodiments described elsewhere herein. Unlike previous embodiments, the apparatus 1010 includes an outlet and valve proximal to the balloon 1050 rather than distal to the balloon 1050.

Generally, the outer member 1020 includes a proximal end (not shown), a distal end 1024 sized for introduction into a body lumen, and a first lumen 1026 extending between the proximal end and an outlet 1027 in the distal end 1024. The inner member 1030 also includes a proximal end (not shown), a distal end 1034, and, optionally, may include a second lumen (not shown) extending between the proximal end and an outlet (also not shown), e.g., in a distal tip 1035, which may be sized to slidably receive a guide wire or other instrument (not shown) therethrough. A handle (not shown) may be provided on the proximal end of the outer member 1020 including an actuator (also not shown) coupled to the inner member 1020 for directing the inner member 1030 axially relative to the outer member 1020 to direct the apparatus 1010 between the different modes, similar to other embodiments herein.

The balloon 1050 includes a distal end 1052 coupled to the inner member 1030, e.g., adjacent the distal tip 1035, a proximal end 1052 coupled to the distal end 1034 of the inner member 1030 proximal to the distal tip 1035, and an interior 1056. The balloon 1050 may be formed from elastic material, e.g., to provide a compliant or semi-compliant balloon, or from substantially inelastic material, e.g., to provide a non-compliant balloon, similar to other embodiments herein.

Figure 37A:
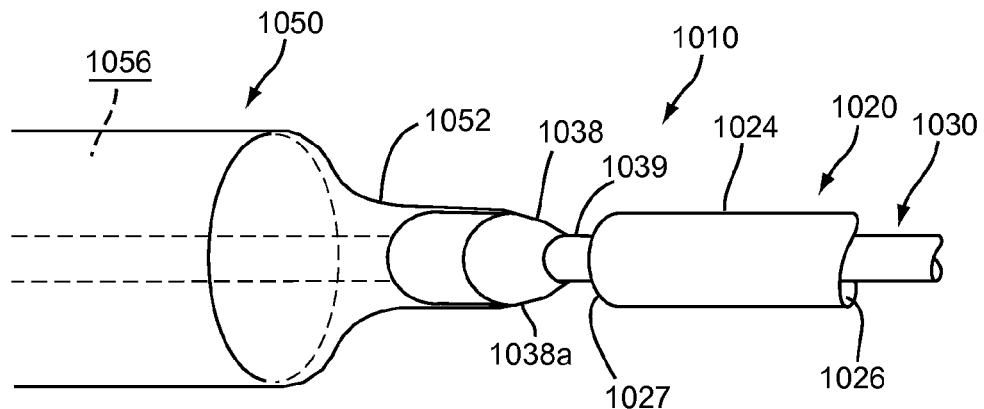
FIGS. 37A and 37B are details of the apparatus of FIG. 36 showing the valve in open and closed positions, respectively.
Figure 37B:
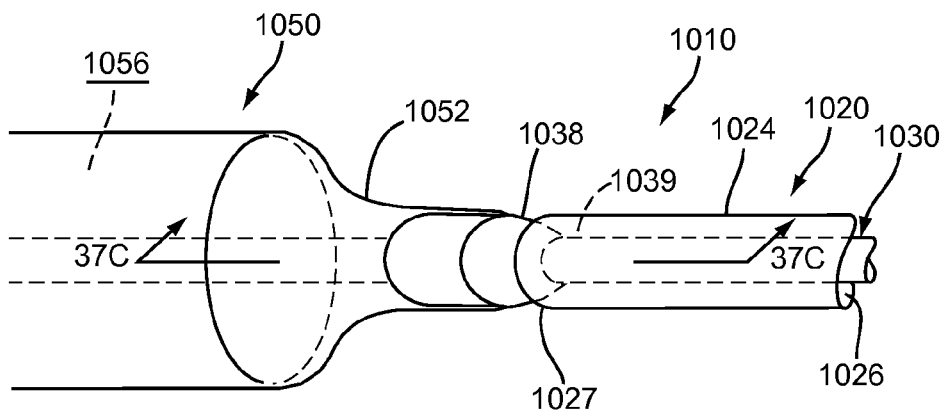
Figure 37C:
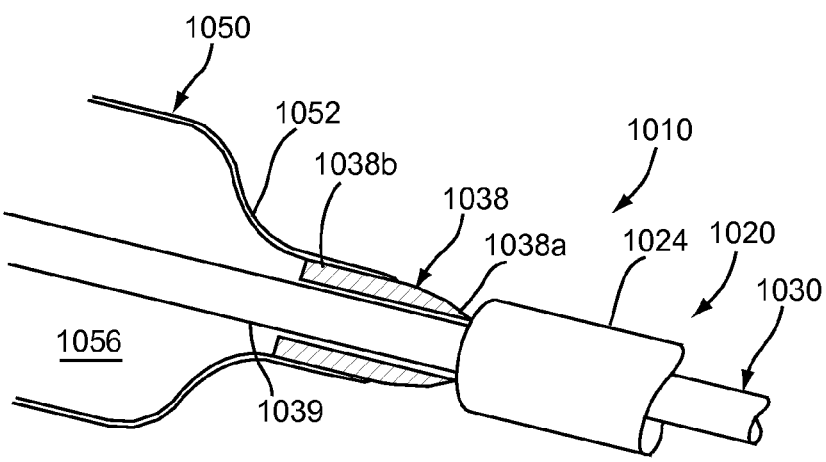
FIG. 37C is a cross-sectional view of the apparatus of FIGS. 36-37B taken along line 37C-37C of FIG. 37B.

As best seen in FIGS. 37A and 37B, a sealing member 1038 is also provided on the distal end 1034 of the inner member 1032 adjacent the proximal end 1052 of the balloon 1050. For example, as shown, the sealing member 1038 may be attached to an outer surface of the inner member 1030 and the proximal end 1052 of the balloon 1050 may be attached to the sealing member 1038. As shown, the proximal end 1052 of the balloon 1050 extends at least partially over the sealing member 1038 and may be attached to the sealing member 1038, e.g., by bonding with adhesive, sonic welding, fusing, interference fit, an exterior collar (not shown), and the like. Thus, the proximal end 1052 of the balloon 1050 may have a substantially fluid-tight seal with the sealing member 1038. The distal end 1054 of the balloon 1050 may be attached directly to the inner member 1030, e.g., using similar materials and/or methods.

The sealing member 1038 may have a size, e.g., outer diameter, that is larger than the inner diameter of the lumen 1026 of the outer member 1020, e.g., such that the sealing member 1038 may substantially seal the outlet 1027 of the outer member 1020, as described further below. Optionally, the sealing member 1038 may have a tapered shape, e.g., a tapered proximal end 1038a to facilitate seating or other engagement by the sealing member 1038 with the outlet 1027 of the outer member 1020. The sealing member 1038 may be formed from flexible material, e.g., which may enhance engagement with the distal end 1024 of the outer member 1020 to substantially seal the outlet 1027, similar to other embodiments herein.

As best seen in FIG. 37C, the sealing member 1038 may include one or more passages 1039 extending generally longitudinally between the proximal end 1038a and a distal end 1038b of the sealing member 1038. The passage(s) 1039 may include an annular passage or may include a plurality of passages formed in the sealing member 1038. For example, the sealing member 1038 may be provided as a length of tubing with one or more longitudinal grooves formed in an inner wall thereof. When the sealing member 1038 is attached to or otherwise placed around the inner member 1030, the groove(s) may extend along the outer wall of the inner member 1030, thereby together defining the passage(s) 1039. Alternatively, enclosed lumens may be formed within the wall of the tubing to provide the passage(s) 1039.

During assembly, the sealing member 1038 may be placed around the inner member 1030 at the desired location on the distal end 1034 and attached thereto, e.g., by bonding with adhesive, sonic welding, fusing, and the like. The proximal end 1052 of the balloon 1050 may then be positioned partially over the sealing member 1038 and attached thereto. Thus, the passage(s) 1039 may communicate from the outside of the proximal end 1038a of the sealing member 1038 with the interior 1056 of the balloon 1050. The distal end 1054 of the balloon 1050 may be attached to the distal end 1034 of the inner member 1030. Consequently, the interior 1056 of the balloon 1050 may be substantially sealed other than the passage(s) 1039 through the sealing member 1038.

The outer member 1020 may be positioned around the inner member 1030 and the handle and actuator coupled to the outer and inner members 1020, 1030, similar to other embodiments herein. The apparatus 1010 may be operated in a first mode for delivering fluid into a body lumen (not shown) into which the apparatus 1010 is introduced and a second mode for inflating the balloon 1050. For example, the inner member 1030 may be movable between a first or distal position, shown in FIG. 37A, where the sealing member 1038 is spaced apart from the outlet 1027 of the outer member 1020, and a second or proximal position, shown in FIG. 37B, where the sealing member 1038 is seated against and/or partially within the outlet 1027. In the first position, fluid delivered through the lumen 1026 of the outer member 1020 may exit the outlet 1027 and enter the body lumen proximal to the balloon 1050. In the second position, fluid delivered through the lumen 1026 may enter through the passage(s) 1039 in the sealing member 1038 and into the interior 1056 of the balloon 1050, thereby inflating the balloon 1050.

During use, the apparatus 1010 may be introduced into a body lumen (not shown), e.g., using similar methods to other embodiments herein. The apparatus 1010 may be provided with the inner member 1030 in the proximal position such that the sealing member 1038 is seated into the outlet 1027. This may provide a substantially smooth transition for the distal end 1024 of the outer member 1020 (in addition to sealing the outlet 1027), e.g., which may facilitate advancement of the apparatus 1010 with minimal risk of damaging the walls of body lumens, e.g., when the apparatus 1010 is advanced through tortuous anatomy. Alternatively, the apparatus 1010 may be introduced with the inner member 1030 in the distal position.

At any time, if it is desired to deliver fluid into the body lumen, e.g., contrast to facilitate fluoroscopy or other external imaging, the inner member 1030 may be directed to the distal or first position to space the sealing member 1038 from the distal end 1024 of the outer member 1020 and open the outlet 1027 (FIG. 37A). Fluid may then be delivered through the lumen 1026 of the outer member and out the outlet 1027 into the body lumen. Because the outlet 1027 is spaced away from the sealing member 1038, substantially all of the fluid is injected into the body lumen and does not pass through the passage(s) 1039 into the balloon 1050.

When it is desired to expand the balloon 1050, the inner member 1030 may be directed to the proximal or second position to seat the sealing member 1038 at least partially in the outlet 1027 of the outer member 1020 (FIG. 37B). The sealing member 1038 may provide a substantially fluid-tight seal with the distal end 1024 of the outer member 1020 such that subsequent fluid delivery injects the fluid through the passage(s) 1039 of the sealing member 1038 into the interior of the balloon 1050, thereby inflating the balloon 1050. After the balloon 1050 has been inflated, e.g., to remove material, dilate an obstruction, and/or otherwise treat a body lumen, the fluid may be evacuated from the interior 1056 through the passage(s) 1039 and the lumen 1026. Alternatively, the inner member 1030 may be directed towards the first position to disengage the sealing member 1038 and open the outlet 1026. The fluid within the balloon 1050 may then be free to escape through the passage(s) 1039 into the body lumen and deflate the balloon 1050.

Optionally, if desired, the inner member 1030 may be positioned at an intermediate position, i.e., between the first and second positions, in which fluid delivered from the outlet 1026 may be divided such that some fluid enters the passage(s) 1039 and expands the balloon 1050 while the remaining fluid is delivered into the body lumen. The relative amount of inflation and fluid delivery into the body lumen may be adjusted, as desired, simply by directing the inner member 1030 proximally or distally to move the sealing member 1038 closer to or further from the outlet 1027. This procedure may be accomplished using external imaging, e.g., if the fluid includes radiopaque contrast, to monitor the inflation and/or position of the balloon 1050 and/or the surrounding vasculature within which the balloon 1050 is located.

In another option, the apparatus 1010 may be used to deliver and aspirate fluid using the outlet 1027. For example, a user may want to deliver and remove one or more diagnostic and/or therapeutic agents within a body lumen using the apparatus 1010. In one example, contrast, dyes, or other material for facilitating imaging may be delivered into the body lumen from the outlet 1027 (with the inner member 1030 and sealing member 1038 in the distal position) and then aspirated back into the outlet 1027 to reduce the amount of contrast that remains within the body lumen or travels to other locations in the patient's body.

In another example, a lytic agent may be delivered into the body lumen, e.g., to break up clot or other material within the body lumen, and then loose material may then be aspirated into the outlet 1027 and through the lumen 1026, which may reduce the risk of bleeding or otherwise exposing the lytic agent systemically to the patient's body. The outlet 1027 may also be used to aspirate pieces of thrombus or other material that is not dissolved or broken down by the agent and/or is otherwise loosened within the body lumen. During such procedures, the balloon 1050 may be at least partially inflated, e.g., by directing the inner member 1030 to an intermediate position, to stop or reduce flow through the body lumen while the one or more agents are delivered and aspirated, which may also reduce exposure of other locations to the agent(s) delivered into the body lumen.

Figure 38:
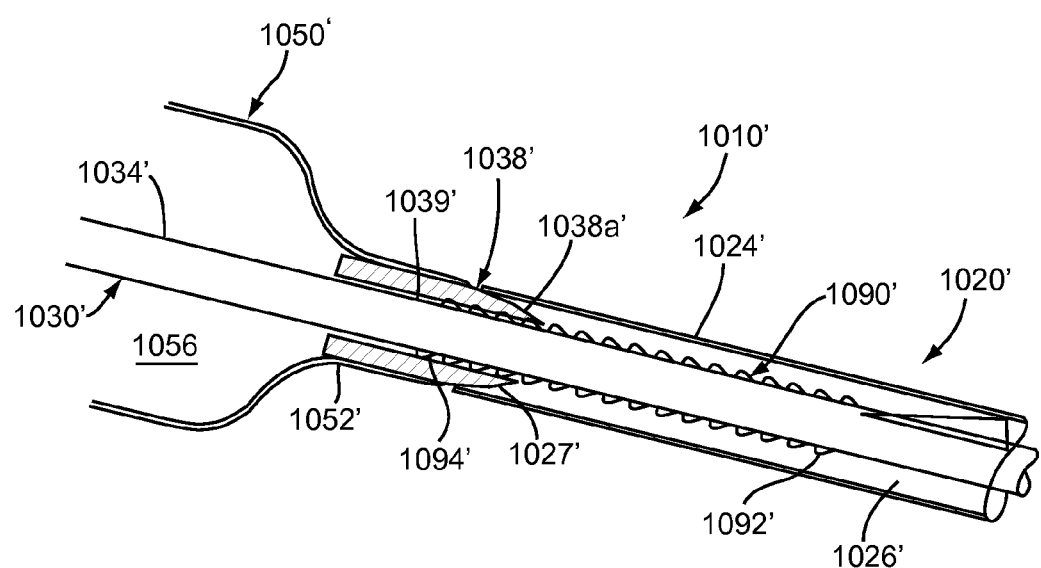
FIG. 38 is a cross-sectional view of an alternative embodiment of the apparatus of FIGS. 36-37C.

Turning to FIG. 38, an alternative embodiment of the apparatus 1010' is shown similar to the apparatus 1010 of FIGS. 36-37C. The apparatus 1010' includes an outer member 1020,' an inner member 1030,' a balloon 1050,' and a sealing member 1038' similar to the apparatus 1010. The apparatus 1010' may be operable in first and second modes by directing the inner member 1030' between a first or distal position and a second or proximal position, also similar to the apparatus 1010.

In addition, however, the apparatus 1010' includes a spring or other biasing mechanism 1090' coupled between the inner and outer members 1030,' 1020' for biasing the inner member 1030' to one of the first and second positions. For example, as shown, the spring 1090' may bias the inner member 1030' to the proximal position, i.e., such that the outlet 1027' of the apparatus 1010' is normally closed and/or enhancing seating of the sealing member 1038' into the outlet 1027.' The bias may be overcome by directing the inner member 1030' distally to unseat the sealing member 1038' and open the outlet 1027.'

As shown, the spring 1090' includes a first end 1092' attached or otherwise coupled to the distal end 1024' of the outer member 1020,' and a second end 1094' attached or otherwise coupled to the distal end 1034' of the inner member 1030' and/or the sealing member 1038.' As shown, the second end 1094' of the spring 1090' may be attached between the sealing member 1038' and the inner member 1030' or otherwise to the sealing member 1038,' while still accommodating the passage 1039' extending through the sealing member 1038.' In exemplary embodiments, the ends 1092,' 1094' of the spring 1090' may be attached to the inner and outer members 1030,' 1020' by bonding with adhesive, sonic welding, fusing, interference fit, one or more connectors (not shown), and the like.

The relative diameter of the spring 1090' and the inner member 1030' may be set to reduce the risk of over-extension of the spring 1090.' For example, the spring 1090' may be relaxed or under slight tension when the inner member 1030' is in the proximal position and may be placed under higher tension when the inner member 1030' is directed distally. As the spring 1090' is placed under higher tension, the diameter of the spring 1090' may decrease thereby increasing friction between the spring 1090' and the inner member 1030.' This increasing friction may reduce the risk of over-extending the spring 1090,' which may otherwise plastically deform the spring 1090' or otherwise prevent the spring 1090' from biasing the inner member 1030' proximally towards the proximal position.

Figure 39:
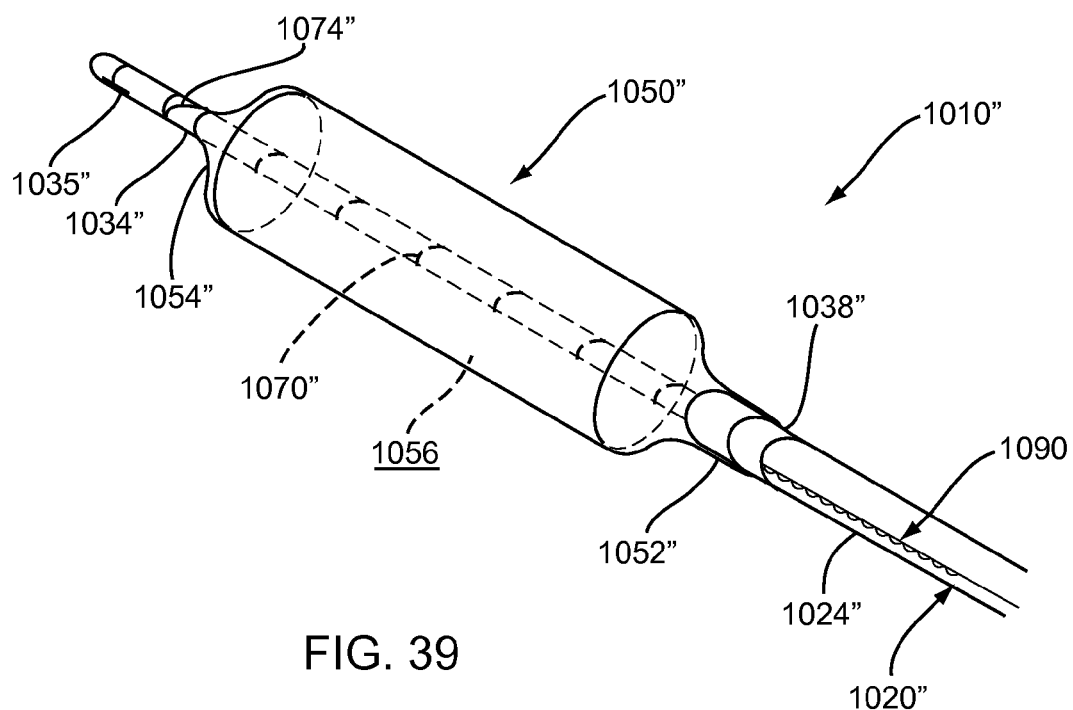
FIG. 39 is a perspective view of a distal end of yet another exemplary embodiment of an apparatus for treating a body lumen.

Turning to FIG. 39, yet another alternative embodiment of the apparatus 1010" is shown similar to the apparatus 1010' of FIG. 38. The apparatus 1010" includes an outer member 1020," an inner member 1030," a balloon 1050," a sealing member 1038," and a spring 1090," similar to the apparatus 1010.' The apparatus 1010" may be operable in first and second modes by directing the inner member 1030" between a first or distal position and a second or proximal position, also similar to the apparatus 1010, 1010.'

In addition, the apparatus 1010" includes a helical member 1070" within the balloon 1050" that may be expanded to an expanded helical shape, similar to other embodiments herein. For example, the helical member 1070" may include a first or proximal end coupled to the outer member 1020''' (not shown) and a second or distal end 1074" coupled to the inner member 1030," adjacent the distal end 1054" of the balloon 1050." Thus, the apparatus 1010" may also be operated in a third mode, e.g., by directing the inner member 1030" proximally from the second position to a third position in which the helical member 1070" is axially compressed and radially expanded. The balloon 1050" may remain collapsed while the helical member 1070" is expanded or may be inflated and then collapsed after the helical member 1070" is expanded, similar to other embodiments herein.

After the helical member 1070" and balloon 1050" are used to remove material in the expanded helical shape, the inner member 1030" may be directed distally to return the helical member 1070" to its original contracted shape around the inner member 1030." This action may extend the spring 1090" and open the outlet 1027." However, as discussed above, the relative sizes of the spring 1090" and the inner member 1030" may be such that the spring 1090" compresses as it extends and frictionally engages the inner member 1030," thereby reducing the risk of the spring 1090" over-extending while the inner member 1030" is directed distally.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for treating a body lumen of a patient using a balloon apparatus comprising an outer member including a first lumen extending between proximal and distal ends thereof, an inner member having a proximal end and a distal end slidable within the first lumen, an inner member distal tip, wherein the inner member distal tip is softened, and a balloon comprising a proximal end attached to the outer member distal end, a distal end including an outlet and an interior communicating with the first lumen and the outlet, and a helical member coupled between the outer member and the inner member, wherein the inner member comprises a second lumen that is sized to slideably receive a guidewire that may be delivered into the body lumen, the method comprising, in combination:
   introducing the distal end of the outer member into a body lumen with the balloon in a contracted condition and the inner member in a proximal position such that the outlet is substantially sealed by a sealing member on the inner member distal end;
   directing an actuator on a proximal end of the balloon apparatus to move the inner member to a distal position consequently directing the sealing member distally to open the outlet;
   delivering a first fluid through the first lumen such that the first fluid passes through the balloon interior and exits the open outlet into the body lumen;
   directing the inner member towards the proximal position to substantially seal the outlet with the sealing member, a spring element biasing the inner member to enhance the sealing member sealing the outlet; and
   delivering a second fluid through the first lumen with the outlet substantially sealed, thereby expanding the balloon from the contracted condition to an enlarged condition.

2. The method of claim 1, further comprising:
   directing the balloon to an expanded helical shape within the body lumen; and
   directing the balloon along a wall of the body lumen to the location of material and distal to the location of material in the expanded helical shape to remove material from the wall of the body lumen.

3. The method of claim 2, wherein directing the balloon to the expanded helical shape comprises:
   expanding the balloon at least partially towards the enlarged condition;
   expanding the helical member within the balloon interior with the balloon at least partially expanded towards the enlarged condition; and
   collapsing the balloon around the expanded helical member such that the balloon conforms substantially to the shape of the helical member.

4. The method of claim 2, wherein directing the balloon to the expanded helical shape comprises expanding the helical member within the balloon interior with the balloon collapsed such that the balloon conforms substantially to the shape of the helical member.

5. The method of claim 2, wherein directing the balloon to the expanded helical shape comprises directing the inner member proximally relative to the outer member, thereby compressing the balloon axially and expanding the helical member within the balloon interior, the balloon conforming substantially to the shape of the helical member as the helical member is expanded.

6. The method of claim 1, wherein the body lumen comprises at least one of an arterio-venous graft and an arterio-venous fistula.

7. The method of claim 1, wherein the helical member is disposed around the inner member within the balloon interior in a reduced profile when the distal end of the outer member is introduced into the body lumen, wherein a distal end of the helical member is coupled to the spring element, the spring element providing compliance to the helical member in the reduced profile when the inner member is directed to the distal position.

8. The method of claim 1, wherein the balloon is expanded to the enlarged condition to dilate a lesion within the body lumen.

9. The method of claim 1, wherein the first fluid or the second fluid comprises contrast, the method further comprising:
   imaging the body lumen using external imaging that is enhanced by the contrast; and manipulating the distal end of the outer member within the body lumen based at least in part on the external imaging.

10. The method of claim 1, wherein the first fluid or the second fluid comprises one or more diagnostic or therapeutic agents.

11. A method for treating a body lumen of a patient using an apparatus comprising an outer tubular member comprising a first lumen extending between proximal and distal ends thereof, and a balloon comprising a proximal end attached to the outer tubular member distal end, a distal end including an outlet and an interior communicating with the first lumen and the outlet, and a helical member coupled between the outer tubular member and an elongate member, the method comprising, in combination:
   introducing a distal end of the elongate member into a patient's body until the distal end is disposed within a body lumen, the elongate member comprising a sealing member on the distal end;
   advancing the distal end of the outer member over the elongate member with the balloon in a contracted condition until the balloon outlet is disposed adjacent the sealing member;
   coupling an actuator on the outer member proximal end to the elongate member;
   directing the actuator to a first position wherein the sealing member substantially seals the outlet;
   delivering fluid into the first lumen with the outlet substantially sealed, thereby expanding the balloon to an enlarged condition;
   directing the actuator to a second position wherein the sealing member is spaced from the outlet;
   delivering fluid into the first lumen with the sealing member spaced from the outlet, thereby delivering the fluid from the outlet into the body lumen; and
   directing the balloon to an expanded helical shape within the body lumen wherein the expanded helical shape includes a first helix and a second helix, the first helix and the second helix having different diameters; directing the balloon along a wall of the body lumen in the expanded helical shape to remove material from the wall of the body lumen; and collapsing the balloon around the helical member.

12. The method of claim 11, further comprising:
   decoupling the actuator from the elongate member; and removing the outer member from around the elongate member.

13. The method of claim 11, further comprising:
   directing the balloon to an expanded helical shape within the body lumen whereby the expanded helical shape includes more than two helices having different diameters.

* * * * *